(12) United States Patent
Huo et al.

(10) Patent No.: US 6,464,999 B1
(45) Date of Patent: Oct. 15, 2002

(54) BIOADHESIVE MEDICAL DEVICES

(75) Inventors: Peter P. Huo; Sheila Wallin, both of Irvine, CA (US)

(73) Assignee: Galt Incorporated, Irvine, CA (US)

( * ) Notice: Subject to any disclaimer, the term of this patent is extended or adjusted under 35 U.S.C. 154(b) by 0 days.

(21) Appl. No.: 09/421,810

(22) Filed: Oct. 20, 1999

Related U.S. Application Data

(63) Continuation-in-part of application No. 09/098,396, filed on Jun. 17, 1998, now Pat. No. 6,036,119.

(51) Int. Cl.[7] .................................................. A61F 13/00
(52) U.S. Cl. ........................ 424/422; 424/423; 424/430; 424/400; 424/78.08; 424/78.17; 424/486; 424/487; 604/890.1; 604/891.1
(58) Field of Search .............................. 427/385.5, 399; 424/400, 422, 423, 78.08, 78.17, 484, 486, 487, 430; 604/890.1, 891.1

(56) References Cited

U.S. PATENT DOCUMENTS

| | | |
|---|---|---|
| 2,638,093 A | 5/1953 | Kulick |
| 3,768,102 A | 10/1973 | Kwan-Gett et al. |
| 3,797,478 A | 3/1974 | Walsh et al. |
| 3,812,841 A | 5/1974 | Isaacson |
| 3,863,622 A | 2/1975 | Buuck |
| 3,939,821 A | 2/1976 | Roth |
| 4,197,835 A | 4/1980 | Reinicke |
| 4,204,282 A | 5/1980 | Bolt |
| 4,222,377 A | 9/1980 | Burton |
| 4,408,597 A | 10/1983 | Teney, Jr. |
| 4,551,862 A | 11/1985 | Haber |
| 4,554,533 A | 11/1985 | Leighton |
| 4,587,955 A | 5/1986 | Gengler |
| 4,679,546 A | 7/1987 | Van Wallwijk van Dorn et al. |
| 4,705,518 A | 11/1987 | Baker et al. |
| 4,716,901 A | 1/1988 | Jackson et al. |
| 4,731,083 A | 3/1988 | Fischell |
| 4,784,660 A | 11/1988 | Fischell |
| 4,832,680 A | 5/1989 | Haber |
| 4,846,784 A | 7/1989 | Haber |
| 4,850,963 A | 7/1989 | Sparks |
| 4,878,889 A | 11/1989 | Polyak |
| 4,968,294 A | 11/1990 | Salama |
| 4,994,019 A | 2/1991 | Fernandez et al. |
| 5,064,434 A | 11/1991 | Haber |
| 5,088,980 A | 2/1992 | Leighton |
| 5,097,848 A | 3/1992 | Schwarz |
| 5,123,428 A | 6/1992 | Schwarz |
| 5,140,999 A | 8/1992 | Ardito |
| 5,197,984 A | 3/1993 | Kedem |
| 5,437,604 A | 8/1995 | Kulisz et al. |
| 5,476,434 A | 12/1995 | Kalb et al. |
| 5,509,889 A | 4/1996 | Kalb et al. |
| 5,770,627 A * | 6/1998 | Inoue et al. ............. 514/772.1 |
| 5,782,916 A | 7/1998 | Pintauro et al. |
| 6,143,037 A * | 11/2000 | Goldstein et al. ............. 623/66 |

FOREIGN PATENT DOCUMENTS

WO    WO 96/02214    2/1996

OTHER PUBLICATIONS

J. Gundian, et al., "Mayo Clinic Experience with the AS800 Artificial Urinary Sphincter . . . ", Urology, 41:318–321 (1993).

(List continued on next page.)

Primary Examiner—Thurman K. Page
Assistant Examiner—Lilian Di Nola Baron
(74) Attorney, Agent, or Firm—Knobbe, Martens, Olson & Bear, LLP

(57) ABSTRACT

Disclosed herein are bioadhesive medical devices formed in whole or in part of a cohesive bioadhesive copolymer of a carboxyl functional monomer and a hydrophobic functional monomer.

5 Claims, 33 Drawing Sheets

OTHER PUBLICATIONS

R. Janknegt, et al., "Electrically stimulated gracilis sphincter for treatment of . . . ", Lancet, 340:1129–1130 (1992).

M.D. Craggs, et al., "A preliminary report on a new hydraulic sphincter for . . . ", Journal of Medical Engineering & Technology, 15:58–62 (1991).

O. Lukkarinen, et al., "Treatment of Urinary Incontinence with an Implantable . . . ", Scand J Urol Nephrol, 23:85–88 (1989).

M. Abbar, et al., "Une revolution tranquille: l'endoprothese urethrale . . . ", Progres en Urologie 3:771–777 (1993).

A. Gruneberger, et al., "Entwicklung eines magnetischen Urethralverschlusses . . . " Zentralblatt fur Gynakologie, 115:328–331 (1993).

Summary of DIALOG/Derwent World Pat. computer search, Mar. 17, 1995.

Summary of DIALOG/MEDLINE/BIOSIS/SciSearch/EMBASE computer search Mar. 17, 1995.

Preliminary Prospectus: UroMed Corporation, PaineWebber Incorporated Vector Securities International, Inc., Jan. 24, 1994.

Brochure: *AMS Sphincter 800*, Urinary Prosthesis, Dry Facts of Incontinence Treatment, Pfizer American Medical Systems®, Jun. 1, 1991.

Brochure: HK Medical Technologies Incorporation, AUTO-CATH™ 100, 1994.

S. Stanton, et al., "The mechanism of Continence", Surgery of Female Incontinence, 2d Ed., pp. 1–21 (1986).

\* cited by examiner

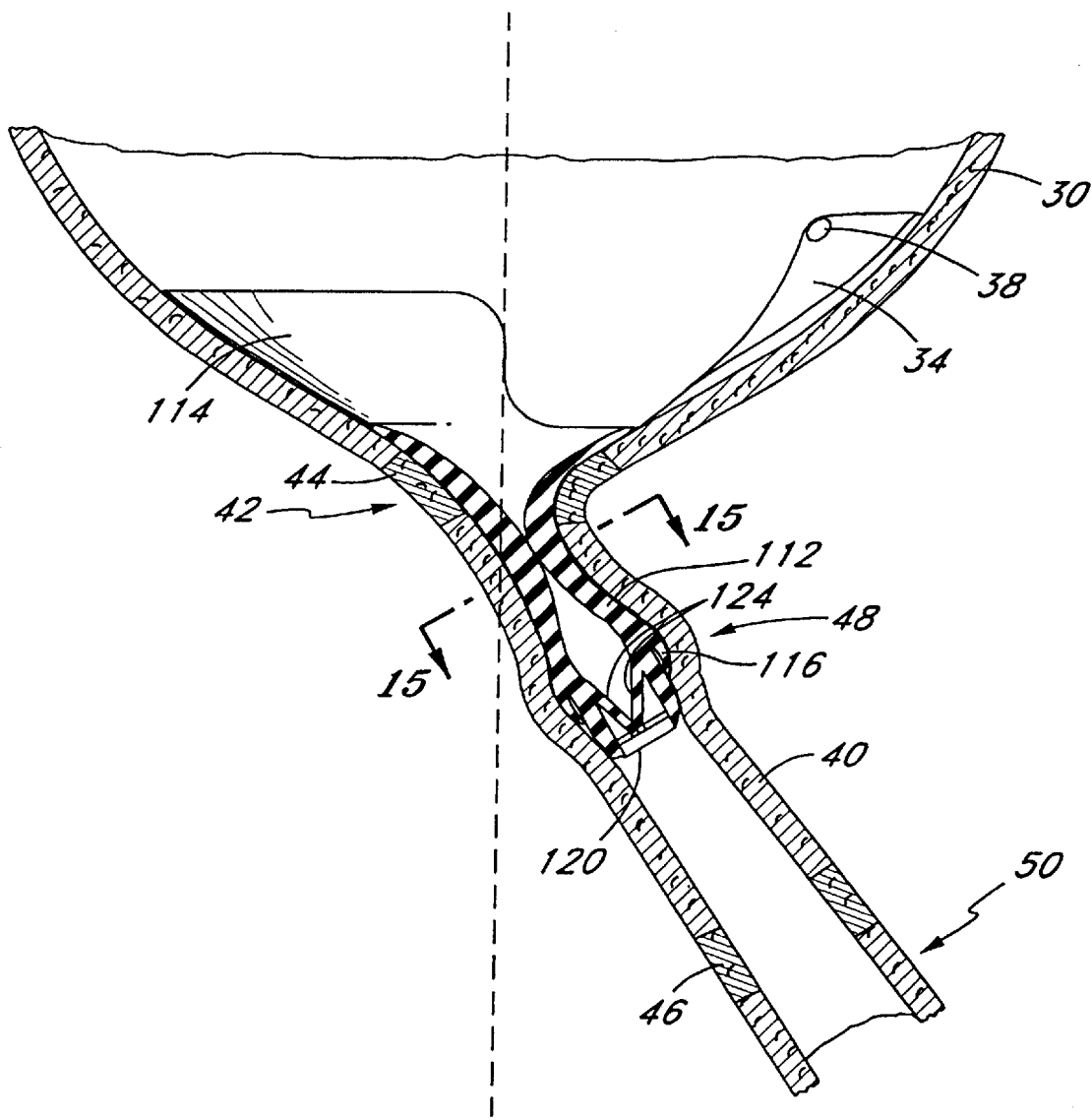
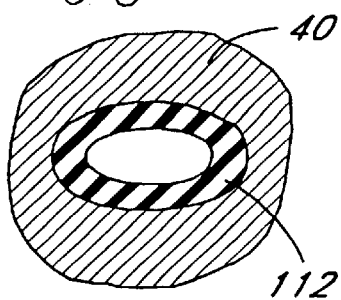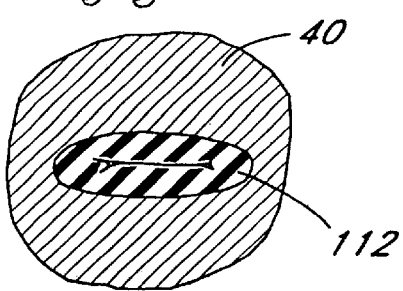

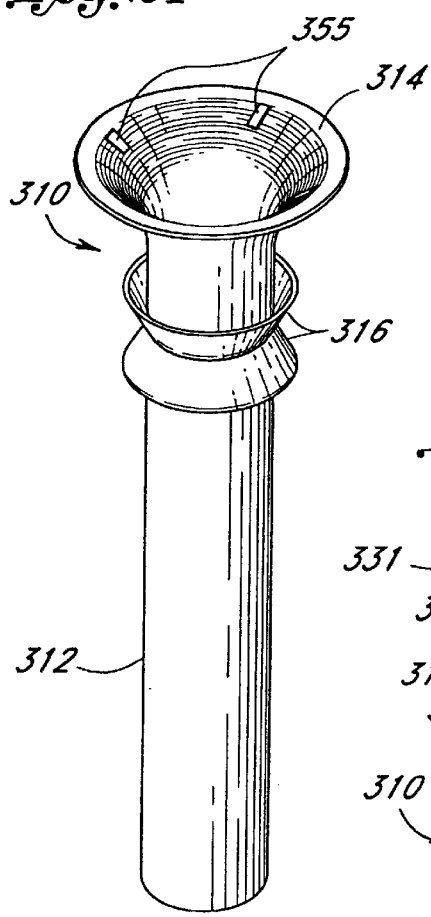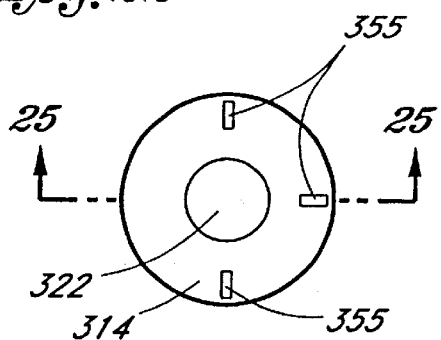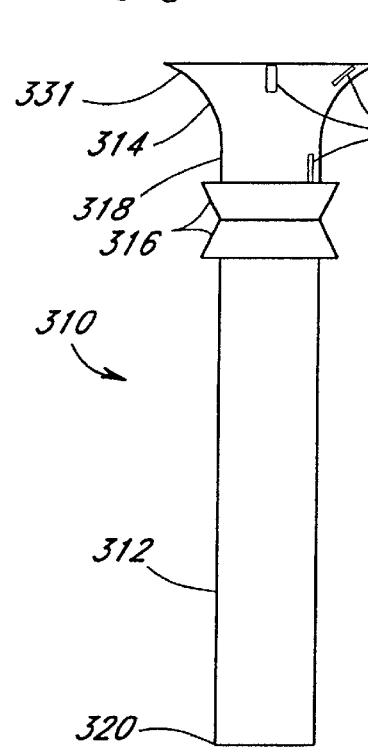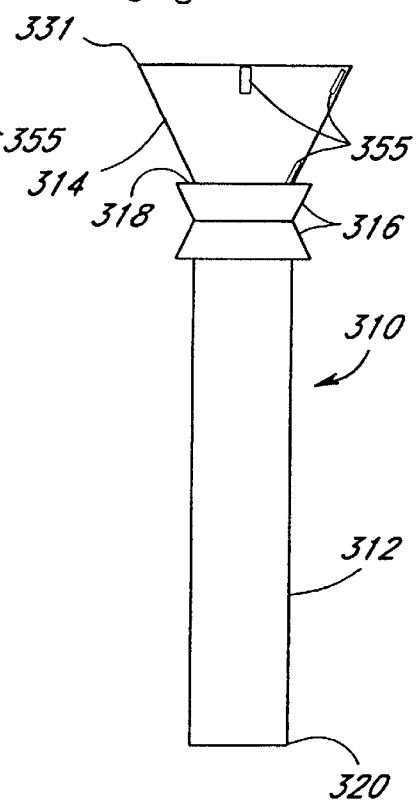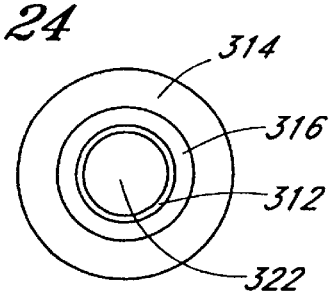

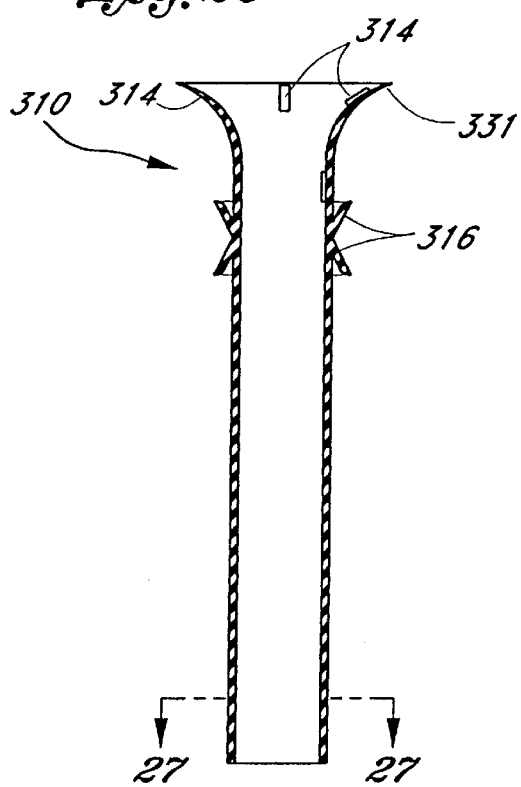
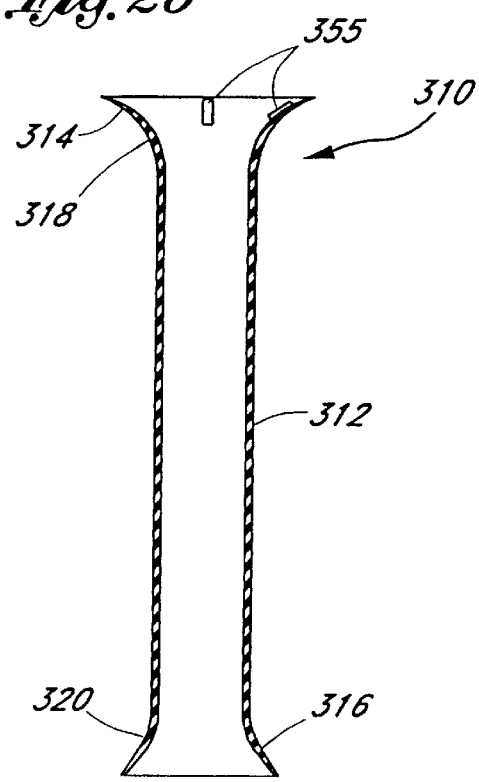
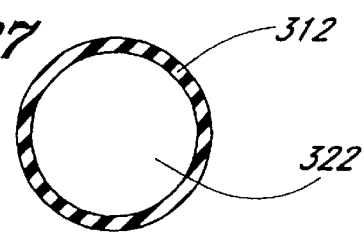
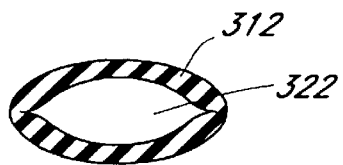
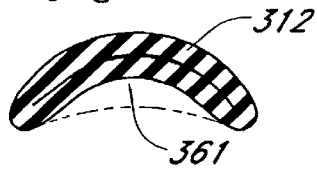
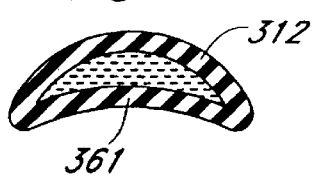

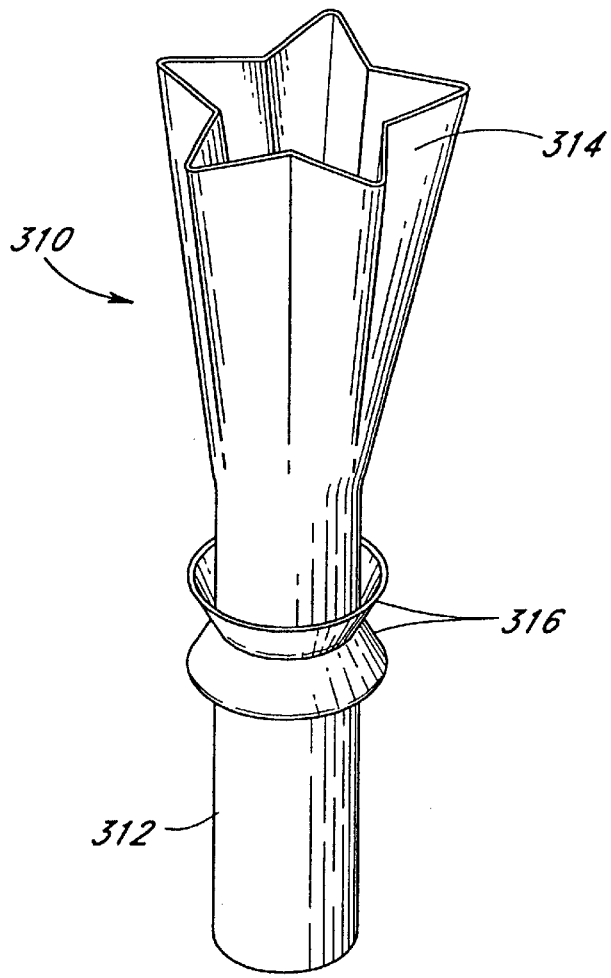
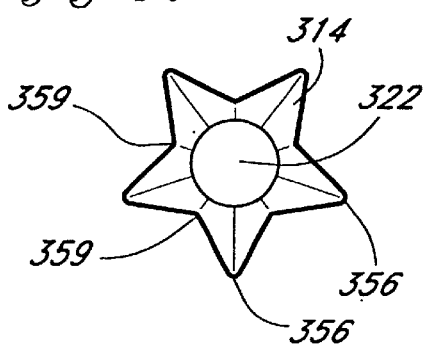
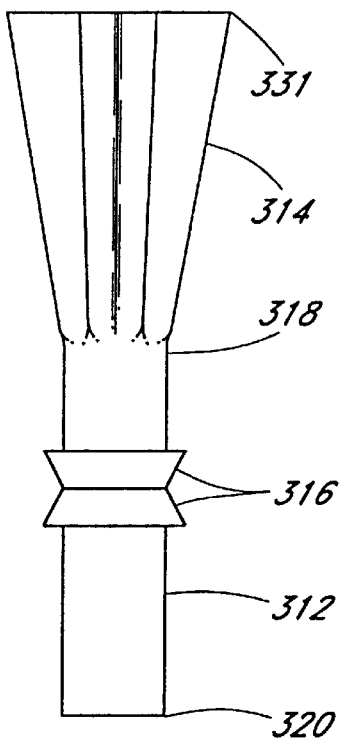
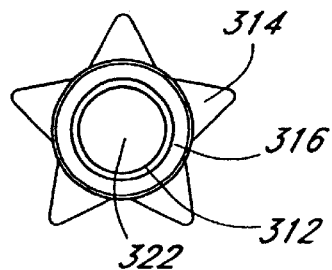

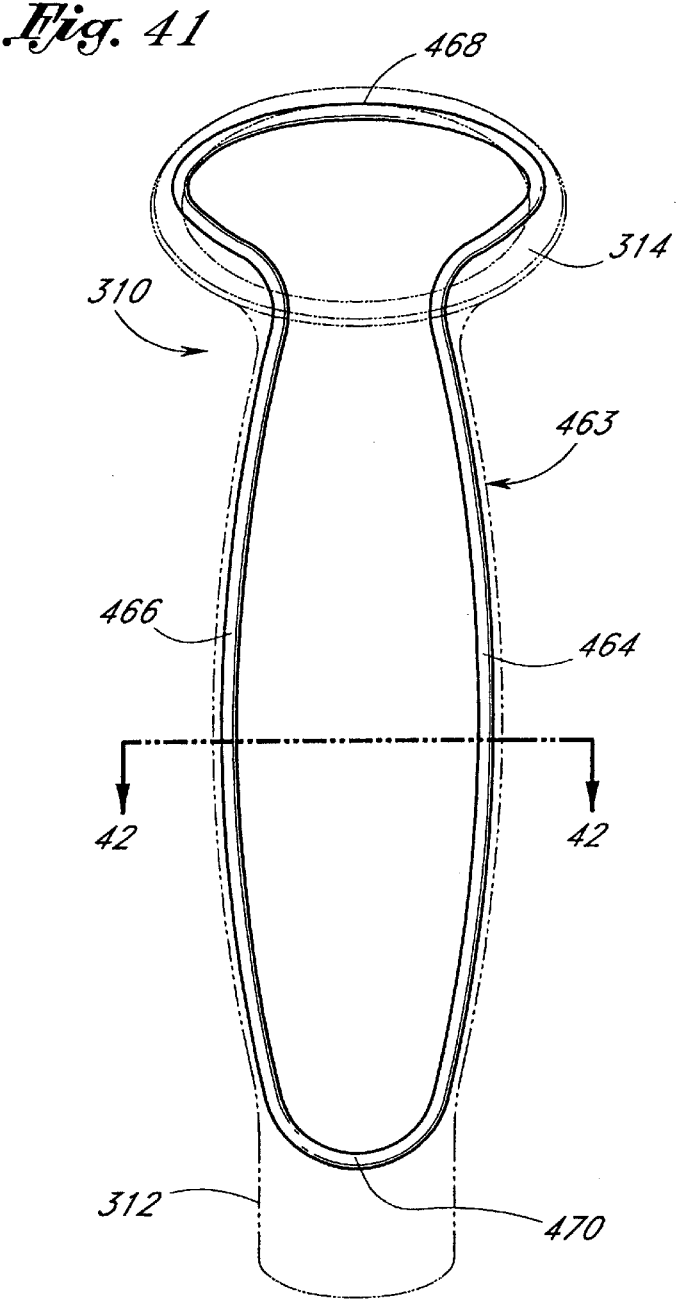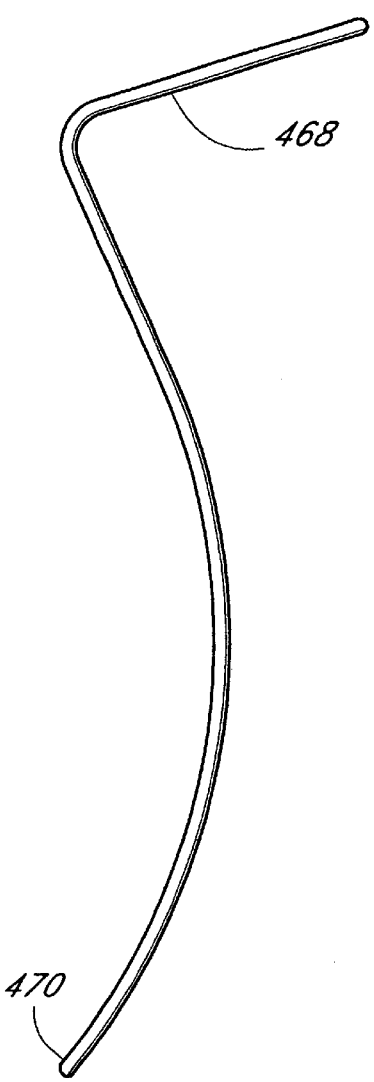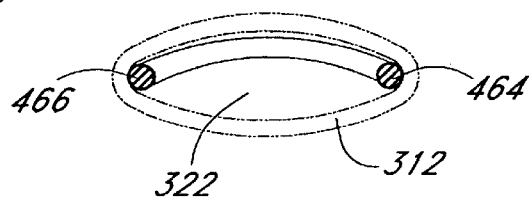

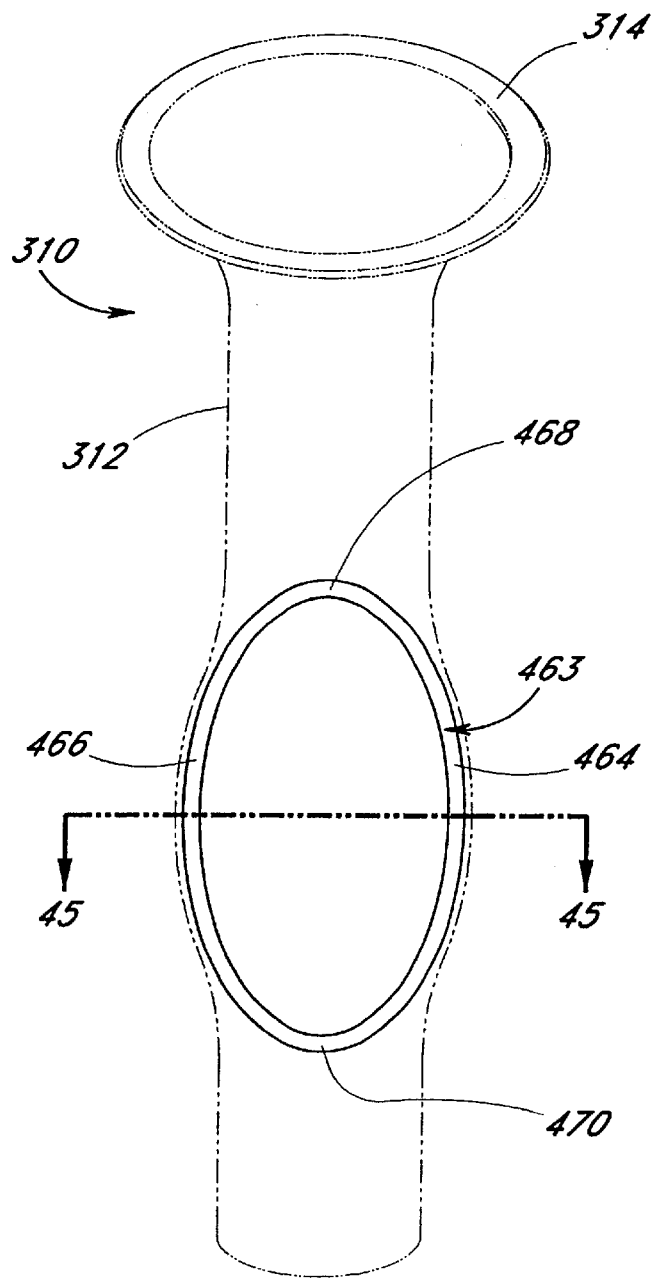
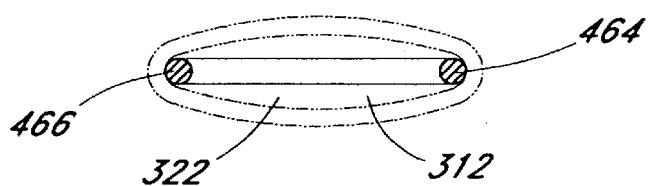

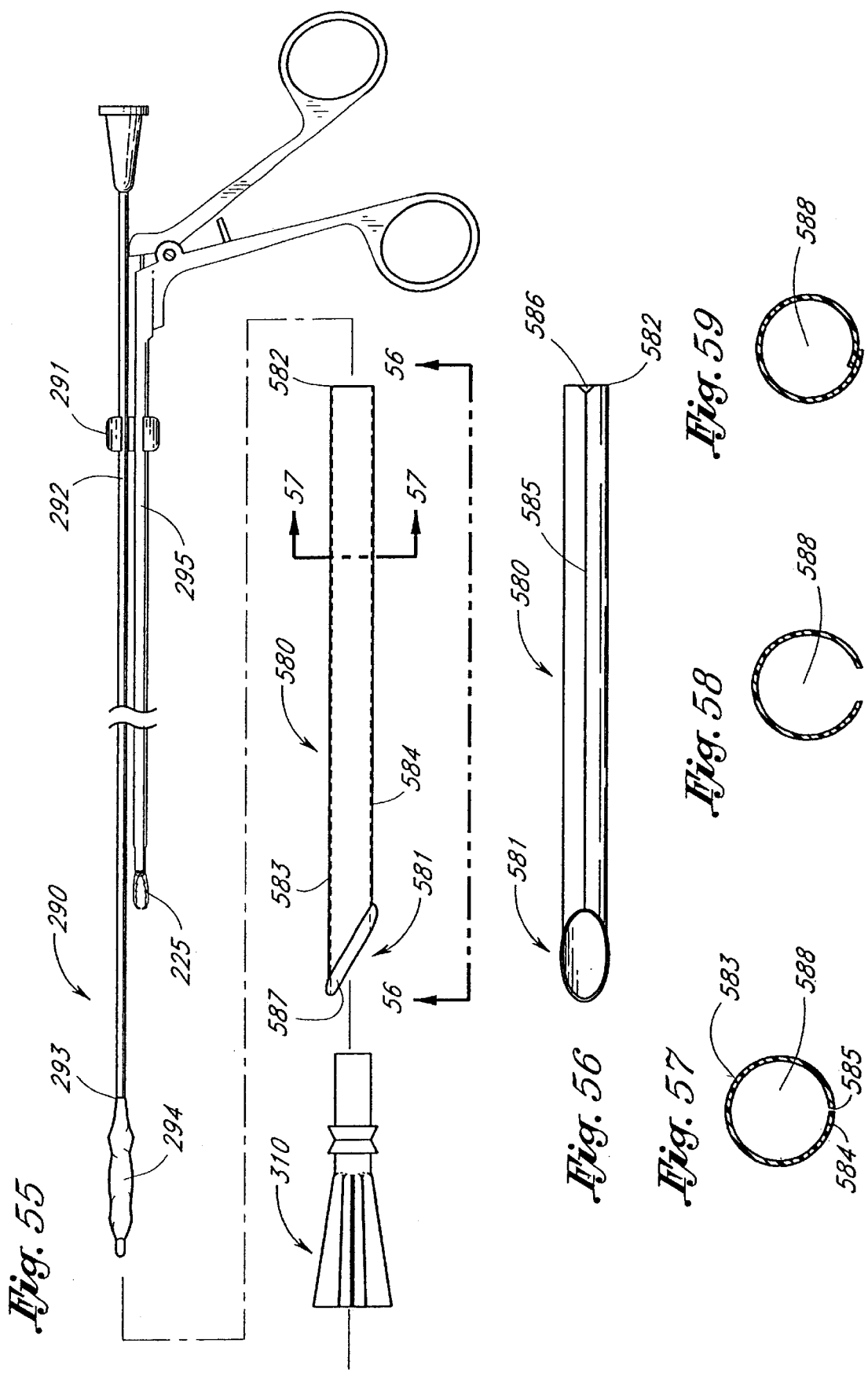

Fig. 66
Fig. 67
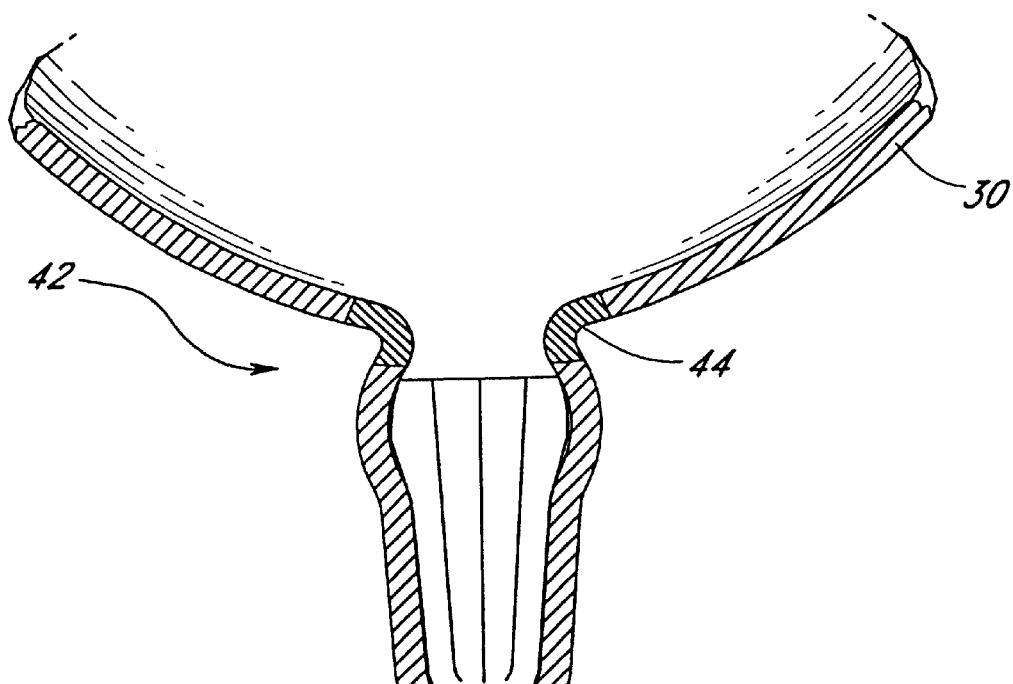
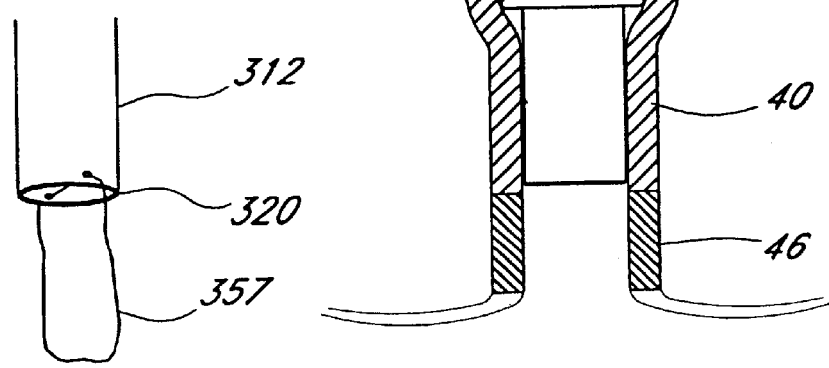

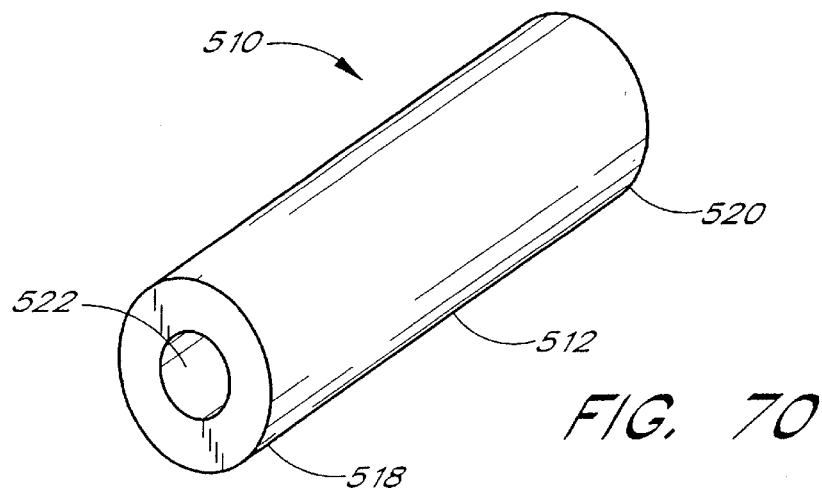
FIG. 70
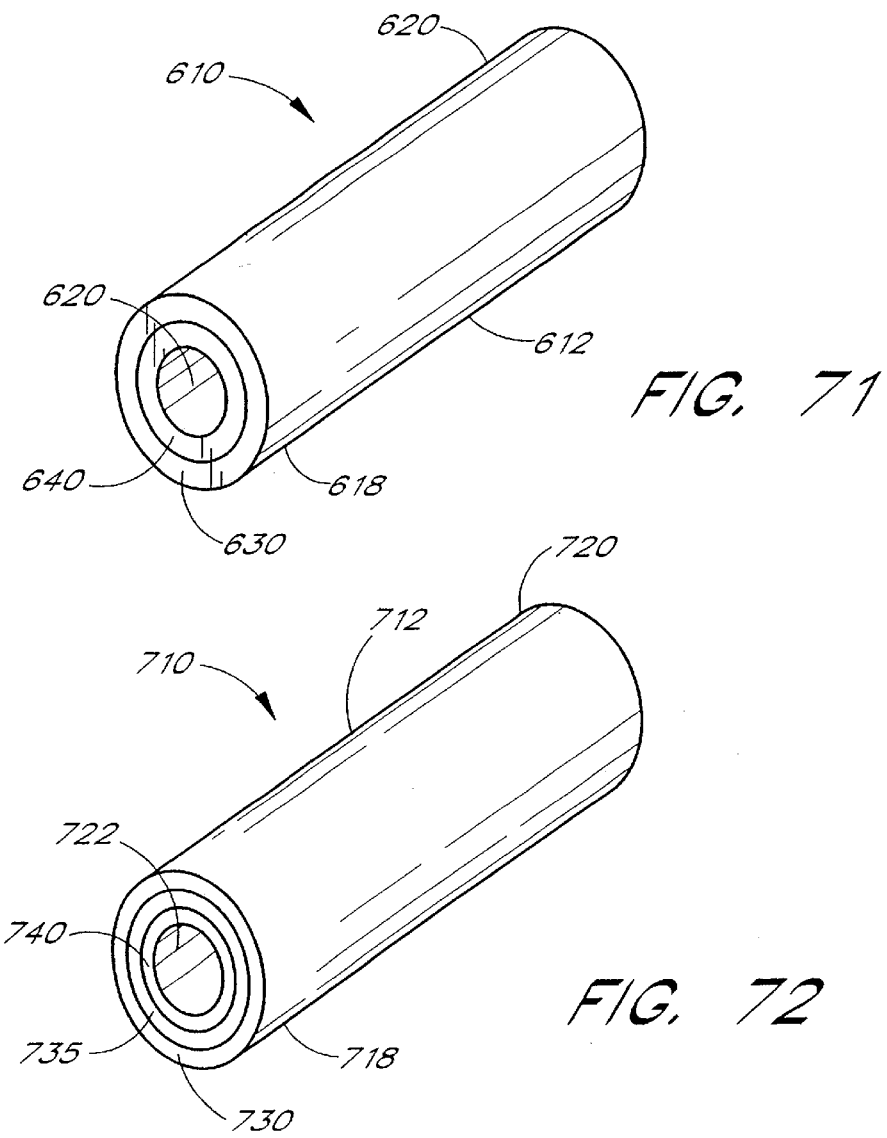
FIG. 71
FIG. 72

BIOADHESIVE MEDICAL DEVICES

CROSS-REFERENCE TO RELATED APPLICATIONS

The present application is a continuation-in-part of application Ser. No. 09/098396 filed Jun. 17, 1998, now U.S. Pat. No. 6,063,119, the entirety of which is incorporated herein by reference.

FIELD OF THE INVENTION

The present invention relates to the field of prosthetic urethral valves or seals for controlling urinary continence. More particularly, the present invention relates to a prosthetic urethral device having an opening pressure that varies in response to changes in physiologic parameters. The present invention also introduces unique cohesive bioadhesive materials which may be used to form prosthetic urethral valves having the aforementioned properties, as well as other biomedical devices.

BACKGROUND OF THE INVENTION

Urinary incontinence is a widespread problem in the United States and throughout the world. Urinary incontinence affects people of all ages and can severally impact a patient both physiologically and psychologically. Urinary incontinence has a number of causes, including birth defects, disease, injury, aging, and urinary tract infection.

In light of the foregoing, a number of attempts have been made to combat urinary incontinence. One such attempt involves the use of a catheter connected to a collection bag with a clamping device on the catheter. Indwelling catheters, however, have a number of drawbacks. For instance, there is an infection risk associated with indwelling catheters, which provide a direct passage for bacteria or other microorganisms into the bladder. Thus, indwelling catheters can only be used for relatively short-term situations. In addition, indwelling catheters and associated collection bags are not cosmetically appealing to most patients.

The prior art prosthetic urethral valves also have numerous disadvantages. For instance, many prior art urethral valves utilize an inflatable cuff around the outside of the urethra. One disadvantage of such a valve is that it requires surgery for installation. In addition, such a valve must be operated externally and thus is dependent on manual intervention. Moreover, the prosthetic urethral valves of the prior art tend to be generally rigid and noncompliant in structure and some tend to dilate the urethra over time. This may result in deterioration of the natural anatomy, which leaves the patient in worse physical condition.

Intraurethral valves of the prior art also generally require manual intervention. Another problem associated with prior art intraurethral valves is that they may be displaced or migrate into the bladder or expelled from the urethra. There is also an infection risk associated with many such valves since they extend into the meatus and/or have portions of the device external to the urethra providing a passage for micro-organisms into the bladder.

Thus, there remains a need for a nonsurgically installed prosthetic urethral valve or seal that responds to physiological conditions and thus can be controlled voluntarily by the patient without manual intervention. Furthermore, there is a need for prosthetic urethral valves having structure or being composed of materials which inhibit valve migration from the urethra into the bladder.

SUMMARY OF THE INVENTION

Advantageously, the present invention provides an intrauretheral valve for controlling urinary incontinence which overcomes many of the shortcomings of the prior art. Valves of the present invention may be introduced nonsurgically, and are formed of novel cohesive bioadhesive materials which nonpermanently bond the valve to the inner lumen of the urethra. Consequently, valves of the present invention are less likely to migrate into the bladder. Furthermore, the bioadhesive compositions used to make the valves may also be used to form all or part of a variety of other biomedical devices.

In one aspect of the present invention, there is provided an intraurethral device for maintaining urinary continence comprising an elongate body having a proximal end, a distal end, and a flow path extending therebetween. The body has an outer surface formed of a bioadhesive material comprising a copolymer resulting from the polymerization of one or more types of carboxyl functional monomers and one or more types of hydrophobic monomers. In some embodiments, the carboxyl functional monomers may be selected from the group consisting of acrylic acid, methacrylic acid, ethyl acrylic acid, propyl acrylic acid, butyl acrylic acid and combinations of the foregoing. The hydrophobic monomers may have a phenyl ring moiety, and in certain embodiments, be selected from the group consisting of phenyl ethyl methacrylic acid, phenyl ethyl acrylic acid, phenyl methyl methacrylic acid, phenyl methyl acrylic acid, benzyl acrylic acid, benzyl methacrylic acid and combinations of the foregoing. Alternatively, the hydrophobic monomer may comprise one or more (meth-)acrylimide monomers.

In one preferred embodiment, the volume ratio of carboxyl functional monomers to hydrophobic monomers in the reaction used to make the copolymer is initially between about 20:1 and 1:2, more preferably between about 10:1 and 1:1, and optimally between about 10:2 and 10:4.

The intraurethral device may also have an inner surface defining the central lumen, the inner surface being formed of a soft polymeric material having a Young's modulus between 1 KPa and 10 MPa, and preferably having a Young's modulus of between 10–100 KPa. In one aspect of this embodiment, there is a middle layer between the outer surface and the inner surface. The middle layer may be formed of an elastomeric material or material having elastomeric properties. Thus, the middle layer may be optionally formed from a material selected from the group consisting of silicone, polyurethane and polyacrylate elastomers.

In another aspect of the present invention, there is provided an intraurethral device for maintaining urinary continence, comprising a three-layered elongate body with a proximal end, a distal end, and a flow path extending therebetween. The three-layered body has an outer layer comprising a bioadhesive material, a middle layer comprising an elastomeric material, and an inner layer comprising a soft polymeric material.

In another aspect of the present invention, there is provided a method of adhering a medical device to a tissue surface. The method comprises providing a medical device having a bioadhesive surface. The bioadhesive surface is formed as a copolymer from the polymerization of at least a first monomer having a carboxyl functional moiety and at least a second monomer having a hydrophobic moiety. The bioadhesive surface is adhered to the tissue by contacting the bioadhesive surface to the tissue surface.

In another aspect of the present invention, there is provided a method of forming a medical device with a bioadhesive surface. The method comprises copolymerizing at least a first carboxyl functional moiety-bearing monomer with at least a first hydrophobic moiety-bearing monomer to form a bioadhesive copolymer. The copolymer has a tensile strength of at least about 10 psi. The bioadhesive copolymer is provided as a surface combined with a medical device, such the surface remains exposed for adhesion to a tissue.

In another aspect of the present invention, there is provided a bioadherent substrate. The substrate has a surface portion comprising a bioadhesive copolymer which selectively adheres to tissues. The copolymer has a tensile strength of at least 10 psi and transmits at least 80% of the visible light passing through it per millimeter of thickness of the copolymer.

In another aspect of the present invention, there is provided a bioadherent medical device. The bioadhesive medical device has a bioadhesive surface comprising a copolymer having at least one carboxyl functional monomeric unit resulting from copolymerization of a monomer selected from the group consisting of

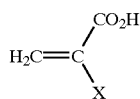

$X=$—H, —$CH_3$, —$CH_2CH_3$ and at least one hydrophobic monomeric unit resulting from copolymerization of a hydrophobic monomer selected from the group consisting of

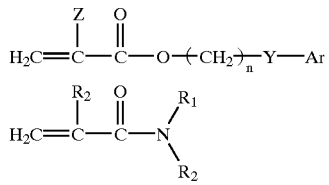

$Z=$—H, —$CH_3$, or —$CH_2CH_3$ $Y=$nothing or O $Ar=C_1$–$C_3$ alkyl substituted aromatic ring or unsubstituted aromatic ring $n=1$–$5$ or $R_1=C_1$–$C_5$ alkyl substituted aromatic ring or unsubstituted aromatic ring $R_2=$hydrogen or $C_1$–$C_5$ alkyl group.

In another aspect of the present invention, there is provided a method of manufacturing a medical device for removable attachment to a tissue surface. The first step of the method is to provide a medical device having at least one tissue contacting surface. A coating is applied to the tissue contacting surface. The coating comprises a polymerization product of at least a first monomer having a carboxyl functional moiety and at least a second monomer having a hydrophobic monomer moiety.

In another aspect of the present invention, there is provided a method of manufacturing a medical device by applying a cohesive bioadhesive to the entire exposed surface of the medical device. Optionally, the medical device and the coating may be impregnated with a drug.

In another aspect of the present invention, there is provided a method of releasably adhering a medical device to a tissue surface. The medical device has a surface thereon comprising an adhesive composition. A site in or on a patient for implantation of the device is then identified. The surface of the medical device is then contacted with tissue at the site to adhere the device to tissue. Preferably, the adhesive surface has a tensile strength in excess of about 10 psi and comprises a homogeneous copolymer capable of providing adhesion to a tissue surface in an aqueous environment. The site may be a body lumen, as for example the esophagus, intestine, urethra, ureter, veins and arteries. The site may be a subcutaneous tissue surface, or the site may be a hollow organ.

Medical devices incorporating the cohesive bioadhesives described above may be used in a variety of clinical applications. For example, the devices may function as facilitating devices, flow regulating devices, monitoring devices, and other types of medical devices requiring adhesion to tissue.

In one application, the medical device is a plug for reducing the available volume of a vascular anomaly, such as for treatment of vascular aneurysm or arteriovenous fistula.

In a different application, medical devices incorporating bioadhesives of the present invention may be applied to the surface of an organ, as for example, for treatment of an ulceration in the surface of the organ.

Optionally, medical devices incorporating the bioadhesives of the present invention may be used to release a medication from the medical device into the site. In these and other applications, the medical device may be adhered to the site for a period of time within the range of from about 1 to about 30 days. In some circumstances, the medical device might be absorbed at the site.

In another application of the present invention, there is provided a drug delivery device for the time release of a drug into adjacent tissue. The device comprises the polymerization product of at least a first monomer have a carboxyl functional moiety and at least a second monomer having a hydrophobic moiety, and at least one drug.

In another application of the present invention, there is provided a wound closure patch, such as for closing a subcutaneous aperture or surgical incision, comprising the polymerization product of at least a first monomer having a carboxyl functional moiety and at least a second monomer having a hydrophobic moiety. The patch may be in the form of a flexible sheet.

In another application of the present invention, there is provided a vascular plug for obstructing blood flow through a vessel, comprising a radially outwardly facing annular surface having thereon a polymerization product of at least a first monomer having a carboxyl functional moiety and at least a second monomer having a hydrophobic moiety.

BRIEF DESCRIPTION OF THE DRAWINGS

FIG. 13 illustrates the valve assembly of FIG. 12 during a hypermobility event.

FIG. 14 is a cross-sectional view taken along line 14—14 of FIG. 12.

FIG. 15 is a cross-sectional view taken along line 15—15 of FIG. 13.

FIG. 21 is a perspective view of an alternate embodiment of the device according to the present invention.

FIG. 22 is a top view of the embodiment depicted in FIG. 21.

FIG. 23 is an elevational side view of the embodiment depicted in FIG. 21.

FIG. 23A is an elevational side view of an alternate embodiment of the device depicted in FIG. 23.

FIG. 24 is a bottom view of the embodiment depicted in FIG. 21.

FIG. 25 is a cross-sectional view taken along line 25—25 of FIG. 22.

FIG. 26 is a cross-sectional view of an alternate embodiment of the device illustrated in FIG. 25.

FIG. 27 is a cross-sectional view taken along line 27—27 of FIG. 25.

FIG. 28 is a cross-sectional view of an alternate embodiment of the device illustrated in FIG. 25 showing an alternate shaped tubular body.

FIG. 29 is a cross-sectional view of an alternate embodiment of the device illustrated in FIG. 25 showing an alternate shaped tubular body.

FIG. 30 is a cross-sectional view of an alternate embodiment of the device illustrated in FIG. 25 showing an alternate shaped and variable stiffness tubular body in a closed position.

FIG. 31 is a cross-sectional view of an alternate embodiment of the device illustrated in FIG. 25 showing an alternate shaped and variable stiffness tubular body in an open position.

FIG. 35 is a perspective view of an alternate embodiment of the device according to the present invention.

FIG. 36 is a top view of the embodiment depicted in FIG. 35.

FIG. 37 is an elevational side view of the embodiment depicted in FIG. 35.

FIG. 38 is a bottom view of the embodiment depicted in FIG. 35.

FIG. 41 is a frontal perspective view of an alternate embodiment of the present invention showing a resilient support structure inserted in the lumen of a device which is shown in phantom.

FIG. 42 is a cross-sectional view taken along line 42—42 of FIG. 41.

FIG. 43 is a side view of the resilient support structure depicted in FIG. 41.

FIG. 44 is a frontal perspective view of an alternate embodiment of the device illustrated in FIG. 41.

FIG. 45 is a cross-sectional view taken along line 45—45 of FIG. 44.

FIG. 55 is an exploded side view showing a device for maintaining urinary continence, an introducer, and a balloon catheter coupled to grasping forceps.

FIG. 56 is a bottom view of the introducer taken along line 56—56 of FIG. 55.

FIG. 57 is a cross-sectional view of the introducer taken along line 57—57 of FIG. 55.

FIG. 58 is a schematic cross-sectional view showing the introducer in an expanded configuration.

FIG. 59 is a schematic cross-sectional view showing the introducer in a contracted or overlapping configuration.

FIG. 66 is a schematic cross-sectional view showing the device for maintaining urinary continence positioned in the urinary tract of the patient.

FIG. 67 is a perspective end view showing a tether attached to the distal end of a tubular body of the device for maintaining urinary continence.

FIG. 70 is a perspective view of a single layer bioadhesive device for maintaining urinary continence.

FIG. 71 is a perspective view of a two-layered bioadhesive device for maintaining urinary continence.

FIG. 72 is a perspective view of a three-layered bioadhesive device for maintaining urinary continence.

DETAILED DESCRIPTION OF THE PREFERRED EMBODIMENT

Figure 1:
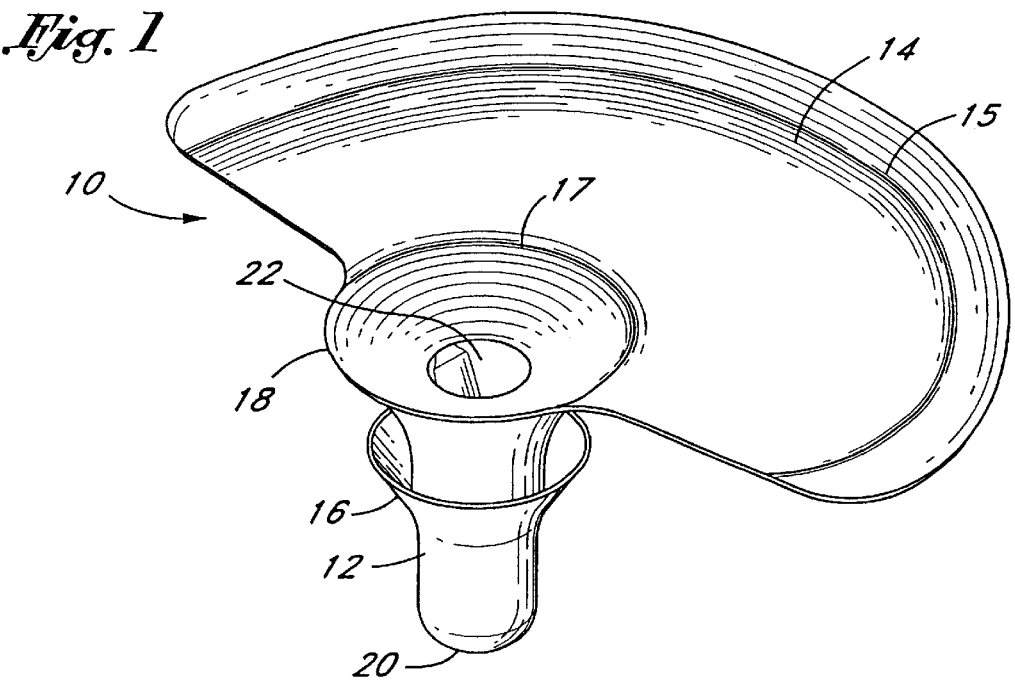
FIG. 1 is a perspective view of one embodiment of the prosthetic urethral valve according to the present invention.
Figure 2:
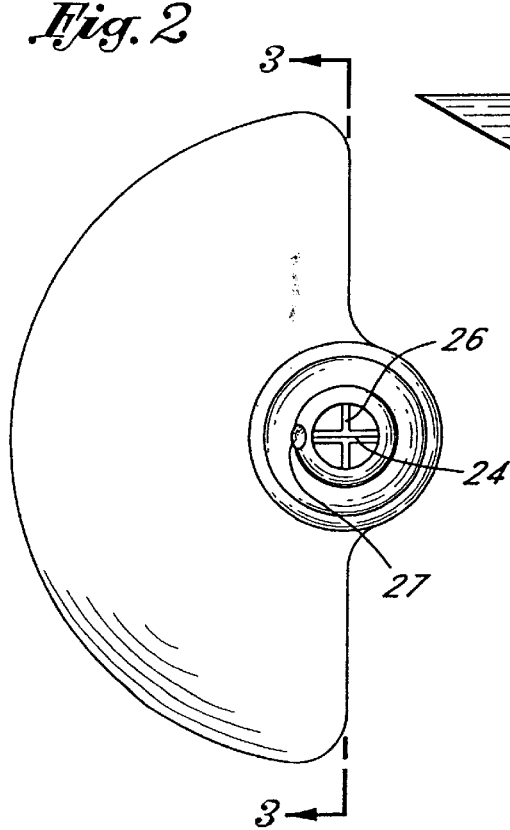
FIG. 2 is a bottom view of the valve depicted in FIG. 1.

Referring to FIG. 1, there is disclosed a perspective view of the prosthetic urethral valve assembly 10 of the present invention. The valve assembly includes a tubular body 12 having a proximal end 18, a distal end 20, and a central lumen 22 extending therethrough. As illustrated in FIG. 2, a gripping tab or boss 27 is preferably included at the distal end 20 of tubular body 12 to facilitate transurethral placement of the valve, which is discussed in more detail below.

Figure 4:
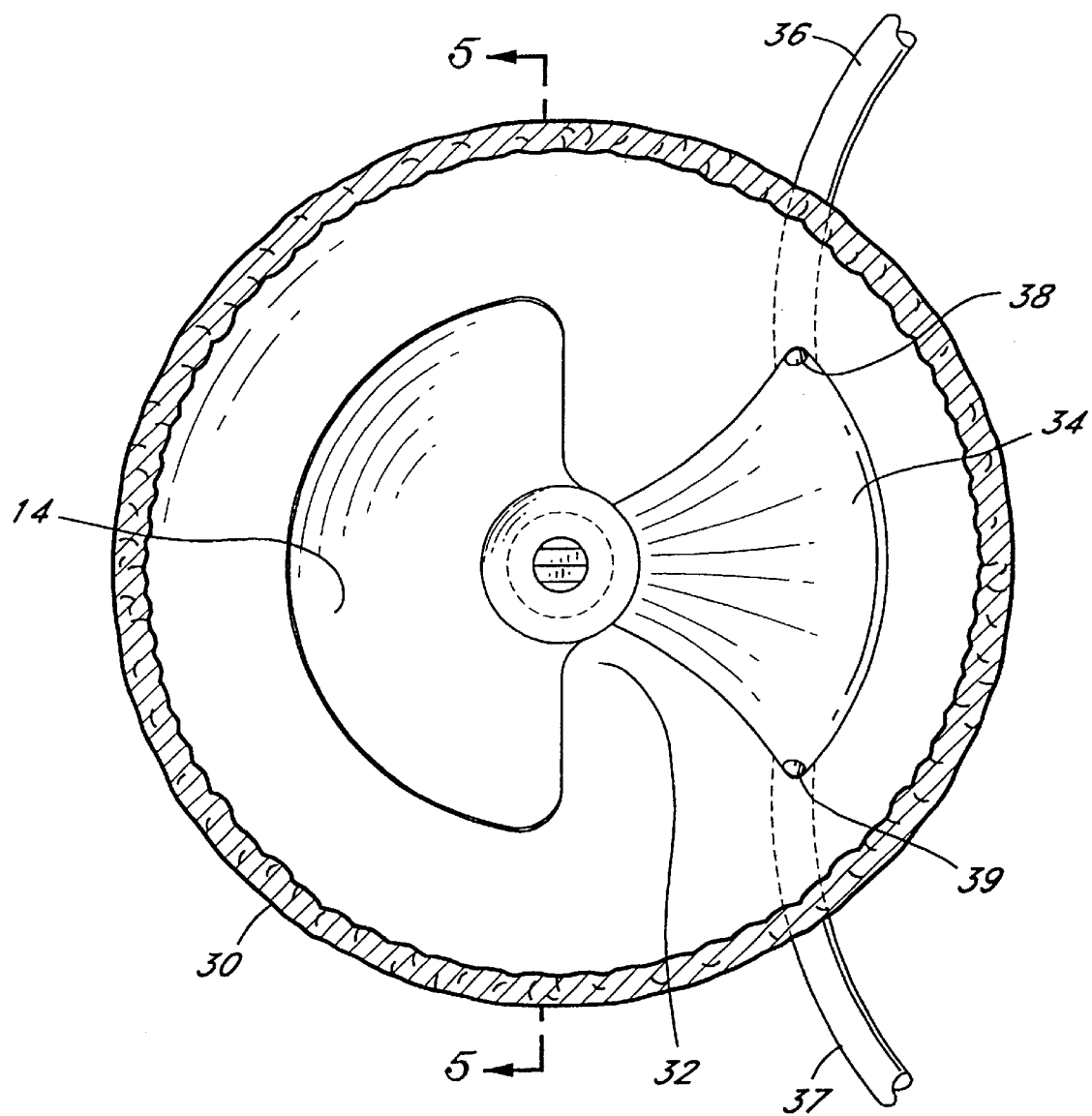
FIG. 4 is a transverse cross-sectional view through the bladder showing a top view of the device positioned in the bladder.
Figure 5:
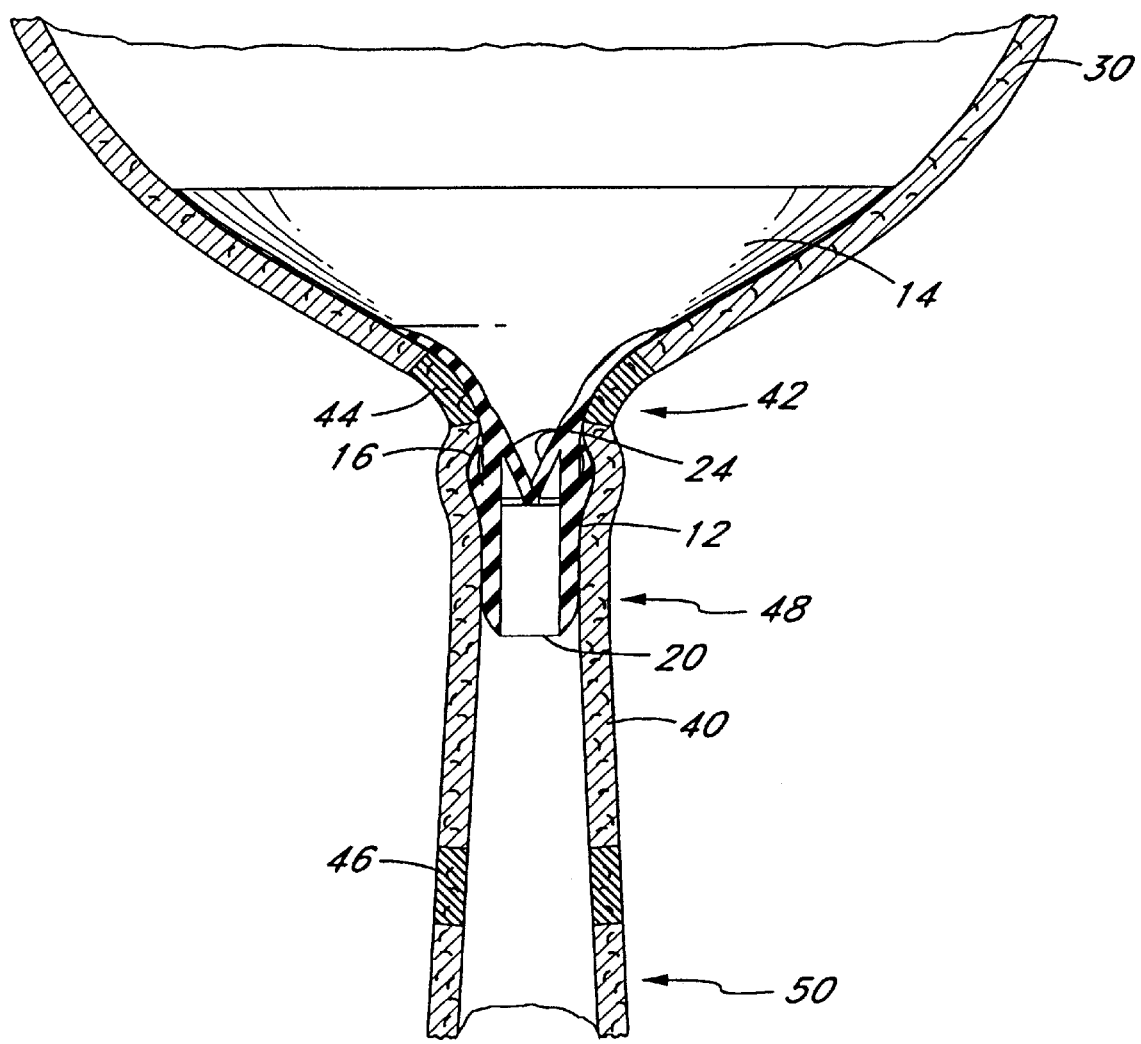
FIG. 5 is an elevational cross-sectional view taken along line 5—5 of FIG. 4.

The valve assembly 10 also includes a first anchor 14. The first anchor preferably conforms to a portion of a base 32 of a bladder 30 as illustrated in FIGS. 4 and 5. The first anchor 14 functions to releasably secure the valve assembly 10 relative to the bladder 30 and the urethra 40, while preferably avoiding contact with the trigone 34 of the bladder 30. The first anchor 14 also helps prevent urine from escaping around the exterior of the device.

The trigone 34, illustrated in FIG. 4, is a triangular area of the bladder located between the urethra 40 and the two ureteric orifices 38 and 39. The ureteric orifices 38 and 39 drain urine from the ureters 36 and 37, respectively. Minimizing or avoiding contact between the first anchor 14 and the trigone 34 is desirable because the trigone contains a nerve bed which can be stimulated by tactile means resulting in an undesirable sense of urinary urgency.

In light of the foregoing considerations, the first anchor is preferably an atraumatic retention structure which is enlargeable from a first, collapsed configuration for transurethral placement to a second, enlarged configuration for resisting distal migration out of the bladder and into the urethra. In the illustrated embodiment, the first anchor comprises a pliable semiconical retention flap that inclines generally radially outwardly in the proximal direction from the proximal end 18 of the tubular body 12 as illustrated in FIG. 1. The retention flap is mechanically biased in the direction of the second, enlarged configuration as illustrated to help prevent the valve assembly 10 from being expelled distally from the urethra 40. The proximal surface of the first anchor 14 is exposed to the intravesical pressure of the bladder, which helps prevent the valve assembly 10 from being dislodged proximally into the central portion of the bladder.

In most patients, the trigone extends circumferentially approximately 60° to 90°. Thus, if properly placed within the bladder, the first anchor 14 can extend circumferentially up to as much as from approximately 270° to 300° and still avoid contacting the trigone. Preferably, the first anchor extends circumferentially either continuously or intermittently through an angle of approximately 100° to 180° in order to account for potential human error during placement, yet still provide an adequate surface area to achieve the anchoring function described above. In some embodiments, the construction material of the first anchor 14 is such that the anchoring function can be achieved with circumferential extension of less than about 100°.

A number of structures can be used to minimize either the circumference or the total contact area of the first anchor 14 yet still provide for adequate anchoring. For example, circumferentially extending reinforcing rings 15 and/or 17, such as a fine gauge spring wire may be incorporated into the valve assembly. The use of spring wires would provide a bias in the direction of the second, enlarged configuration while permitting a reduction in the size and mass of the anchor. Spring wires can alternatively extend in planes that are generally parallel to the longitudinal axis of the tubular body 12. Wires can be integrally molded into the anchor 14. Spring bias can also be optimized simply by adjusting the wall thickness of the anchor 14 and through appropriate materials choice.

In addition, as will be apparent to one of ordinary skill in the art, a variety of other structures could be used to accomplish the function of first anchor 14. For instance, the first anchor 14 may comprise a series of discontinuous, mechanically biased flexible struts extending from the proximal end 18 of the tubular body 12. Typically, two or three or more struts would be used. Alternatively, spring biased hinged anchors could be used to releasably secure the valve assembly 10 relative to the bladder 30 and the urethra 40.

In addition to the first anchor 14, preferably the valve assembly 10 also includes a second anchor 16. The second anchor 16 also helps to releasably secure the valve assembly 10 relative to the bladder 30 and the urethra 40. In addition, the second anchor 16 helps to stabilize the tubular body 12 within the urethra, especially in a patient having a large diameter urethra.

In the illustrated embodiment, the second anchor 16 is an annular flange attached to the tubular body 12 at a point between the proximal end 18 and the distal end 20. As illustrated in FIG. 1, the second anchor ramps radially outwardly in the proximal direction, thereby providing a mechanical bias against proximal dislodgment of the tubular body into the bladder. Optionally, one or more nitinol rings can be molded into the annular flange. After insertion of the valve assembly, expansion of the nitinol rings or other resilient support structures in response to body temperature provides an additional mechanical bias to help further secure the valve assembly.

As will be apparent to one of ordinary skill in the art, a variety of structures other than the proximally extending annular flange described above could be used to accomplish the function of second anchor 16. For instance, a variety of radially extending preferably atraumatic structures, such as semi-spheres, ridges or barbs can be attached to or integrally molded with the tubular body 12. Proximally and/or distally extending suture ends attached to the tubular body 12 using well known methods can also be used to accomplish the function of the second anchor 16.

Figure 3:
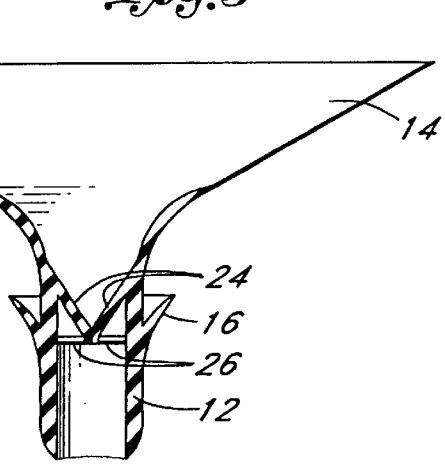
FIG. 3 is an elevational cross-sectional view taken along line 3—3 of FIG. 2.

The valve assembly 10 also includes a valve 24, such as a duckbill valve, which is preferably located within the fluid flow path through tubular body 12 between the proximal end 18 and the distal end 20. As illustrated in FIG. 3, optional valve supports 26 can also be included in the present invention to increase the opening pressure of the valve, if necessary, based on the characteristics of the material and dimensions used to construct the valve assembly 10.

The function of the valve is to assist normal physiological mechanisms to regulate the flow of urine through the tubular body 12. When the valve 24 is in an open position, the tubular body provides a fluid communication path between the bladder 30 and the urethra 40. When the valve is in the open position, preferably a flow rate of approximately 5–15 cc per second is achieved when the pressure differential on the valve is between approximately 20–30 cmH$_2$O. When the valve is in a closed position, the valve assembly 10 provides a seal preventing incontinence.

Figure 49:
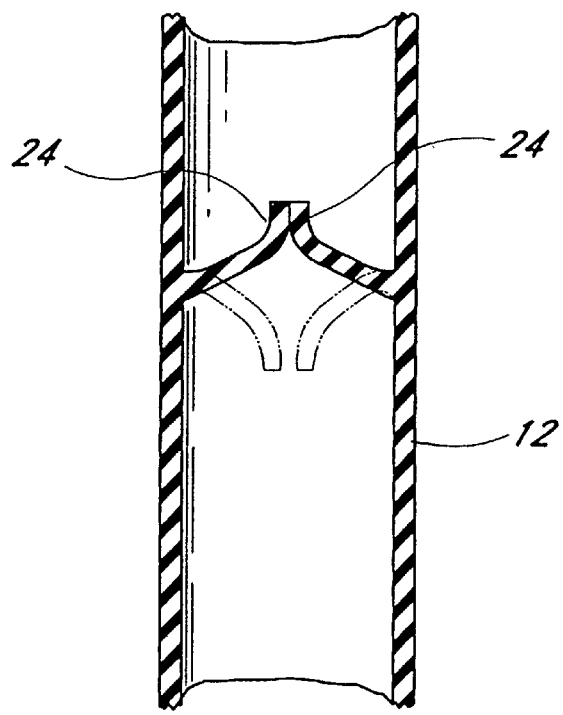
FIG. 49 is a schematic elevational cross-sectional view showing a collapsible duckbill valve in a closed position. The open position of the valve is shown in phantom.

A variety of structures other than the duck bill valve described above could be used to accomplish the function of the valve 24. For instance, the valve 24 could comprise a collapsible duckbill valve such as that illustrated in FIG. 49. In FIG. 49, the valve 24 is shown in both the open and closed positions, the open position being shown in phantom. One advantage of the valve 24 illustrated in FIG. 49 is that it has a relatively high opening pressure above which little resistance to flow is encountered.

Figure 50:
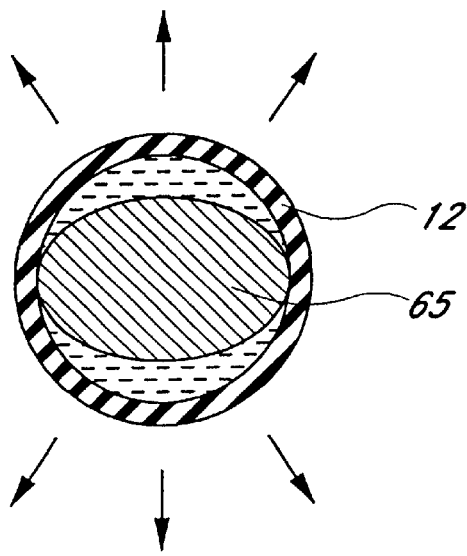
FIG. 50 is a schematic cross-sectional view showing an alternate embodiment of a valve-like structure of the present invention in an open position.
Figure 51:
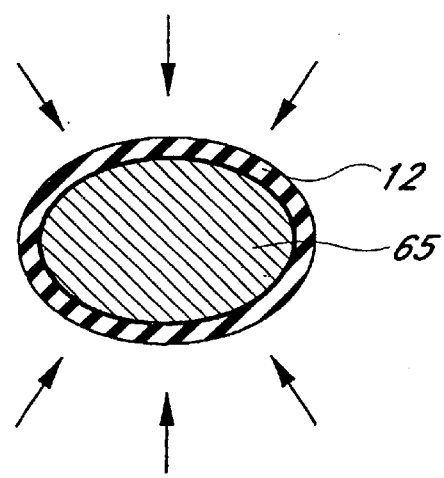
FIG. 51 is a schematic cross-sectional view showing the valve-like structure of FIG. 50 in a closed position.

In addition, a valve-like function could be achieved as illustrated in FIGS. 50–51 in which a solid rod-like structure 65 is placed within the tubular body 12. The rod-like structure 65 is preferably oval as illustrated in FIGS. 50–51. In its open state, the diameter of the tubular body 12 is larger than that of the rod 65. Using conventional techniques such as thermal bonding, solvent bonding or suitable adhesives known in the art, the tubular body 12 is secured to the rod 65 preferably along the length of the rod 65 at least two points as illustrated in FIG. 50.

During bladder filling, the urethra exerts radially inwardly directed forces on the tubular body 12 which keep the tubular body 12 sealed against the rod 65 as illustrated in FIG. 51, thereby maintaining continence. During micturition, however, the pressure exerted by the urethra decreases allowing radial expansion of the tubular body 12 to its open position as illustrated in FIG. 50.

Figure 52:
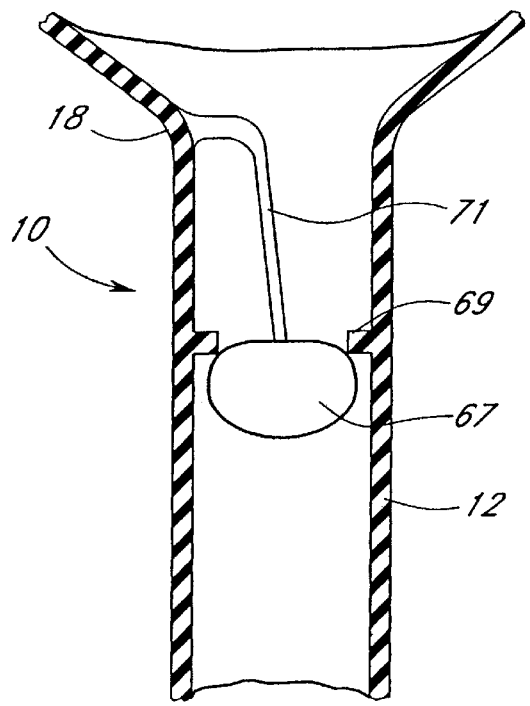
FIG. 52 is a schematic elevational cross-sectional view showing a tethered ball type valve in a closed position.
Figure 53:
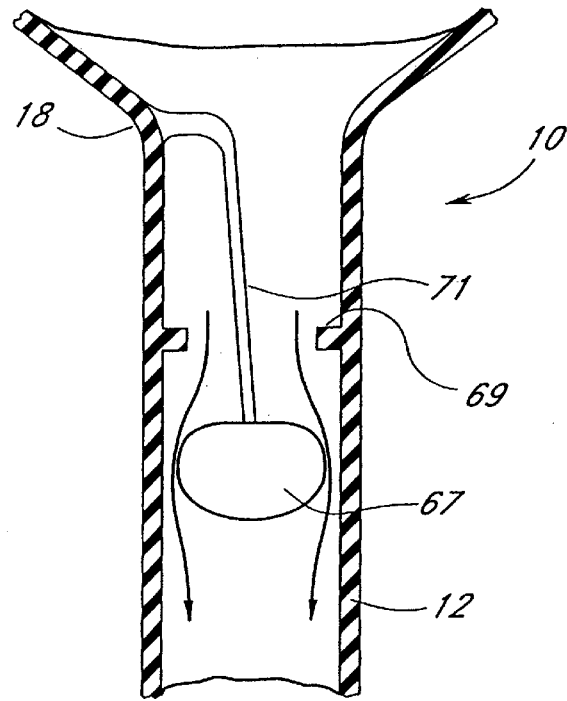
FIG. 53 shows the valve of FIG. 52 in an open position.

The function of the valve 24 could also be accomplished using a tethered ball type valve as illustrated in FIGS. 52–53. When the valve is in the closed position, the ball portion 67 of the valve preferably rests against an inwardly projecting extension 69 of the tubular body 12 as illustrated in FIG. 52. The ball portion 67 of the valve is attached to an elastomeric tether 71. As will be apparent to one of ordinary skill in the art, the tether 71 can be attached at a variety of places on the valve assembly 10, such as the proximal end 18 of the tubular body 12 as illustrated in FIGS. 52–53. FIG. 53 shows the valve in the open position.

Figure 54:
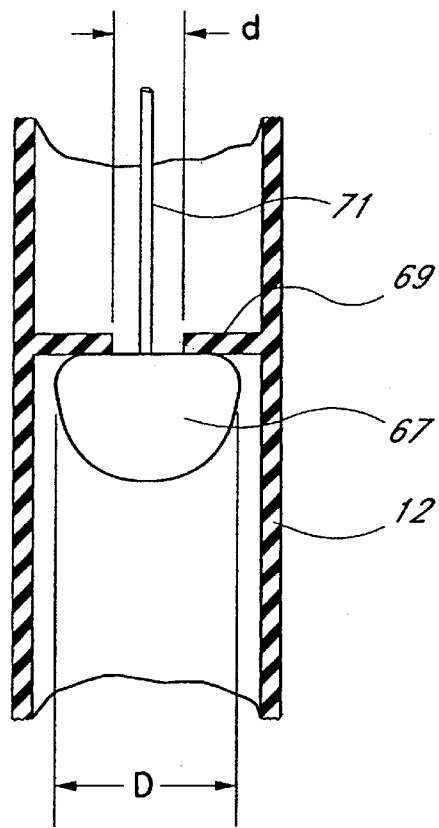
FIG. 54 is an alternate embodiment of the valve illustrated in FIGS. 52 and 53.

FIG. 54 illustrates an alternative embodiment of the tethered ball type valve. In accordance with this embodiment, when the valve is in the closed position the area of fluid in contact with the ball portion 67 of the valve has a diameter "d" which is less than the diameter "D" of the ball portion 67 of the valve. Because the area of fluid in contact with the ball portion 67 of the valve in the closed position is less than the area of fluid in contact with the ball portion 67 of the valve when the valve is in the open position, the pressure required to open the valve is more than the pressure required to keep the valve in the open position. Thus, little resistance to flow is encountered after the opening pressure is achieved.

As will be apparent to one of ordinary skill in the art, a variety of structures other than the valves described above could be used to accomplish the function of the valve 24. For instance, the valve 24 could comprise a trap door type valve with an integral elastomeric return spring hinge or tether. Such a valve preferably has a relatively high opening pressure, such as from about 5–80 cmH$_2$O, and more preferably from about 5–20 cmH$_2$O, above which little resistance to flow is encountered. A multi-leaflet valve having struts to control baseline pressure or a puppet type valve having an integral elastomeric spring could also be used to accomplish the function of valve 24.

For convenience, the valves described above were discussed with reference to valve assembly 10. One of ordinary skill in the art will recognize, however, that the valves described above can also be used with other embodiments of the present invention described in the subject application.

The opening pressure of the valve 24 depends on the type of valve chosen and the etiology of the patient's incontinence. The opening pressure of the valve, prior to being positioned within the patient, ranges from approximately 2–100 cmH$_2$O, more preferably from approximately 5–20 cmH$_2$O, and most preferably from approximately 5–10 cmH$_2$O. As discussed below, however, after the valve is properly positioned within the patient, the opening pressure of the valve varies in response to physiologic parameters.

Referring to FIG. 5, an elevational cross-sectional view of the valve assembly is shown positioned relative to the bladder 30 and the urethra 40. The urethra 40 is diagrammatically divided into a proximal portion 48 and a distal portion 50. An internal urethral sphincter 44 and an external urethral sphincter 46 are also schematically shown. As illustrated in FIG. 5, the distal end 20 of tubular body 12 is located within the proximal portion 48 of the urethra 40 between the internal urethral sphincter 44 and the external urethral sphincter 46. Preferably, the valve 24 is also located in the proximal portion 48 of the urethra, although it can alternatively be positioned elsewhere along the flow path between the bladder 30 and the distal end 20 of the valve assembly 10. Optionally, a radiopaque material, such as gold, tantalum, or barium sulfate can be incorporated into the valve to ensure proper positioning. Preferably, the radiopaque material is incorporated as a visualization ring into the distal end 20 of the tubular body 12.

Figure 6:
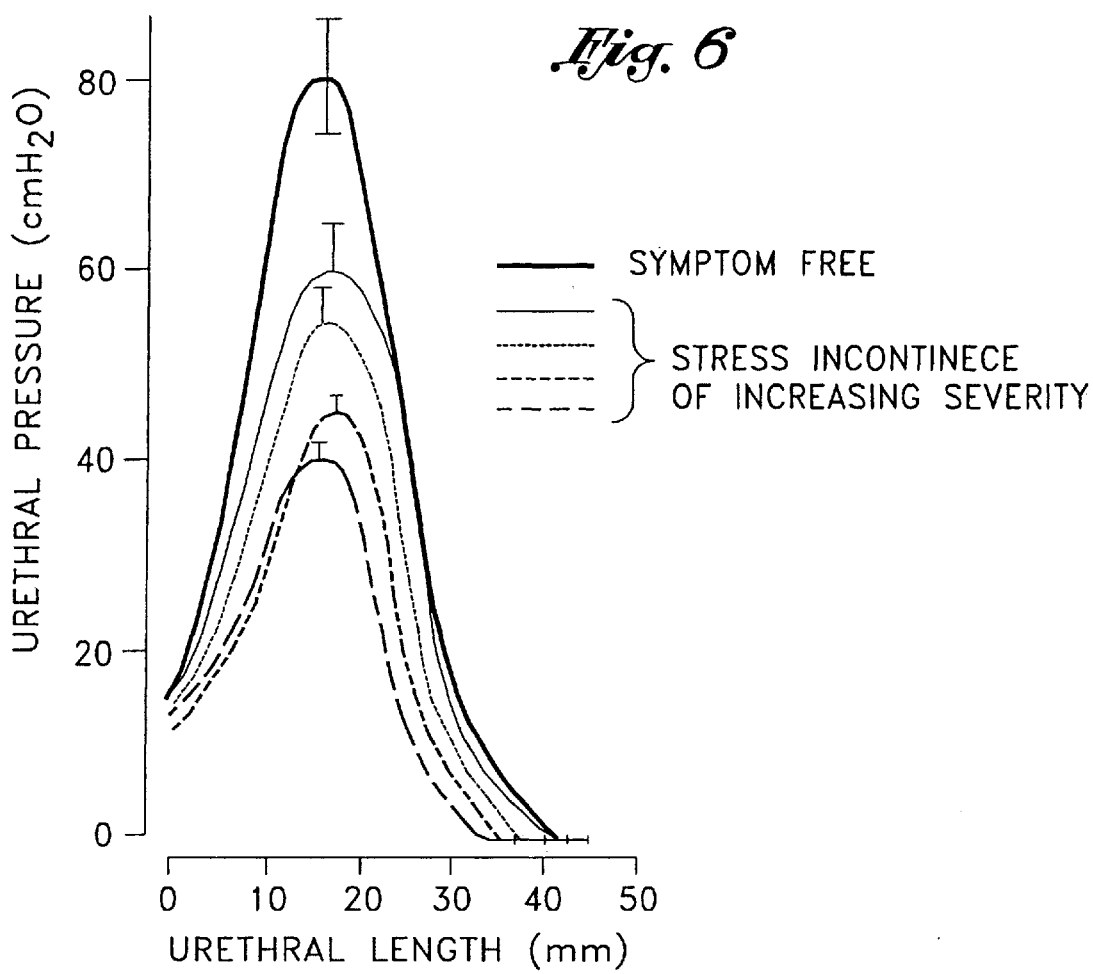
FIG. 6 graphically depicts the relationship between urethral pressure and urethral length in a group of symptom-free women and four groups with stress incontinence of varying severity.

Although knowledge of the physiology of the bladder and the urethra is incomplete, the external urethral sphincter is believed to be located approximately 1.0 to 4.0 cm, and more typically approximately 1.5 to 2.5 cm, distal to the bladder neck 42 in women, and approximately 5.0 to 6.0 cm distal to the bladder neck 42 in men. The external urethral sphincter is believed to primarily be responsible for the urethral pressure profile illustrated in FIG. 6. As can be seen in FIG. 6, urethral pressure is highest approximately 2 cm distal to the bladder neck. The inventors believe that in some instances the top portions of the curves illustrated in FIG. 6 may extend over a larger range of urethral length. In order to fully take advantage of the urethral pressure gradient, the valve 24 and the tubular body 12 preferably do not extend distal to the external urethral sphincter. More preferably, the tubular body 12 extends less than or equal to about 2.0 cm distal to the bladder neck. The relatively short length of the tubular body 12 allows the valve to be maximally exposed to the urethral pressure gradient, thereby aiding in keeping the valve 24 closed while the bladder is filling. During micturition, however, the urethra relaxes, removing this back pressure or closing pressure and aiding in the voiding process.

Figures 7A, 7B:
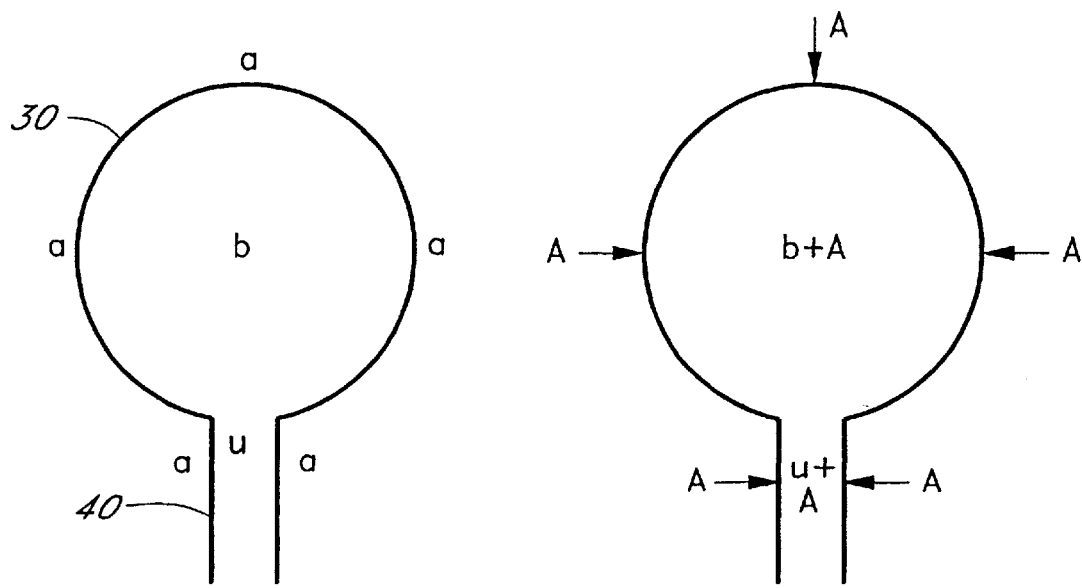
FIGS. 7A and 7B diagrammatically represent the bladder, the urethra, and various pressures relating to urinary tract physiology.

The urethral pressure gradient described above, also aids the valve assembly 10 in maintaining urinary continence during changes in physiologic parameters, such as increases in abdominal pressure caused by coughing. This aspect of the present invention is illustrated diagrammatically in FIGS. 7A and 7B. In FIGS. 7A and 7B, "a" equals resting intra-abdominal pressure, "b" equals resting bladder pressure, "u" equals resting urethral pressure, and "A" equals abdominal pressure rise on coughing. As can be seen in FIG. 7B, an increase in abdominal pressure increases both the bladder pressure and the urethral pressure. Because of the relatively short tubular body 12 of the present invention, however, the increase in urethral pressure caused by the increase in abdominal pressure is transmitted to the distal side of the valve 24, thereby momentarily increasing the effective opening pressure of the valve to help maintain valve closure during the increase in abdominal pressure.

In addition to the urethral pressure gradient described above, the bladder neck and the urethra also exert an inwardly directed force, which can enhance the function of the valve assembly 10 of the present invention. For instance, during bladder filling, the urethra exerts inwardly directed forces on the tubular body 12 and the valve 24, which help to keep the valve closed during the filling phase.

Conversely, during micturition, the pressure exerted by the bladder neck and the urethra decreases, thereby decreasing the radial or compressive force exerted on the tubular body and the valve. This decrease in radial or compressive force lowers the opening pressure of the valve and thus facilitates opening of the valve during micturition. Thus, although any of a variety of valve structures can be utilized in the valve assembly 10, valve structures which exhibit an increased opening pressure in response to inward compressive forces or radially inward compression are often preferred.

In contrast to the relatively short valve assembly 10 of the present invention, prosthetic urethral valve devices that extend into the meatus and/or have portions of the device external to the body are unable to take advantage of the urethral pressure gradient and radial forces described above.

Another advantage of the relatively short length of the valve assembly of the present invention is that it minimizes the risk of infection. In contrast, prosthetic urethral valve devices that extend into the meatus and/or have portions of the device external to the body provide a direct path for bacteria and other microorganisms to enter the urinary tract.

Figure 8:
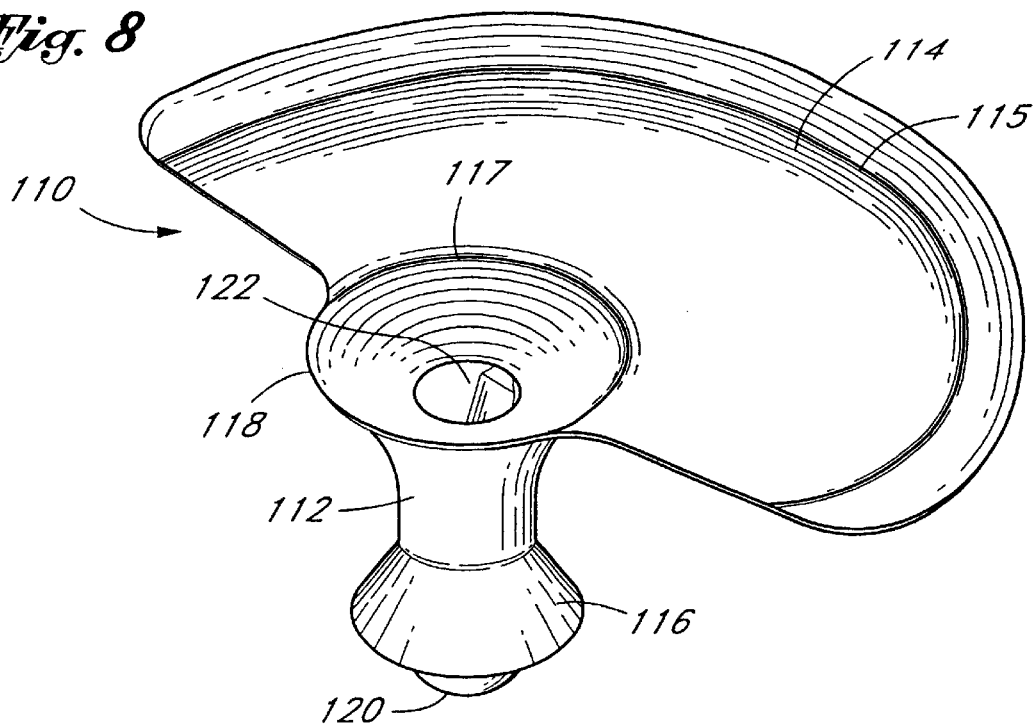
FIG. 8 is a perspective view of an alternate embodiment of the prosthetic urethral valve according to the present invention.

Referring to FIGS. 8–15, there is shown an alternate embodiment of the valve assembly of the present invention. As illustrated in FIG. 8, the valve assembly 110 includes a tubular body 112 having a proximal end 118, a distal end 120 and a central lumen 122 extending therethrough. The valve assembly also includes a first anchor 114, a gripping boss 127, and reinforcing rings 115, 117.

In addition to the first anchor 114, preferably the valve assembly 110 also includes a second anchor 116. The illustrated second anchor 116 is an annular flange attached to the tubular body 112 at a point between the proximal end 118 and the distal end 120 of the tubular body. As illustrated in FIG. 8, the second anchor of the alternate embodiment preferably inclines distally from tubular body 112, thereby providing a mechanical bias against distal dislodgment of the valve assembly from the patent.

Figure 9:
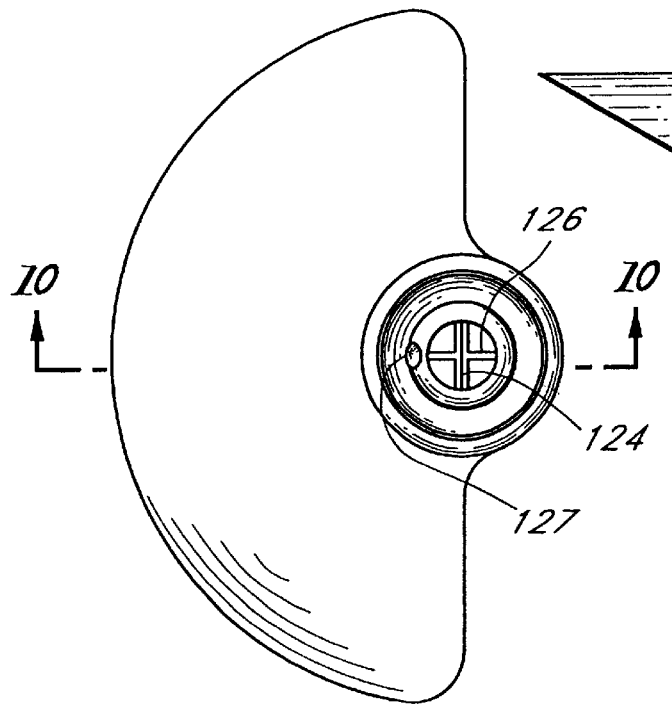
FIG. 9 is a bottom view of the valve depicted in FIG. 8.
Figure 10:
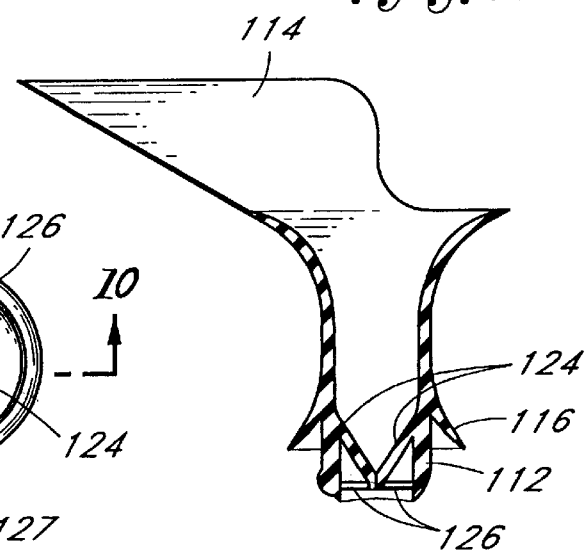
FIG. 10 is an elevational cross-sectional view taken along line 10—10 of FIG. 9.
Figure 11:
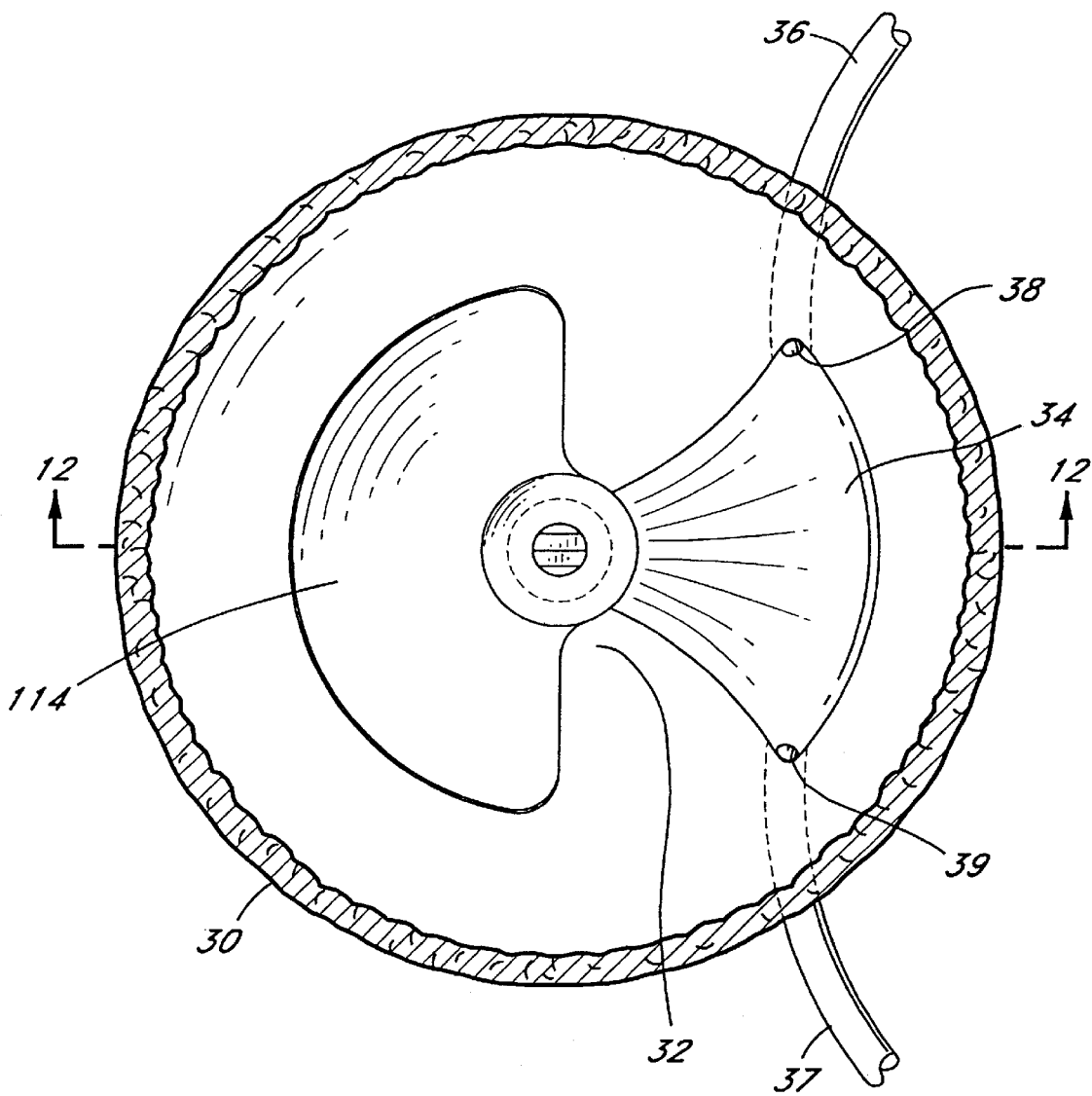
FIG. 11 is a transverse cross-sectional view through the bladder showing a top view of the alternate embodiment of the device positioned in the bladder.

The valve assembly 110 also includes a valve 124, such as a duckbill valve, which is preferably located within the lumen 122 of tubular body 112 between the proximal end 118 and the distal end 120 of the tubular body. As illustrated in FIG. 9, the orientation of valve 124 is preferably rotated approximately 90° relative to the valve depicted in FIG. 2. Thus, the coaptive edges of the two duckbill leaflets extend side to side when the valve is properly positioned in the patient. In addition, as illustrated in FIG. 10, optional valve supports 126 can be included to increase the opening pressure of the valve, if necessary, based on the characteristics of the material used to construct the valve assembly 110.

The length of the tubular body 112 of the valve assembly of the alternate embodiment is approximately the same as that of the valve assembly of FIGS. 1–5. As illustrated in FIG. 10, however, the distance between the valve 124 and the proximal end of the tubular body 112 of the alternate embodiment is greater than the distance between the valve 24 and the proximal end of the tubular body 12 of the valve assembly 10 illustrated in FIG. 3. Preferably the distance between the valve 124 and the proximal end of the tubular body is approximately 1.0–3.0 cm in the alternative embodiment, compared to approximately 0.5–2.0 cm in the embodiment of the valve 24 depicted in FIG. 3. The increased distance between the valve 124 and the proximal end of the tubular body in the alternate embodiment is especially useful in patients suffering from incontinence caused by hypermobility.

In patients suffering from incontinence caused by hypermobility, the bladder neck and proximal urethra rotate and descend in response to increases in intra-abdominal pressure. During a hypermobility event, the orientation of the urethra relative to the bladder may change between approximately 20° and 90°. In such patients, rotation and descent of the bladder neck and urethra result in an uneven transmission of intra-abdominal pressure to the bladder and urethra. This can cause the bladder pressure to exceed the urethral pressure by as much as 100 cmH$_2$O, resulting in incontinence. As illustrated in FIG. 13, however, the increased distance between the valve 124 and the proximal end of the tubular body 112 of the alternate embodiment allows the tubular body to kink during a hypermobility event, thereby occluding the lumen of the tubular body, which helps prevent undesired leakage of urine through the valve assembly.

Figure 12:
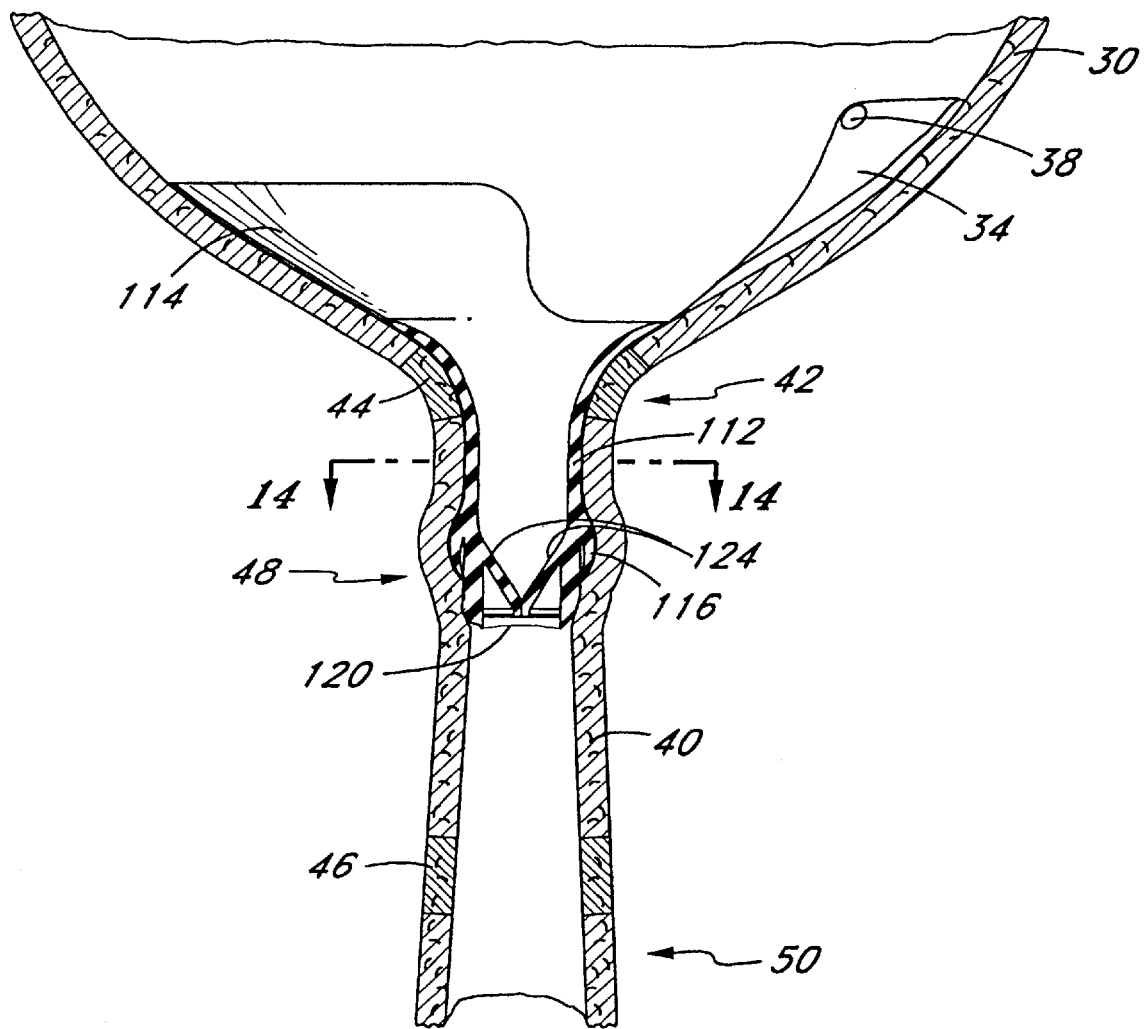
FIG. 12 is an elevational cross-sectional view taken along line 12—12 of FIG. 11.

FIGS. 12 and 13 illustrate the kinking feature of the tubular body 112 of the alternate embodiment of the present invention. FIG. 12 is an elevational cross-sectional view of the valve assembly positioned in the patient prior to a hypermobility event. In contrast, FIG. 13 illustrates the same view of the valve assembly during a hypermobility event. As can be seen, during the hypermobility event, the proximal portion of the tubular body 112 kinks or collapses, which helps to maintain continence without having to unduly increase the opening pressure of the valve 124.

In order to facilitate kinking of the tubular body 112, the tubular body preferably has a thinner wall and/or a noncircular cross section, such as elliptical or oval, at the desired point of kinking. In many patients, such as those suffering from incontinence caused by hypermobility, the desired point of kinking would be in the proximal portion of the tubular body approximately 0.1–1.5 cm distal to the proximal end 118 of the tubular body. In some patients, however, the desired point of kinking may be located elsewhere along the tubular body 112 as will be evident to one of skill in the art. In addition, the device of the present invention may have a thinner wall and/or noncircular cross section throughout the length of the tubular body. A tubular body having a noncircular cross section is illustrated in FIGS. 14 and 15, which show the lumen of the tubular body before and after kinking of the tubular body caused by a hypermobility event.

As discussed earlier in connection with the valve assembly of FIGS. 1–5, one of ordinary skill in the art will recognize that a variety of structures other than the first anchor 114, second anchor 116, and valve 124 illustrated in FIGS. 8–13 could be used in accordance with the alternate embodiment of the present invention.

The valve assembly of the present invention can be manufactured using any of the variety of means known to those of ordinary skill in the art. Preferably the valve is injection molded into an integral unit. Alternatively, the valve assembly 10, 110 can be fabricated from two or more separately molded units, which are secured using conventional techniques such as thermal bonding, solvent bonding or suitable adhesives known in the art. For instance, the valve 24, 124 and the remainder of the valve assembly 10, 110 could be manufactured separately and then combined into a single unit using conventional methods known to those of ordinary skill in the art.

The device of the present invention may be made of any suitable resilient material which is biocompatible and resistant to a urine environment. Preferred materials include silicone rubbers, latex rubbers and polyurethane, with silicone rubbers being the most preferred. In addition to facilitating functioning of the device, the choice of soft, resilient materials also enhances patient comfort.

To minimize encrustation and infection, coatings well known to those of ordinary skill in the art, such as silver fluoropolymers or sulfated polysaccharide pentosanpolysulfate, can be applied to the device.

The dimensions and configuration of the valve assembly 10, 110 can be varied considerably to suit particular design criteria desired for a particular application and still embody the present invention. Dimensions are largely limited by anatomical considerations as discussed above with respect to the length of the tubular body 12, 112, which is preferably approximately 0.5 cm to 3 cm in length, and more preferably less than about 1.5 cm in length. The diameters of the tubular body 12, 112 and second anchor 16, 116 are also dictated by anatomical considerations. In particular, the diameters of the tubular body and second anchor are chosen to fit securely within the urethra yet not exert an excess outward force on the urethra so that the tubular body can be compressed in response to urethral forces. Typical ranges for the outside diameter of the tubular body are approximately 0.5 cm to 0.8 cm (15–24 French), preferably about 0.6 cm (18 French). Typical ranges for the outside diameter of the second anchor are approximately 0.66 cm to 1 cm (20–30 French), preferably about 0.08 cm (24 French). The wall thickness of the tubular body is generally within the range of from about 0.15–3 mm, preferably about 0.25–1 mm, and more preferably about 0.4 or 0.5 mm.

In addition to anatomical considerations, the size and shape of various components of the valve assembly 10, 110 are also governed by the type of material used to construct the valve assembly.

A nonsurgical procedure for maintaining urinary continence in a patient, is generally accomplished as follows. A prosthetic urethral valve assembly such as 10 or 110 of the present invention is selected by the physician based on the sex of the patient as well as other anatomical and medical considerations. Using an installation device, such as the cystoscope 221 and grasping forceps 225 illustrated in FIG. 16 and described below, the physician transurethrally positions the prosthetic urethral valve assembly so that both the valve 24, 124 and the distal end 20, 120 of the tubular body 12, 112 lie between the internal urethral sphincter and the external urethral sphincter so that the opening pressure of the valve varies in response to changes in physiologic parameters.

Figure 16:
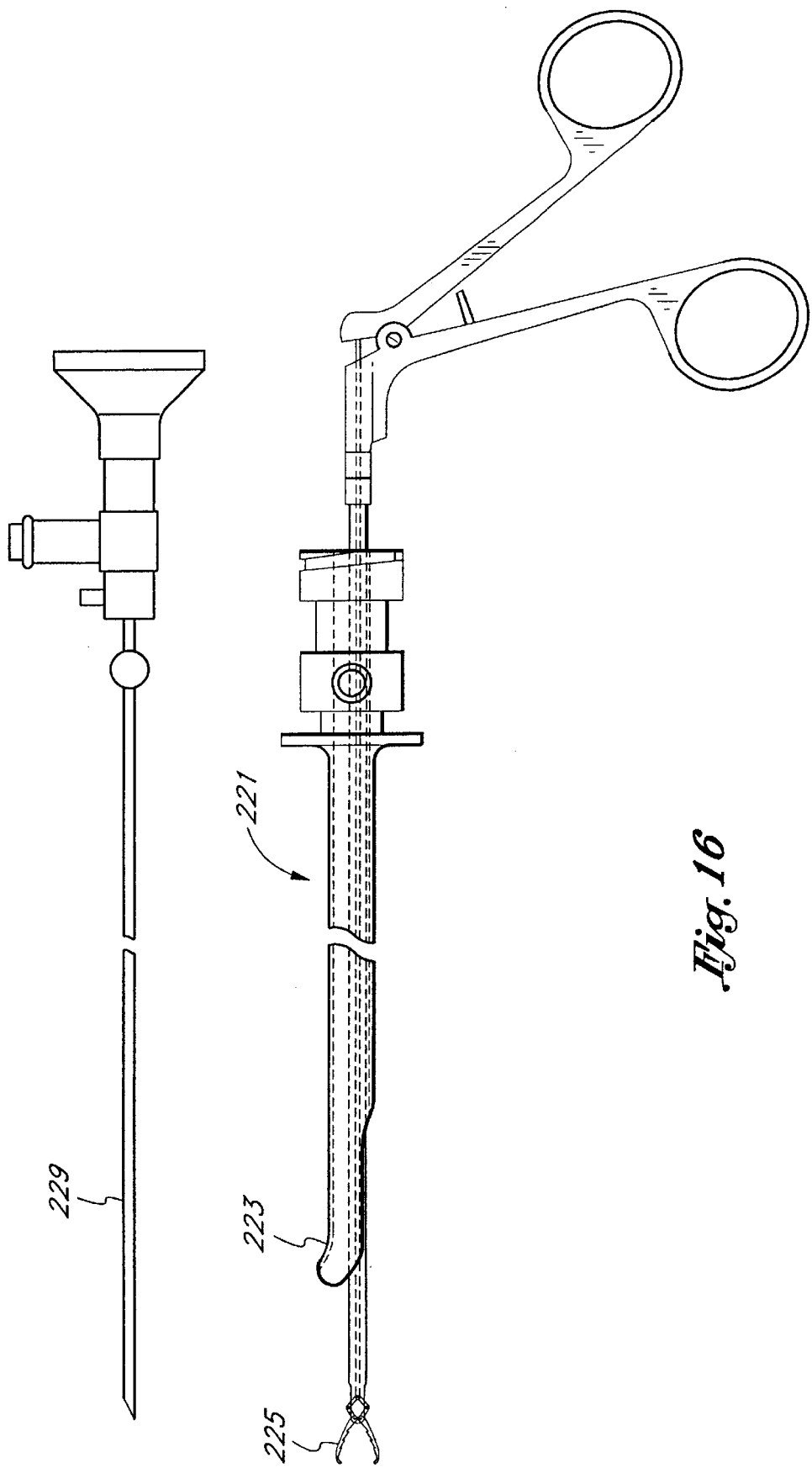
FIG. 16 is a partially exploded side view of various components of a device for installing the prosthetic urethral valve of the present invention.
Figure 17:
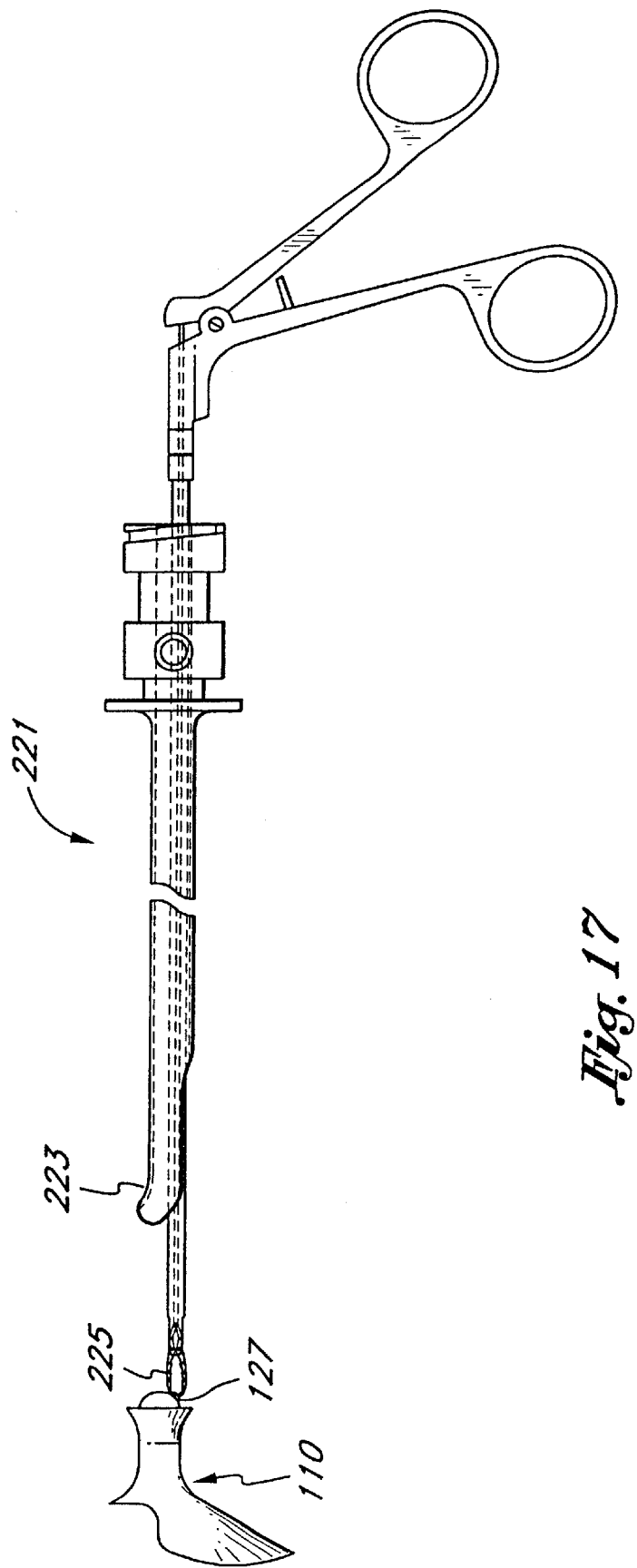
FIG. 17 is a side view of the grasping forceps extending distally from the cystoscope to releasably engage the prosthetic urethral valve of the present invention.

With reference to the installation device depicted in FIG. 16, one method of positioning the valve assembly 10, 110 is accomplished as follows. The physician transurethrally advances the cystoscope 221 and rod lens 229 into the bladder in accordance with conventional techniques. The physician then performs a standard cystoscopic examination of the bladder and fills the bladder with an irrigant. After performing the cystoscopic examination, the physician removes the cystoscope 221 from the urethra and removes the rod lens 229 from the cystoscope. The grasping forceps 225 are then passed through the cystoscope 221 so that the forceps 225 extend beyond the distal end 223 of the cystoscope 221 as illustrated in FIG. 16. A water soluble lubricant, such as K-Y jelly is applied to the outside of the valve assembly. The forceps 225 are used to releasably engage the valve assembly. For example, as illustrated in FIG. 17, the gripping boss 127 of the valve assembly is preferably releasably engaged by the forceps 225. The physician then carefully pushes the valve assembly into the distal end 223 of the cystoscope 221, collapsing the valve assembly as needed. The physician may also gently withdraw the forceps proximally to pull the valve assembly into the distal end of the cystoscope.

After placing the valve assembly 10, 110 into the distal end of the cystoscope, the physician passes the cystoscope through the urethra and into the bladder. Rod lens 229 is then inserted into the cystoscope 221 until it contacts the valve assembly. Using the rod lens and the forceps 225, the physician axially displaces the valve assembly distally out of the distal end 223 of the cystoscope 221 and into the bladder. While viewing the valve assembly 10, 110 in the bladder using the rod lens 229, the physician can rotate the forceps, if necessary, to properly orient the valve assembly and the first anchor 14, 114 relative to the base of the bladder and the trigone region.

While keeping the forceps stationary relative to the cystoscope, the physician withdraws the cystoscope, proximally thereby placing traction on the valve assembly in order to lodge the first anchor relative to the base of the bladder while avoiding contact between the first anchor and trigone region. Optionally, the position of the valve assembly can be confirmed using well known radiologic methods, such as in those embodiments in which a visualization ring has been incorporated into the valve assembly.

If the valve assembly is not properly positioned, the physician can readvance the cystoscope and the valve assembly into the bladder to rotate and reposition the valve. After the valve assembly is properly positioned, the physician releases the valve assembly from the forceps and withdraws the cystoscope, including the forceps and rod lens, from the patient.

The valve assembly 10, 110 can also be positioned using a standard embolectomy balloon catheter rather than the grasping forceps 225 described above. After performing a standard cystoscopic examination of the bladder and filling the bladder with an irrigant, the physician removes the cystoscope 221 from the urethra and removes the rod lens from the cystoscope leaving the bridge attached. The balloon catheter is then passed through the bridge and the cystoscope 221 so that the inflatable portion of the balloon catheter extends beyond the distal end 223 of the cystoscope. A water soluble lubricant, such as K-Y jelly, is applied to the outside of the valve assembly 10, 110. A standard balloon catheter threading tube is then advanced through the tubular body 12, 112 from the proximal end 18, 118 to the distal end 20, 120 of the tubular body.

The tip of the balloon catheter is then placed against the threading tube and the physician gradually extends both the balloon catheter and threading tube through the valve 24, 124 of the valve assembly 10, 110. The physician then carefully pushes the valve assembly into the distal end 223 of the cystoscope 221, collapsing the valve assembly as needed. After placing the valve assembly into the distal end of the cystoscope, the physician passes the cystoscope through the urethra and into the bladder.

The balloon catheter is then advanced distally so that the inflatable portion of the balloon catheter extends beyond the distal end of the cystoscope. The balloon is then inflated by the physician using conventional inflation media, such as fluid. The rod lens 229 is then inserted into the cystoscope 221 until it contacts the valve assembly. Using the rod lens (or other push rod structure), the physician axially displaces the valve assembly distally beyond the distal end of the cystoscope and into the bladder where it remains coaxially positioned about the balloon catheter shaft proximally of the balloon.

While viewing the valve assembly in the bladder using the rod lens, the physician can rotate the shaft of the balloon catheter, if necessary, to properly rotationally orient the valve assembly and the first anchor 14, 114 relative to the base of the bladder and the trigone region. During or after retraction of the cystoscope through the bladder neck, the physician retracts the inflated balloon catheter proximally in order to lodge the first anchor 14, 114 relative to the base of the bladder while avoiding contact between the first anchor and the trigone region. Optionally, the axial position of the valve assembly can be confirmed using well known radiologic methods, such as in those embodiments in which a visualization ring has been incorporated into the valve assembly. If the valve assembly is not properly positioned, the physician can readvance the cystoscope, balloon catheter, and valve assembly into the bladder to reposition the valve. After the valve assembly is properly positioned, the physician deflates the balloon catheter and withdraws the cystoscope, including the deflated balloon catheter and rod lens, from the patient.

Upon positioning internally as described above, the valve assembly 10 is automatically activated in response to physiologic conditions and thus can be controlled voluntarily by the patient without manual intervention.

As needed, the valve assembly 10, 110 can be removed from the patient and replaced with a new valve assembly. Removal of the valve assembly can be accomplished in a variety of ways, including through use of the cystoscope 221, rod lens 229, grasping forceps 225 and/or embolectomy balloon catheter described above. For example, the grasping forceps 225 are used to grasp the tab 27. The valve assembly can then be drawn into the distal end of a tubular structure such as a channel in the cystoscope 221. Preferably, the valve is drawn into the cystoscope while the cystoscope is simultaneously advanced in the distal direction to avoid pulling the first anchor through the bladder neck.

Alternatively, the valve assembly can be pushed distally from its installed position into the bladder, using the grasping forceps 225, rod lens 229 or other pushing structure. Preferably the physician will keep a grasp on the valve assembly such as by tab 27 using forceps 225 throughout the proximal displacement step. Once the valve assembly is in the bladder, it can be pulled into the end of the cystoscope. With certain anchor designs, the anchor may simply be pulled transurethrally from the patient.

For convenience, the methods of positioning and removal described above were discussed with reference to valve assembly 10, 110. One of ordinary skill in the art will recognize, however, that the methods of positioning and removal described above can also be used with other embodiments of the present invention described in the subject application.

Figure 18:
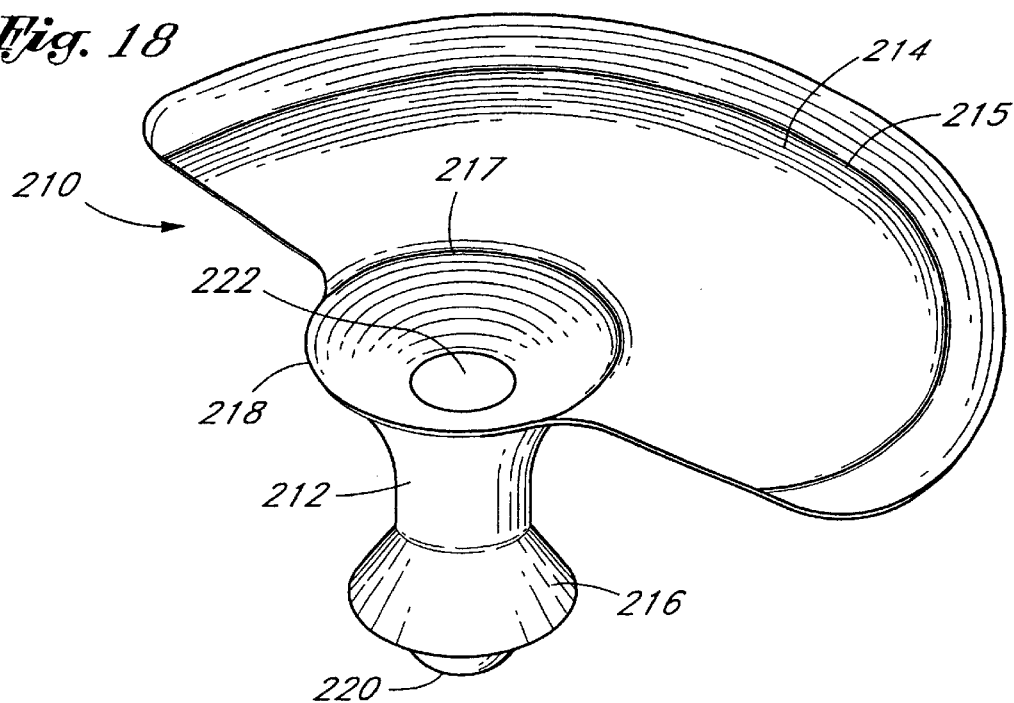
FIG. 18 is a perspective view of an alternate embodiment of the device according to the present invention.
Figure 19:
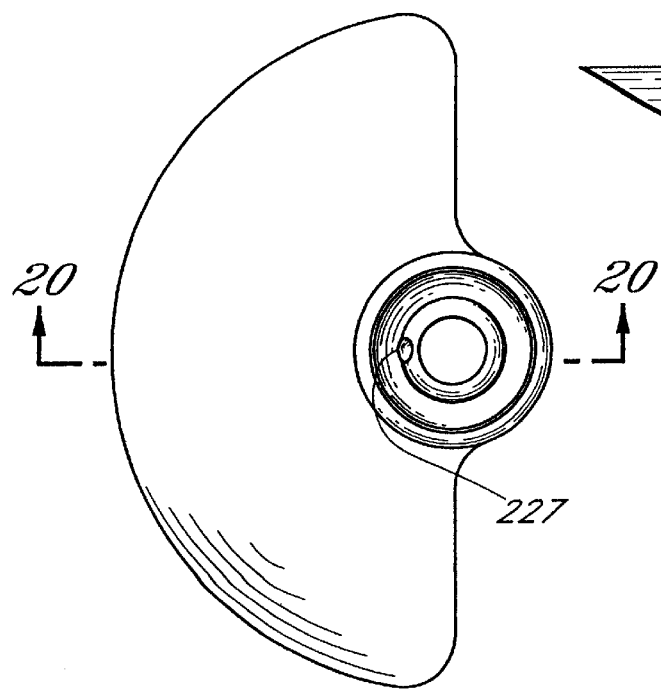
FIG. 19 is a bottom view of the embodiment depicted in FIG. 18.
Figure 20:
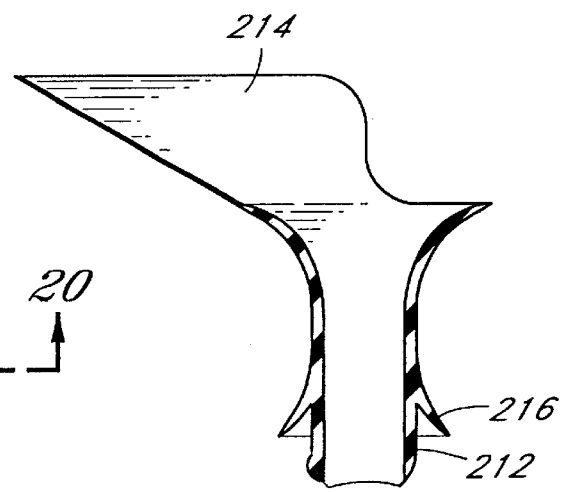
FIG. 20 is an elevated cross-sectional view taken along line 20—20 of FIG. 19.

Referring to FIGS. 18–20, there is shown an alternate embodiment of the present invention. The device 210 includes a tubular body 212 having a proximal end 218, a distal end 220 and a central lumen 222 extending therethrough. The device 210 also includes a first anchor 214, a gripping boss 227 and reinforcing rings 215, 217.

In addition to the first anchor 214, the device 210 may also include a second anchor 216. The structure and function of the second anchor 216 illustrated in FIGS. 18–20 is generally similar to that of the previously described embodiments of the present invention.

The device 210 preferably does not include a discrete valve. One of ordinary skill in the art will recognize, however, that the device 210 could include a discrete valve, such as those previously described in the subject application.

The device 210 functions primarily as a bulking agent or sealing device, which reversibly seals by collapsing at least part of the tubular body in response to the previously described inwardly directed urethral forces. These forces on the urethra help to cause the tubular body to collapse and seal when micturition is undesired, thereby maintaining urinary continence. Conversely, when micturition is desired, the pressure exerted by the urethra and bladder neck decreases, thereby allowing the tubular body to open.

The tubular body 212 of the device 210 can also function as a reversible seal by kinking due to for instance bending of the tubular body in response to the previously described rotational descent of the bladder neck and urethra, such as during a hypermobility event.

The dimensions and configuration of the device 210 are generally similar to those of the previously described embodiment illustrated in FIGS. 8–15. The tubular body 212 may be longer and have a thicker wall, however, in order to enhance the device's ability to serve as a bulking agent, yet still take advantage of the urethral pressure gradient and other previously discussed aspects of urinary anatomy/physiology.

Typical ranges for the length of the tubular body portion 212 of the device 210 are approximately 1.0–3.0 cm, preferably about 1.0–2.0 cm. Typical ranges for the outside diameter of the tubular body 212 and second anchor 216 are generally similar to those of the previously described embodiments of the present invention. Typical ranges for the wall thickness of the tubular body 212 of the device 210 are approximately 0.15–3 mm, preferably about 0.2 or 0.4–1.5 mm, and more preferably about 0.4 or 0.5 mm. The tubular body 212 of the device 210 can also have a variable thickness wall as previously discussed, wherein the wall of the proximal portion of the tubular body is thinner than that of the distal portion to facilitate kinking of the proximal portion, such as a during a hypermobility event. In addition, as previously discussed, in order to facilitate kinking, the tubular body can have a noncircular cross section, such as elliptical or oval, at the desired point of kinking or throughout the length of the tubular body.

As will be apparent to one of skill in the art, the device 210 can be manufactured in accordance with any of a variety of techniques and materials, such as those previously described. Also as discussed above, in addition to anatomical considerations, the size and shape of various components of the device 210 are governed by the type of material used to construct the device. For instance, particularly compliant materials, such as the silicone rubbers and other materials described above, facilitate urethral compression and/or kinking of the tubular body of the device, especially in devices having a thicker walled tubular body.

As with the previously described embodiments of the present invention, one of ordinary skill in the art will recognize that a variety of structures other than the first anchor 214 and second anchor 216 could be used in accordance with the device 210. One of ordinary skill in the art will also recognize that any of a variety of installation and removal techniques, including those described in the subject application, could be used to position the device 210 within the urinary tract of the patient and/or to remove the device therefrom.

Referring to FIGS. 21–25 and 27, there is shown an alternative embodiment of the present invention. The device 310 includes a tubular body 312 having a proximal end 318, a distal end 320 and a central lumen 322 extending therethrough.

As illustrated in FIG. 67, a tether 357 may be attached at the distal end 320 of the tubular body 312 to facilitate transurethral placement of the device. As will be apparent to one of ordinary skill in the art, a tether may also be used with the other embodiments of the invention described in the subject application.

Preferably, the tether 357 is a removable suture so that after the device has been positioned, the suture can be removed to decrease the risk of infection. The tether 357 may also comprise a nonremovable suture or be an extension of the tubular body itself. If the tether 357 is a nonremovable suture or extension of the tubular body, care should be taken to ensure that the tether does not extend beyond the urethral meatus in order to minimize the risk of infection. In those cases in which a nonremovable tether is used, the tether 357 may also be used to facilitate removal of the device.

Alternatively, the tubular body 312 may include a gripping tab or boss similar to that of the previously described embodiments of the present invention in order to facilitate transurethral placement and removal of the device.

The device 310 also includes a first anchor 314. The first anchor 314 preferably has an increasing diameter in the proximal direction and conforms to the bladder neck and/or proximal urethra. The outer diameter of the first anchor 314 at its proximal end 331 is preferably approximately 0.5–2.0 cm, more preferably about 0.8–1.3 cm.

The first anchor 314 functions to releasably secure the device 310 relative to the bladder neck and urethra. The first anchor 314 also helps prevent urine from escaping around the exterior of the device. When positioned intraurethrally, as illustrated in FIG. 66, the first anchor also serves a bulking/sealing function as discussed more fully below.

The first anchor is preferably an atraumatic retention structure which is enlargeable from a first, collapsed configuration for transurethral placement to a second, enlarged configuration for anchoring the device 310 relative to the bladder neck and/or urethra. In the embodiment illustrated in FIGS. 21–25 and 27, the first anchor 314 comprises a pliable generally circular retention structure that inclines generally radially outwardly in the proximal direction from the proximal end 318 of the tubular body 312 as illustrated in FIGS. 21, 23 and 25. The retention structure is mechanically biased in the direction of the second, enlarged configuration as illustrated to help prevent the device 310 from being displaced after positioning of the device in the patient as well as to help prevent urine from escaping around the exterior of the device.

Although shown as radiused in FIGS. 21 and 23, the first anchor 314 of the device 310 can also extend outwardly in a conical shape in the proximal direction from the proximal end 318 of the tubular body 312 as illustrated in an alternate preferred embodiment of the present invention depicted in FIG. 23A. The outer diameter of the conical-shaped first anchor 314 at its proximal end 331 is preferably approximately 0.5–2.0 cm, more preferably about 0.8–1.3 cm.

Figure 33:
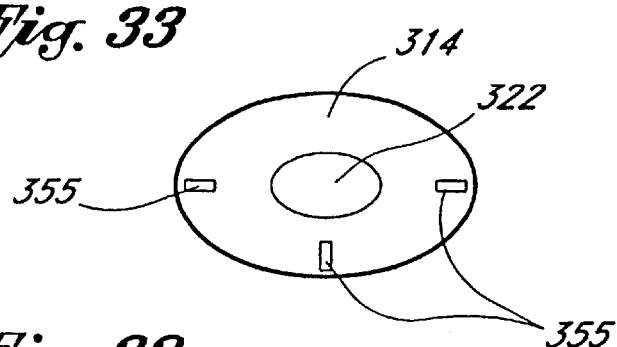
FIG. 33 is a top view of the embodiment depicted in FIG. 32.
Figure 32:
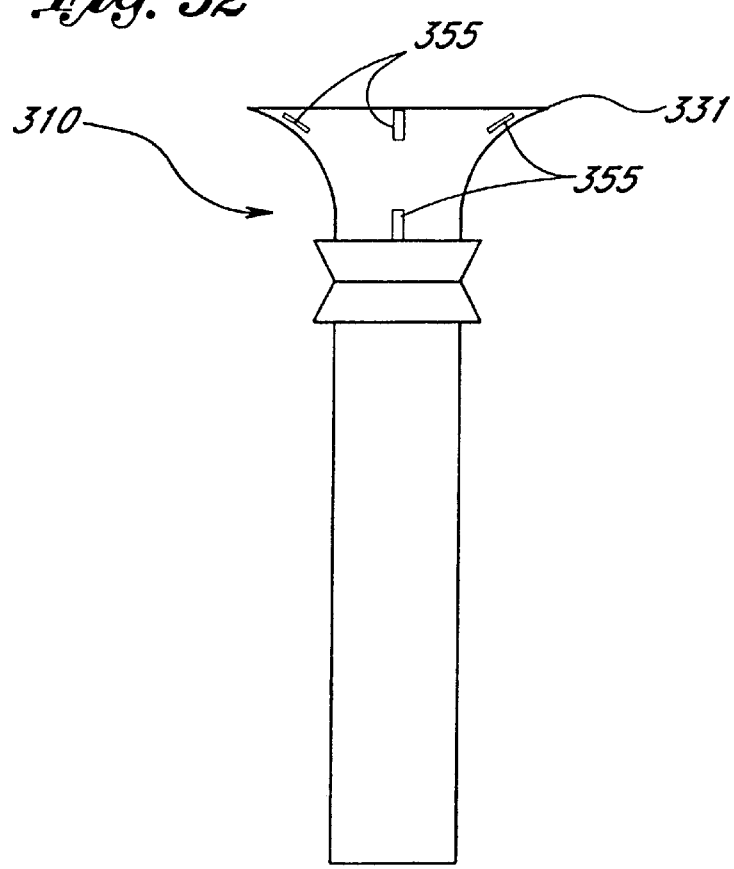
FIG. 32 is an elevational side view of an alternate embodiment of the device according to the present invention.
Figure 34:
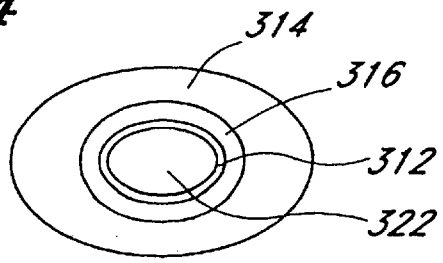
FIG. 34 is a bottom view of the embodiment depicted in FIG. 32.

The first anchor 314 can also be formed in a variety of other shapes, including the oval-shaped first anchor 314 illustrated in FIGS. 32–34 and the star-shaped first anchor 314 illustrated in FIGS. 35–38. The dimensions of the oval-shaped first anchor 314 at its proximal end 331 are preferably approximately 0.3 cm along the short axis by 1.0 cm along the long axis, more preferably approximately 0.4 cm along the short axis by 0.7 cm along the long axis.

With regard to the star-shaped first anchor 314 illustrated in FIGS. 35–38, the diameter of a circle drawn through the outer points 356 of the star-shaped first anchor 314 at its proximal end 331 is preferably approximately 0.5–2.0 cm, more preferably about 0.8–1.3 cm. The diameter of a circle drawn through the inner points 359 of the star-shaped first anchor 314 at its proximal end 331 is preferably approximately 0.3–1.8 cm, more preferably about 0.6–1.1 cm.

In addition to the first anchor 314, the device 310 optionally may include a second anchor 316 to further releasably secure the device 310 and stabilize the tubular body 312 within the urethra. In the embodiment of the device illustrated in FIGS. 21–25 and 27, the second anchor is a dual annular flange that extends radially outwardly in both the proximal and distal directions. The distance between the most proximal and most distal portions of the second anchor 316 measured along the longitudinal axis of the tubular body 312 can vary, but is preferably approximately 0.2–0.8 cm, more preferably about 0.4 cm. Optionally, one or more nitinol rings can be molded into the annular flange as previously discussed.

In the illustrated embodiment, the second anchor 316 is located along the length of the tubular body between the first anchor 314 and the distal end 320 of the tubular body 312. In such cases, the location of the second anchor 316 can vary, but preferably the midpoint of the second anchor 316 measured along the longitudinal axis of the tubular body 312 is approximately 0.2–0.8 cm from the proximal end 318 of the tubular body 312, and more preferably about 0.40 cm from the proximal end 318 of the tubular body 312. In addition, the distance between the most proximal portion of the second anchor 316 and the proximal end 331 of the first anchor 314 is preferably approximately 0.4–1.2 cm, more preferably about 0.8 cm.

Alternatively, the second anchor 316 may extend distally from the distal end 320 of the tubular body 312 as illustrated in FIG. 26. The structure and location of the second anchor 316 can also be generally similar to that of the previously described embodiments of the present invention.

The devices of the present invention, such as the device 310 may also include radiopaque markers 355 such as those illustrated in FIGS. 21–23, 25–26 and 32–33 to ensure proper positioning of the device, including rotational orientation. In the illustrated embodiments, the device has three markers 355 on the first anchor 314 and one marker 355 at the proximal end 318 of the tubular body 312. The preferred radial orientation of the markers 355 is shown in FIGS. 21–23, 25–26 and 32–33. One of skill in the art will recognize that any of a number of types of radiopaque markers 355, such as gold, tantalum or barium sulfate, and radial orientations may be used to ensure proper positioning of the device 310. In addition, the markers 355 can be included in portions of the device 310 other than the first anchor 314 and proximal end 318 of the tubular body 312. As will be apparent to one of ordinary skill in the art, the markers 355 can be incorporated into the device 310 or attached to the device 310 in a number of ways. The markers 355 are preferably bonded to the device 310 using silicone, such as room temperature vulcanizing silicone (NuSil MED 2000).

The device 310 preferably does not include a discrete valve. One of skill in the art will recognize, however, that the device 310 could include a discrete valve, such as those previously described in the subject application.

As discussed above with regard to the embodiment of FIGS. 18–20, the device 310 functions preferably as an intraurethral bulking agent, which reversibly seals in response to the previously described inwardly directed urethral forces. These forces on the urethra help to collapse and seal the tubular body 312 and/or first anchor 314 when micturition is undesired, thereby maintaining urinary continence by augmenting natural urethral sealing. Conversely, when micturition is desired, the pressure exerted by the urethra and bladder neck decreases, thereby allowing the tubular body and first anchor to open. Thus, the present invention provides a dynamic device which changes in response to natural internal forces, such as physiologic and anatomic forces acting upon the urethra and/or bladder neck.

The tubular body 312 of the device 310 can also function as a reversible seal by kinking due to for instance bending in response to the previously described rotational decent of the bladder neck and urethra, such as during a hypermobility event.

A typical range for the length of the tubular body 312 of the device 310 as provided to the physician is approximately 0.5–5.0 cm. As discussed more fully below, if necessary, the tubular body 312 is cut by the physician so that the length of the device 310 is preferably approximately 0.2–1.0 cm less than the patient's measured urethral length, more preferably about 0.60 cm less than the patient's measured urethral length. Typical ranges for the outside diameter of tubular body 312 are preferably approximately 0.20–0.80 cm, more preferably 0.40–0.60 cm. Typical ranges for the outside diameter of the second anchor 316 are preferably approximately 0.50–1.0 cm, more preferably 0.60–0.90 cm. Typical ranges for the wall thickness of the tubular body of the device 310 are approximately 0.30–0.80 mm, preferably about 0.40–0.60 mm, and more preferably about 0.50 mm.

The tubular body of the device can also have a variable thickness wall as previously discussed, wherein the proximal portion of the tubular body is thinner than that of the distal portion to facilitate kinking of the proximal portion, such as during a hypermobility event. In addition, as previously discussed, in order to facilitate kinking and sealing, the tubular body can have a noncircular cross-section, such as elliptical or oval, at the desired point of kinking or throughout the length of the tubular body.

A variety of tubular bodies having a noncircular cross-section are shown in FIGS. 28–31. The shape of the tubular body 312 optimally simulates the patient's natural urethral shape while restoring lost function without causing urinary obstruction.

FIGS. 30 and 31 illustrate an additional optional feature of the present invention. In particular, the tubular body 312 illustrated in FIGS. 30 and 31 has a stiffened posterior floor 361, which can be provided using a variety of conventional manufacturing techniques. FIG. 30 shows the tubular body in a closed position while FIG. 31 shows the tubular body in an open position. As can be seen, the shape of the stiffened posterior floor 361 remains relatively constant while the rest of the tubular body expands from the closed position to the open position during micturition. In addition, the stiffened posterior floor 361 acts as a backstop for downwardly directed abdominal pressure to help maintain continence during increases in abdominal pressure, such as during coughing.

A variety of first anchor types, second anchor types, and tubular body types have been described in the subject application in relation to specific embodiments of the present invention. One of ordinary skill in the art will recognize that these and other aspects of the present invention can also be combined in a variety of manners other than the combinations specifically described.

As will be apparent to one of skill in the art, the device 310 can be manufactured in accordance with any of a variety of techniques and materials, such as those previously described. Also as discussed above, in addition to anatomical considerations, the size and shape of various components of the device 310 are governed by the type of material used to construct the device. For instance, particularly compliant materials, such as silicone rubbers and other materials described above, facilitate urethral compression and/or kinking of the tubular body 312 of the device 310, especially in devices having a thicker walled tubular body. A preferred material for the device 310 is Dow Silicone, MDX 4-4210.

As with the previously described embodiments of the present invention, one of ordinary skill in the art will recognize that a variety of structures other than the first anchor 314 and second anchor 316 could be used in accordance with the device 310. One of ordinary skill in the art will also recognize that any of a variety of installation and removal techniques, including those described in the subject application, could be used to position the device 310 within the urinary tract of the patient and/or to remove the device therefrom.

The various embodiments of the present invention, such as device 310, may also include a resilient support structure 463 as illustrated in FIGS. 39–45 to provide an additional mechanical bias to help further secure the device within the patient. The resilient support structure 463 can also be used with other tubular devices as will be apparent to one of ordinary skill in the art.

Depending on the shape of the resilient support structure 463, it can also be used to bias the tubular body 312 of the device 310 towards a flattened/closed shape as illustrated in FIGS. 41–42 and 44–45 to help maintain continence without causing urinary obstruction. In addition, the resilient support structure provides some rigidity to minimize distortion of certain portions of the device during increases in abdominal pressure.

Figure 39:
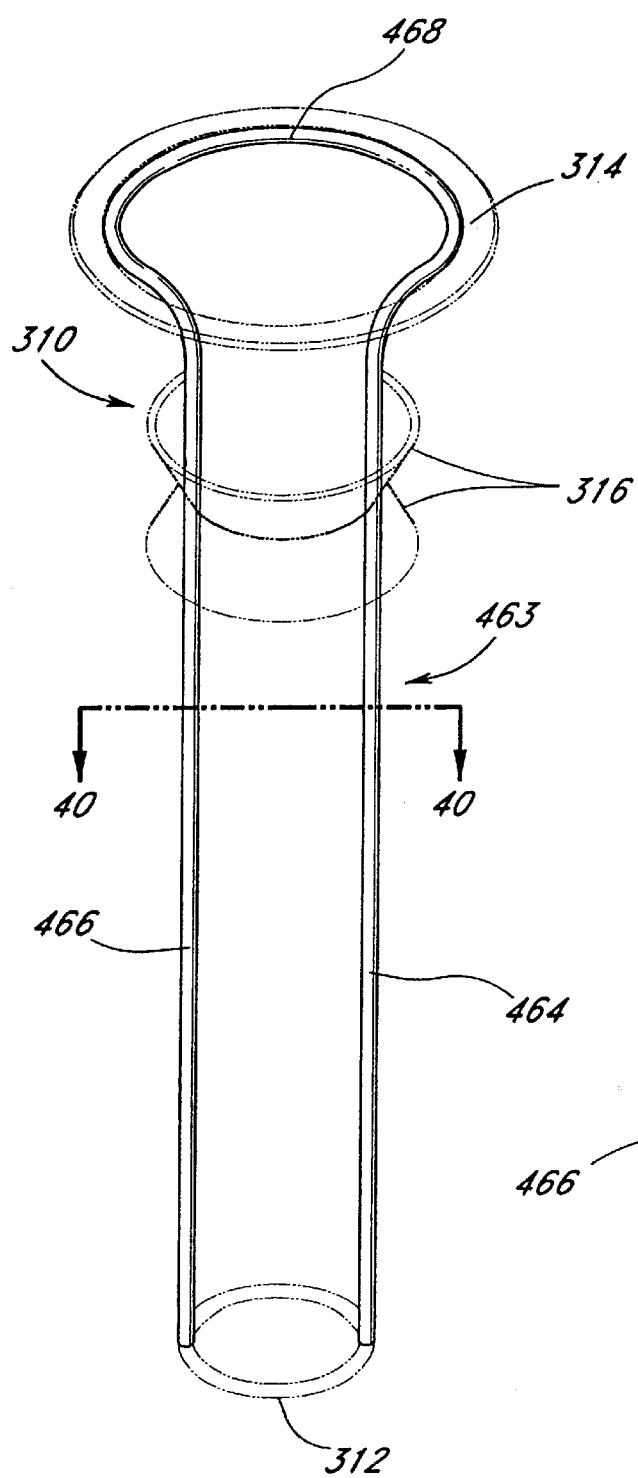
FIG. 39 is a frontal perspective view of an alternate embodiment of the present invention showing a resilient support structure embedded in a device which is shown in phantom.
Figure 40:
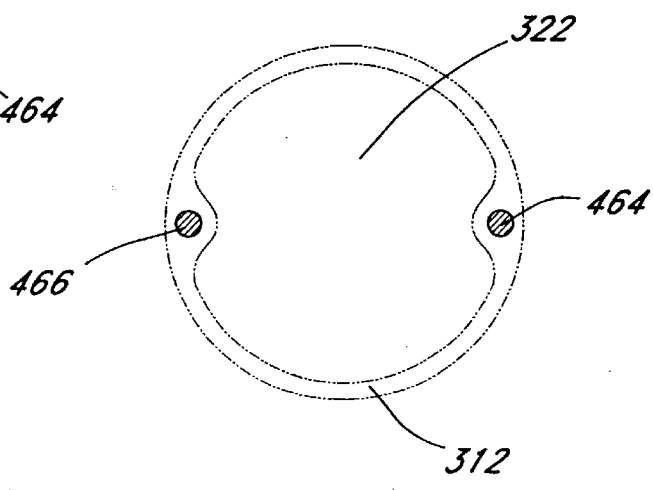
FIG. 40 is a cross-sectional view taken along line 40—40 of FIG. 39.

The resilient support structure 463 can be incorporated into the device 310 as illustrated in FIGS. 39 and 40. The resilient support structure 463 can also be inserted into the lumen of the device 310 as illustrated in FIGS. 41–42 and 44–45. In the devices illustrated in FIGS. 41–42 and 44–45, the bias of the resilient support structure 463 against the tubular body 312 of the device 310 holds the resilient support structure 463 in place relative to the device 310. The resilient support structure 463 shown in FIGS. 41–42 and 44–45 can also be secured to the device 310 using conventional techniques such as thermal bonding, solvent bonding or suitable adhesive known in the art.

Figure 46:
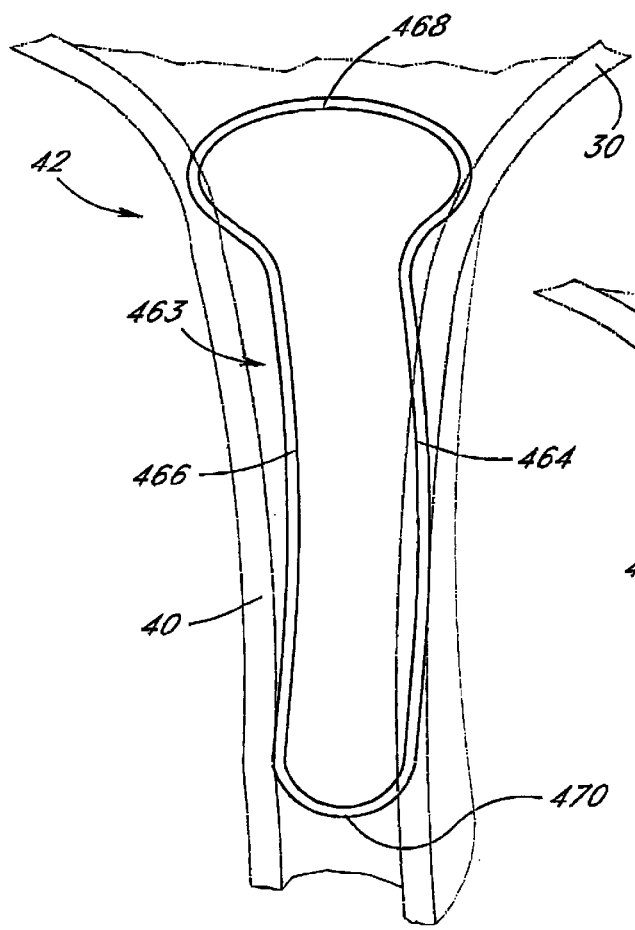
FIG. 46 is a perspective view of a resilient support structure of the present invention inserted in a urethra which is shown in phantom.
Figure 47:
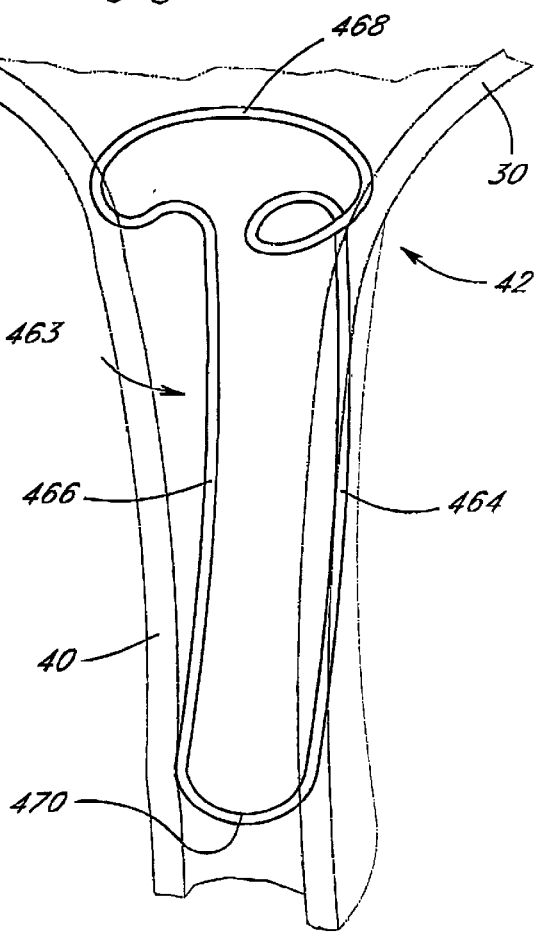
FIG. 47 is an alternate embodiment of the resilient support structure shown in FIG. 46 inserted in a urethra which is shown in phantom.
Figure 48:
FIG. 48 is a side view of the resilient support structure shown in FIGS. 46 and 47.

The resilient support structure 463 can also be used alone as illustrated in FIGS. 46–48. In FIGS. 46 and 47, the urethra 40, bladder neck 42, and a portion of the bladder 30 are shown schematically in phantom. In the embodiment of the present invention illustrated in FIGS. 46–48, a portion of the resilient support structure 463 extends into the bladder to help secure the resilient support structure 463 within the urinary tract. In other cases, the resilient support structure 463 might be totally intraurethral or extend only from the urethra to the bladder neck as opposed to extending into the bladder. The resilient support structure 463 is preferably shaped so that it exerts a biasing force against the urethra to further secure the resilient support structure 463 within the urinary tract as well as to bias the urethra towards a flattened cross-sectional shape to help maintain continence.

The resilient support structure 463 of FIGS. 39–48 preferably comprises two axially extending segments 464 and 466 extending from a first end portion 468. The resilient support structure 463 may also include a second end portion 470. The distance separating the first axially extending segment 464 from the second axially extending segment 466 is preferably greater than the diameter of the urethra to help anchor the resilient support structure 463 therein. The first and second axially extending segments 464 and 466 may also be curved as illustrated in FIGS. 43 and 48 so that after the resilient support structure 463 is positioned in the patient, a portion of the urethra is biased in the cephalad direction.

The first end portion 468 of the resilient support structure 463 may comprise a loop of varying shapes as illustrated in FIGS. 39, 41, 46 and 47. The first end portion 468 may have a diameter which is greater than the distance separating the first axially extending segment 464 from the second axially extending segment 466 to further anchor the resilient support structure 463, especially in those embodiments of the present invention in which the first end portion 468 of the resilient support structure 463 extends into the bladder neck and/or into the bladder.

The dimensions of the resilient support structure 463 of FIGS. 39–48 are largely governed by anatomical considerations and the size/shape of the device, if any, with which it is being included. One of ordinary skill in the art will recognize that a variety of sizes and shapes other than those illustrated for the resilient support structure 463 could be used in accordance with the present invention.

The resilient support structure 463 may be made of any suitable resilient material. Preferred materials include stainless steel, nitinol, titanium, and polymeric materials, such as polyurethane and polypropylene.

One of ordinary skill in the art will recognize that any of a variety of installation and removal techniques, including those described in the subject application, could be used to position devices having a resilient support structure 463, such as the devices illustrated in FIGS. 39–45, within the urinary tract of the patient and/or to remove such devices therefrom.

One of ordinary skill in the art will also recognize that the installation and removal techniques described in the subject application can also be used to position the resilient support structure 463 of FIGS. 46–48. In such cases, however, instead of releasably engaging the distal end of a tubular body, the device of FIGS. 46–48 is preferably releasably engaged with grasping forceps generally at the second end portion 470 of the resilient support structure 463 to position the device of FIGS. 46–48 within the urinary tract of the patient and/or to remove the device therefrom.

Another aspect of the present invention relates to an introducer 580 illustrated in FIGS. 55–59. The introducer 580 can be used as a conduit to pass a variety of devices into or through a body lumen or orifice to treat a variety of conditions. For example, the introducer 580 can be used to transurethrally position a variety of urological/gynecological devices, including the devices of the present invention such as device 310.

The introducer 580 is an elongate generally tubular structure having a first end 581, a second end 582, and a variable diameter central lumen 588 extending therethrough. The variable diameter feature of the central lumen 588 may be present along the entire length or along a portion of the length of the introducer 580. The introducer 580 also has an upper surface 583 and a lower surface 584.

The introducer 580 may also have a handle. The handle may be located at a variety of positions along the length of the introducer 580. Preferably, the handle is located at the second end 582 of the introducer 580.

The wall of the introducer 580 preferably has a longitudinally extending split 585, which extends from the first end 581 at least partially along the length of the wall of the introducer. Preferably, the longitudinally extending split 585 extends at least 2 cm from the first end 581 of the introducer 580. More preferably, the longitudinally extending split 585 extends from the first end 581 to the second end 582 of the introducer 580 as illustrated in FIG. 56. The split wall allows the introducer 580 to expand (FIG. 58) and contract or overlap (FIG. 59) relative to its resting state (FIG. 57). Expansion of the introducer 580 facilitates loading and deployment of the device 310 and minimizes distortion of the device 310 during loading and deployment thereof. To further facilitate expansion of the introducer 580, the second end 582 in the area of the split 585 can be chamfered approximately 0.1 cm by 45° at two places as illustrated at reference numeral 586 of FIG. 56. Contraction or overlapping of the walls of the introducer 580, such as in response as radially inwardly directed urethral forces during transurethral placement, minimizes the profile of the introducer 580, thereby minimizing urethral trauma and patient discomfort.

In addition, the edges of the introducer 580 are smoothed using conventional manufacturing techniques to minimize urethral trauma.

The introducer 580 can be made from a variety of materials, including polymers such as WP, polyesters and polyolefins. A preferred cellulosic material for the introducer 580 is Cellulose Acetate Propionate (CAP), which can be purchased from Eastman under the brand name "Tenite."

The first end 581 of the introducer 580 also preferably has an atraumatic tip 587 as illustrated in FIG. 55. The atraumatic tip 587 can be formed from a variety of materials, including the material used to construct the introducer 580. Preferably, the atraumatic tip 587 is formed with silicone, such as room temperature vulcanizing silicone (NuSil MED 2000). Small holes can be drilled into the first end 581 of the introducer 580 to facilitate attachment of the atraumatic tip 587, such as when the atraumatic tip 587 is formed with silicone.

The dimensions of the introducer 580 largely depend on anatomic considerations, the size of the device being inserted through the introducer, and the material used to construct the introducer. The length of the upper surface 583 of the introducer 580 is preferably approximately 8.0–14.0 cm, more preferably about 12.0 cm. As illustrated in FIG. 55, the length of the upper surface 583 is preferably greater than the length of the lower surface 584 so that the first end 581 slopes upwardly relative to the longitudinal axis of the introducer 580 at approximately a 30° angle. The outer diameter of the introducer 580 is preferably approximately 0.50–1.0 cm, more preferably about 0.70 cm. The wall thickness of the introducer 580 is preferably approximately 0.30–1.0 mm, more preferably about 0.50 mm. If an atraumatic tip 587 is included, it preferably extends longitudinally along the wall of the introducer 580 approximately 1.0–3.0 mm, more preferably about 2.0 mm.

An alternative nonsurgical or minimally invasive procedure for positioning an intraurethral device within the flow path between the bladder and the introitus to maintain urinary continence in a patient using the introducer 580 is generally accomplished as follows. For convenience, the following positioning and removal procedures will be described with reference to device 310. One of skill in the art will recognize, however, that these positioning and removal procedures can be used with a variety of devices, including the other embodiments of the present invention described in the subject application.

The urethral length is measured from the bladder to the introitus using a balloon measurement catheter or other conventional measuring techniques. A device for maintaining urinary continence, such as device 310, is selected by the physician. If necessary, the tubular body 312 is cut to length by the physician based on the patient's measured urethral length so that the length of the device 310 is tailored to the individual patient. Preferably the tubular body 312 is cut so that the length of the device 310 is preferably approximately 0.2–1.0 cm less than the measured urethral length, more preferably about 0.6 cm less than the measured urethral length.

A releasable engaging device, such as grasping forceps 225, is passed through the lumen 588 of the introducer 580 to releasably engage the device 310. The forceps can releasably engage the distal end 320 of the tubular body 312 directly, or can engage a gripping boss/tab or a tether 357 attached to the tubular body.

Using a coupling device, preferably a releasable coupling device such as a C-clip 291, the shaft 295 of the forceps 225 is attached to the shaft of a locating device having an expandable tip, such as a balloon catheter 290. Preferably, the shaft 295 of the forceps 225 is attached to the shaft 292 of the balloon catheter 290 so that the shoulder 293 of the balloon 294 of the balloon catheter 290 is separated by a distance "L" from the proximal end 331 of the first anchor 314 of the device 310 as illustrated in FIGS. 60–65. The distance "L" can be varied depending on where in the urinary tract the physician wants to anchor the device 310. The distance "L" may also be adjusted if a nonreleasable coupling device is used, such as by sliding the shaft of the balloon catheter relative to the shaft of the forceps. Preferably "L" is approximately 1–7 mm, more preferably about 3–7 mm so that the first anchor 314 of the device 310 lodges in the bladder neck and/or proximal urethra.

Figure 60:
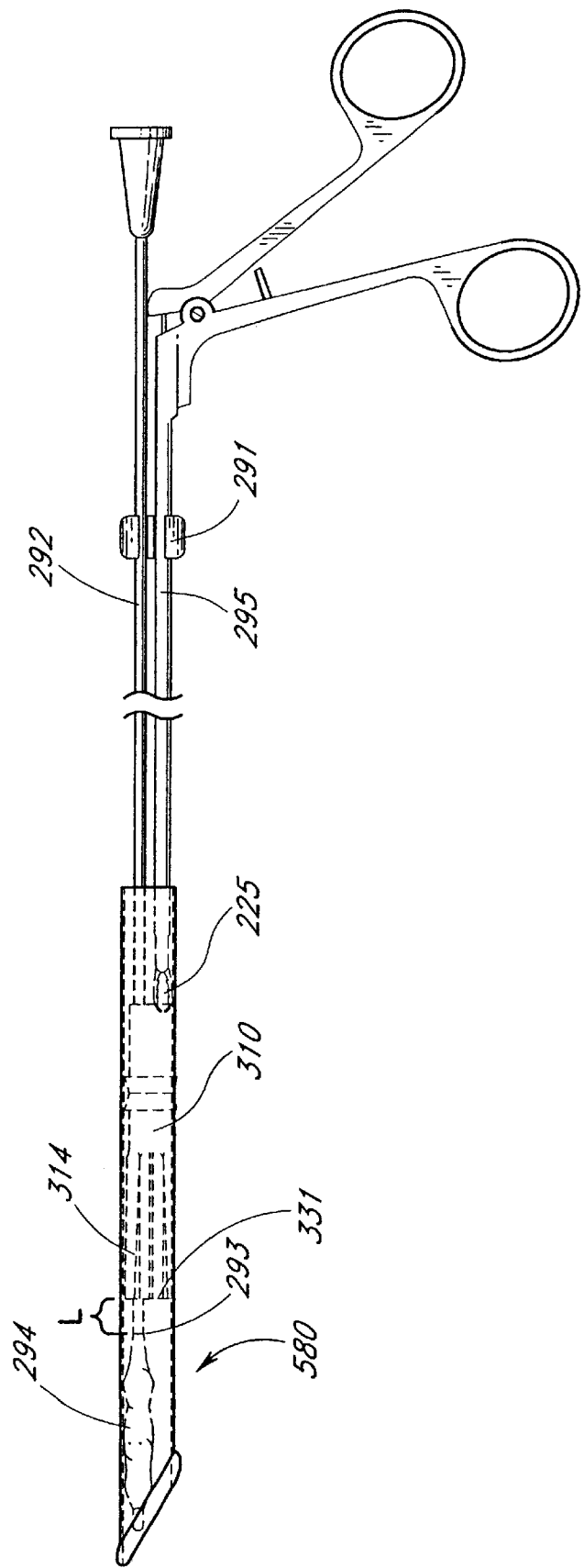
FIG. 60 is an assembled side view showing the device for maintaining urinary continence, balloon catheter, and grasping forceps inserted into the introducer.

The outside of the device 310 and balloon catheter 290 are lubricated with a water soluble lubricant, such as K-Y jelly and gently withdrawn into the introducer 580 as illustrated in FIG. 60. The introducer 580 is then passed into the urethra 40 so that the first end 581 of the introducer 580 extends into the bladder 30 as illustrated in FIG. 61.

Figure 61:
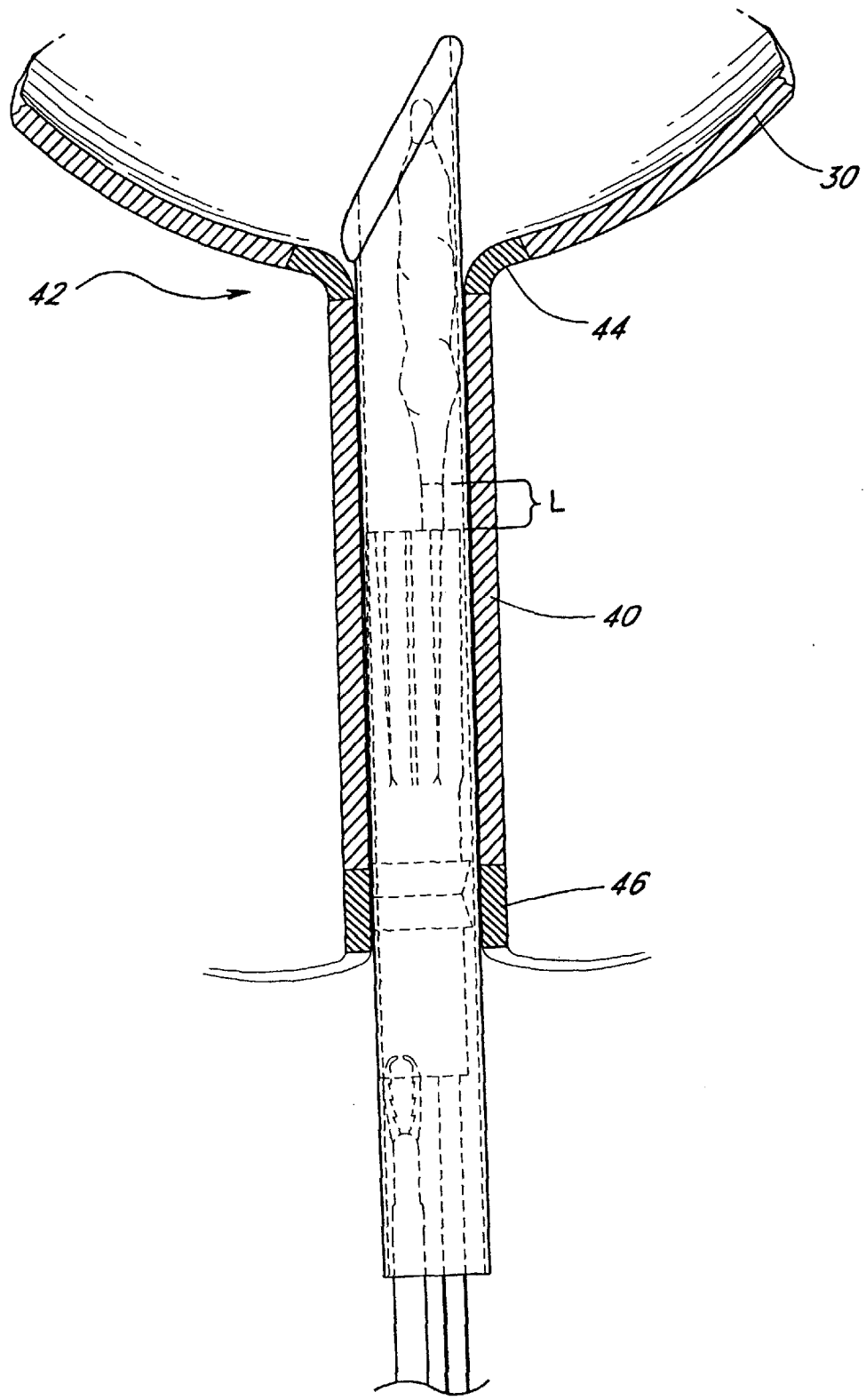
FIG. 61 is a schematic cross-sectional view showing the loaded introducer inserted into the urethra and bladder.

FIG. 61 also schematically illustrates the external urethral sphincter 46 and the internal urethral sphincter 44. In the female anatomy, the external urethral sphincter is difficult to distinguish. In the subject application, the external urethral sphincter is understood to include the urethral tissue immediately proximal to the urethral introitus. In the subject application, the internal urethral sphincter is intended to include the tissue at the urethro-vesical junction, also referred to as the bladder neck.

Figure 62:
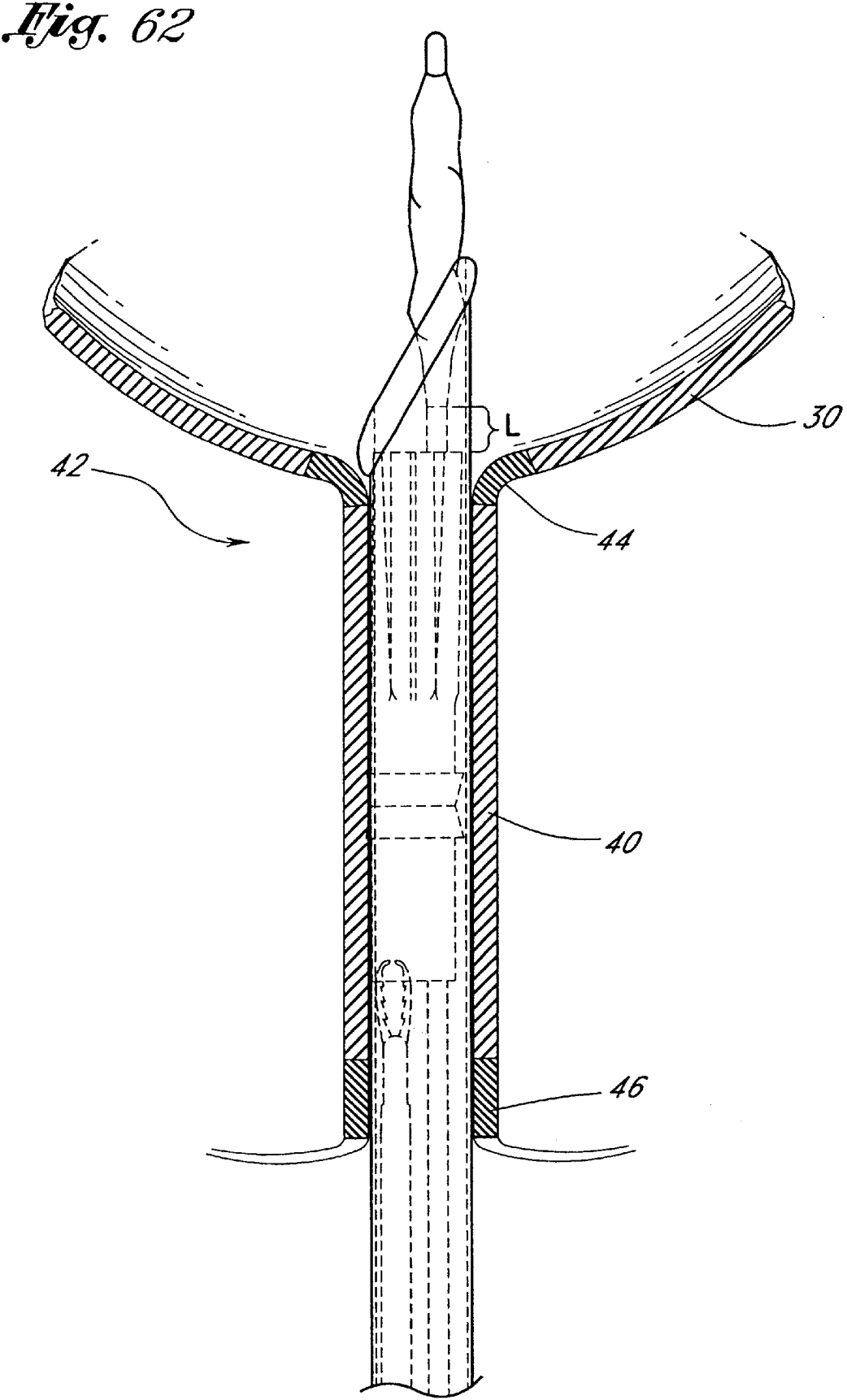
FIG. 62 is a schematic cross-sectional view showing the balloon catheter being advanced out of the introducer and into the bladder.
Figure 63:
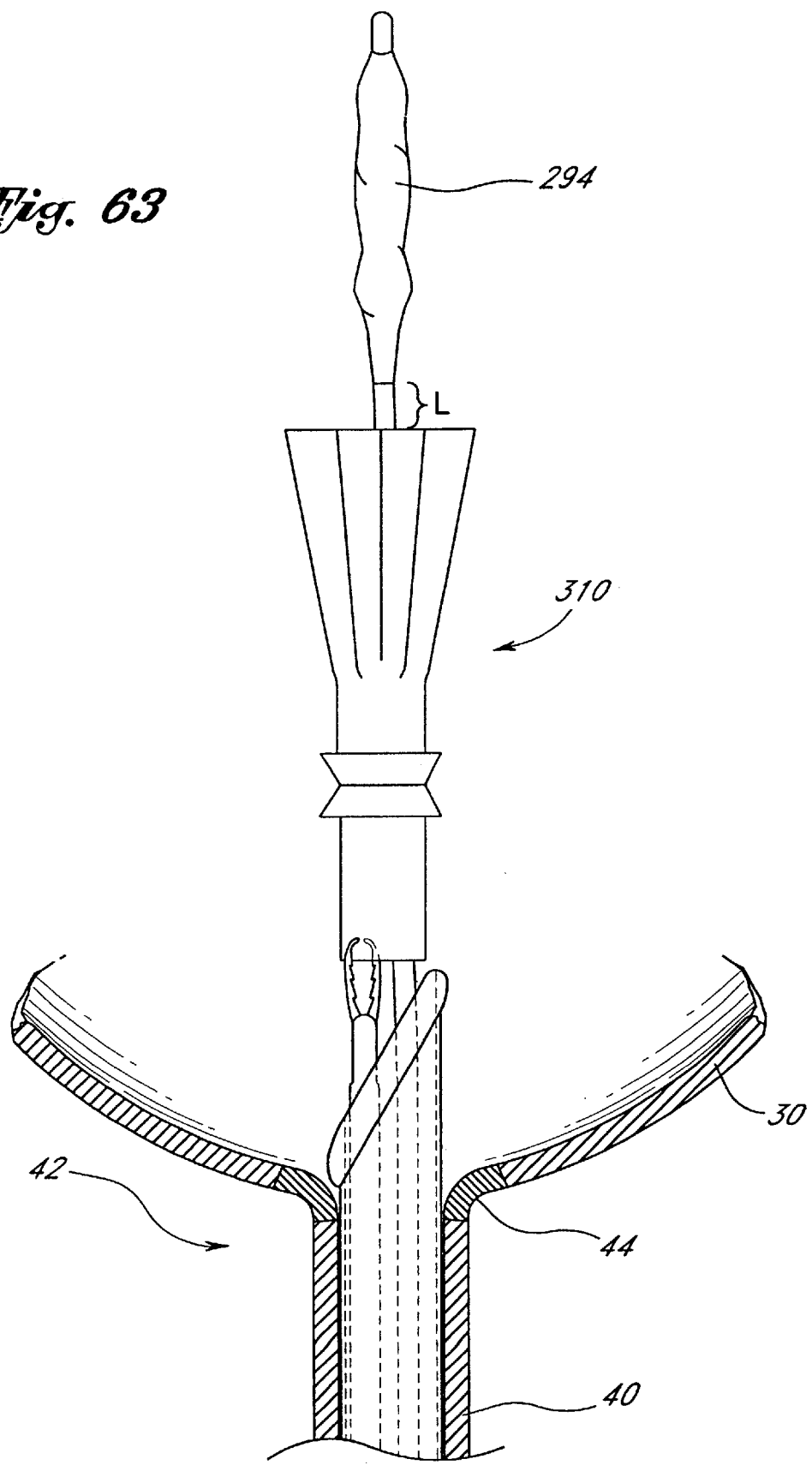
FIG. 63 is a schematic cross-sectional view showing the balloon catheter and device for maintaining urinary continence being displaced from the introducer into the bladder.
Figure 64:
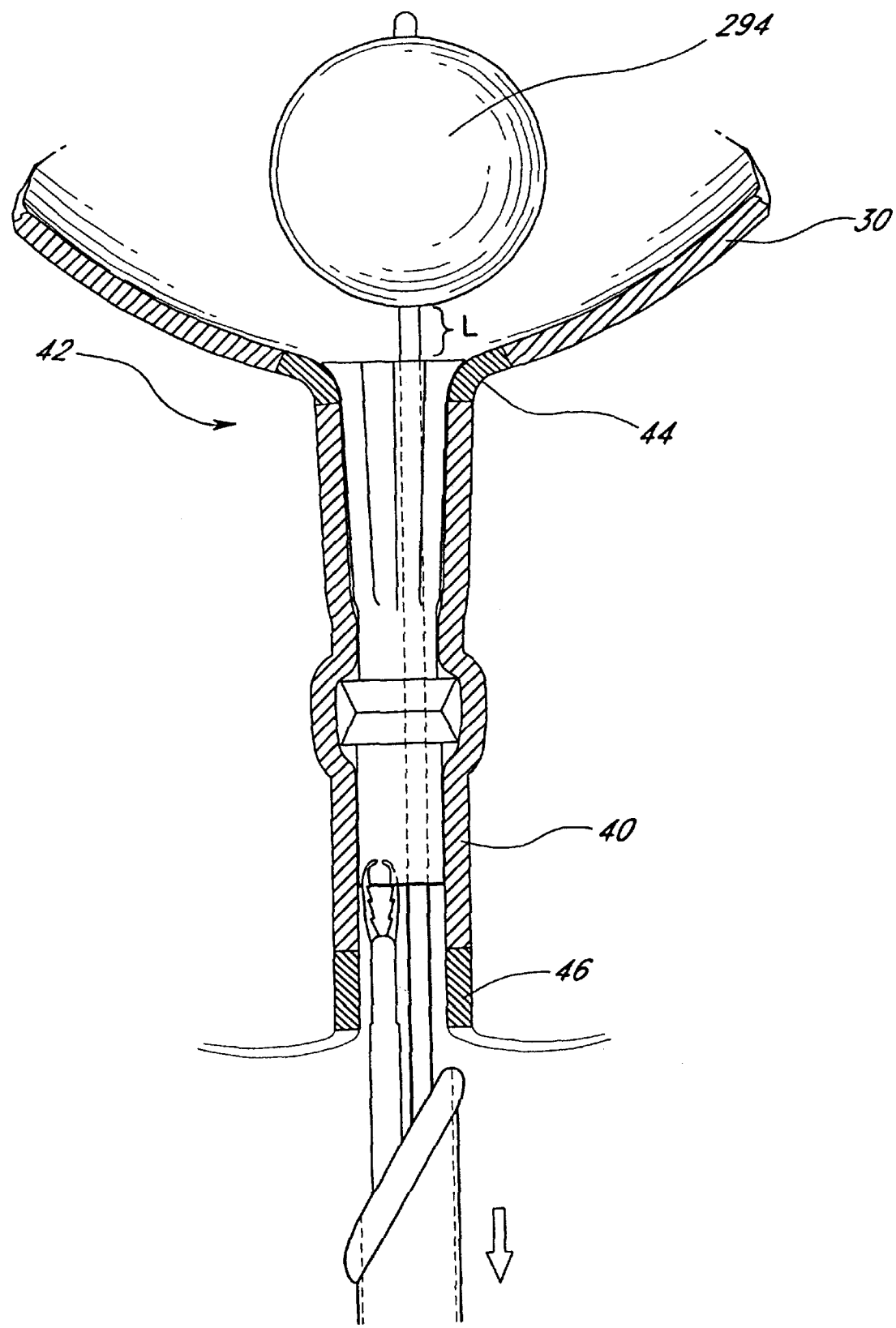
FIG. 64 is a schematic cross-sectional view showing the introducer being withdrawn from the urethra and the balloon being inflated within the bladder.
Figure 65:
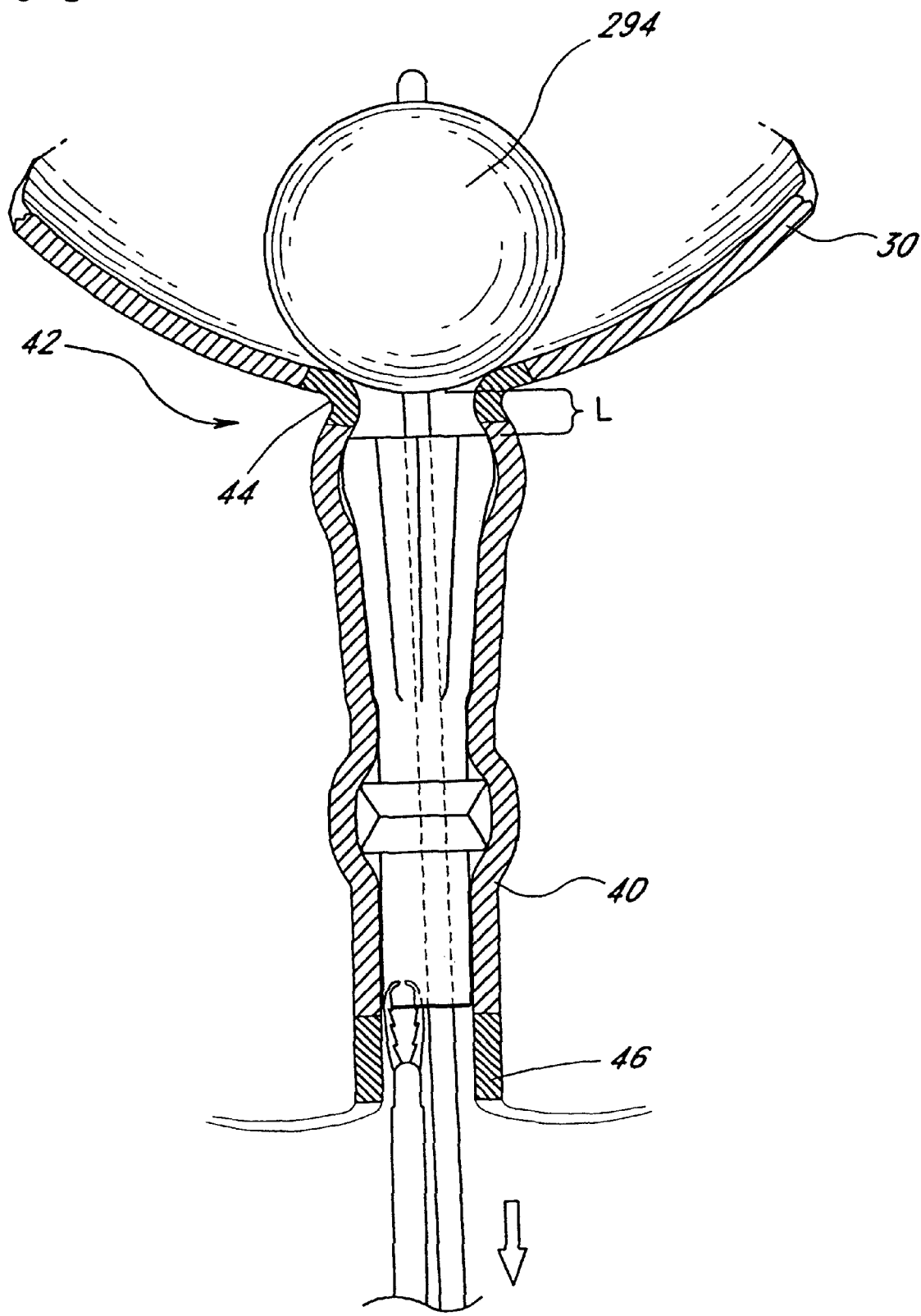
FIG. 65 is a schematic cross-sectional view showing withdrawal of the coupled grasping forceps and balloon catheter with the inflated balloon contacting the bladder neck.

FIGS. 62–63 illustrate the device 310 and balloon catheter 290 being carefully pushed out of the introducer 580 and into the bladder 30. As illustrated in FIG. 64, the introducer 580 is then withdrawn from the urethra 40 and the balloon 294 is inflated using conventional inflation media, such as water. The coupled grasping forceps 225 and balloon catheter 290 are then carefully withdrawn until the inflated balloon 294 contacts the bladder neck 42 a illustrated in FIG. 65. At this point, the proximal end 331 of the first anchor 314 resides within the bladder neck and/or proximal urethra the pre-selected distance "L" from the shoulder 293 of the inflated balloon 294.

The balloon 294 is deflated and the shaft 295 of the grasping forceps 225 is decoupled from the shaft 292 of the balloon catheter 290. The balloon catheter 290 is removed from the patient, the device 310 is released from the grasping forceps 225, and the grasping forceps are removed from the patient, leaving the device 310 properly positioned within the urinary tract of the patient as illustrated in FIG. 66. If a nonreleasable coupling device is used, the balloon 294 is deflated, the device 310 is released from the grasping forceps 225, and the coupled grasping forceps 225 and balloon catheter 290 are removed simultaneously from the patient, leaving the device 310 properly positioned within the urinary tract of the patient.

Preferably the entire device 310 is positioned within the urethra. The device 310 is held in place due to the natural compliance of the urethra 40. Optionally, the position of the device 310 can be confirmed using well-known radiologic methods, such as in those embodiments which include radiopaque markers 355.

Figure 68:
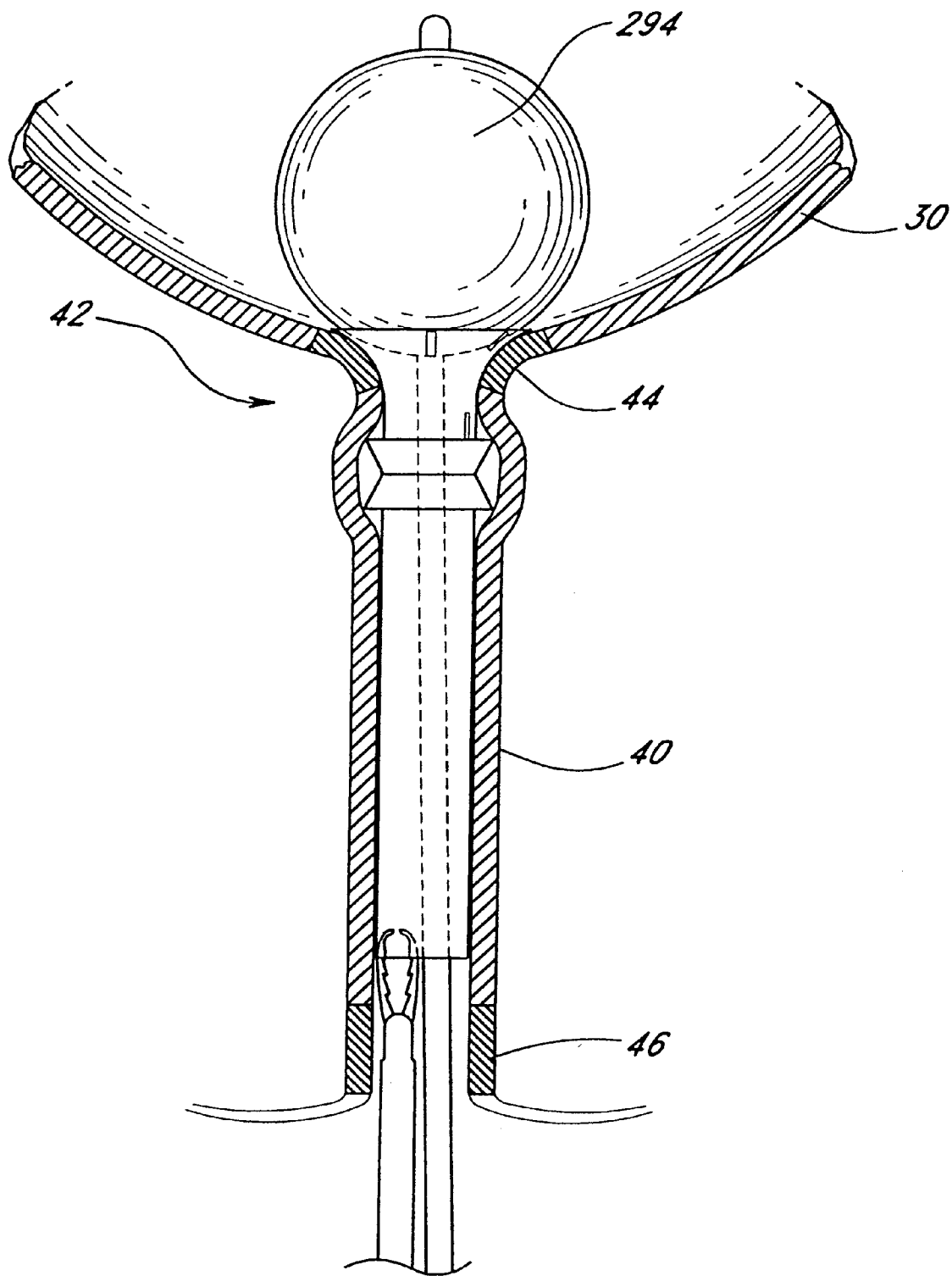
FIG. 68 is a schematic cross-sectional view showing the device for maintaining urinary continence being placed in an alternative position in the urinary tract.
Figure 69:
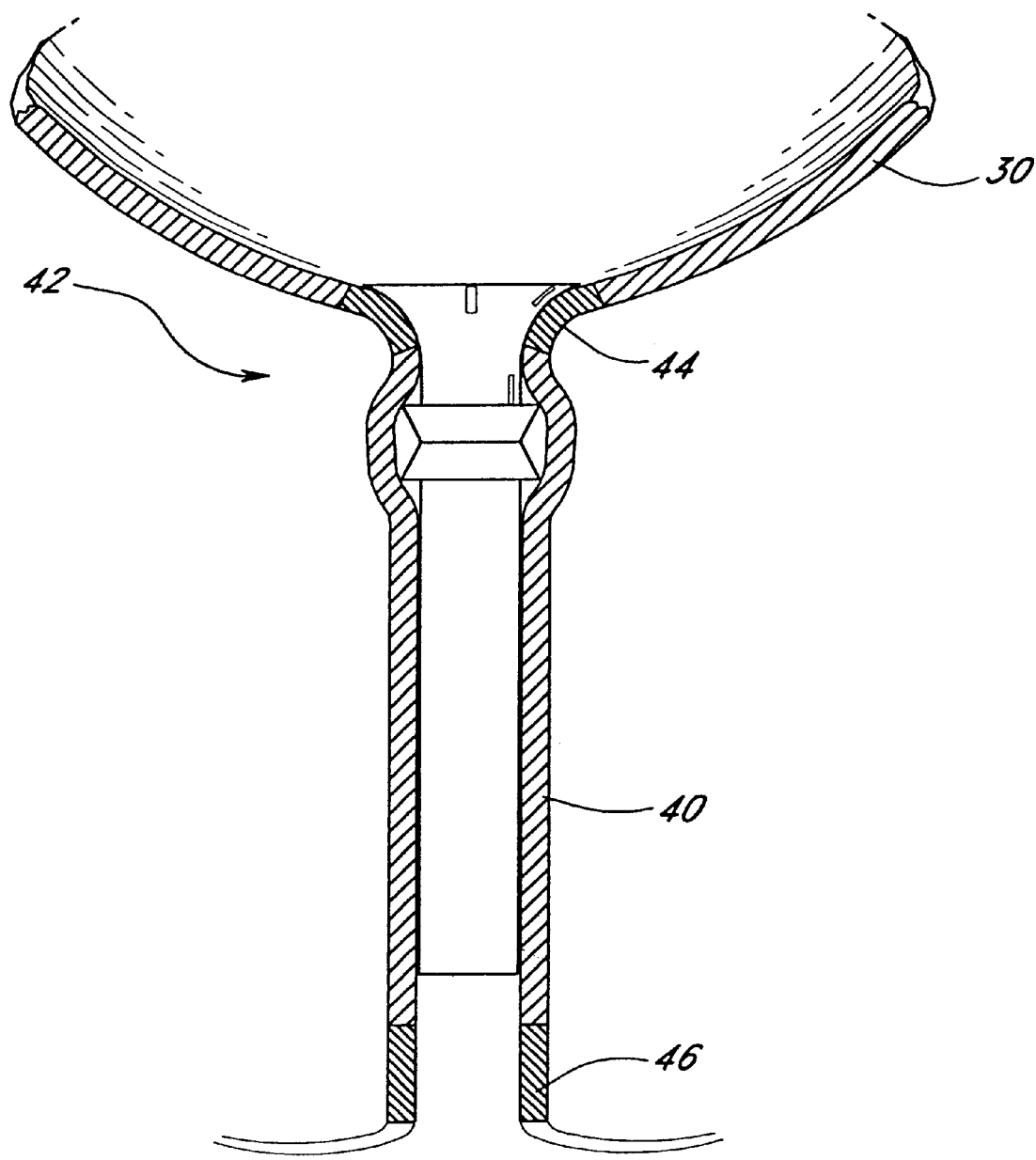
FIG. 69 is a schematic cross-sectional view showing the device for maintaining urinary continence positioned within the urinary tract after removal of the balloon catheter and grasping forceps illustrated in FIG. 68.
Figure 73:
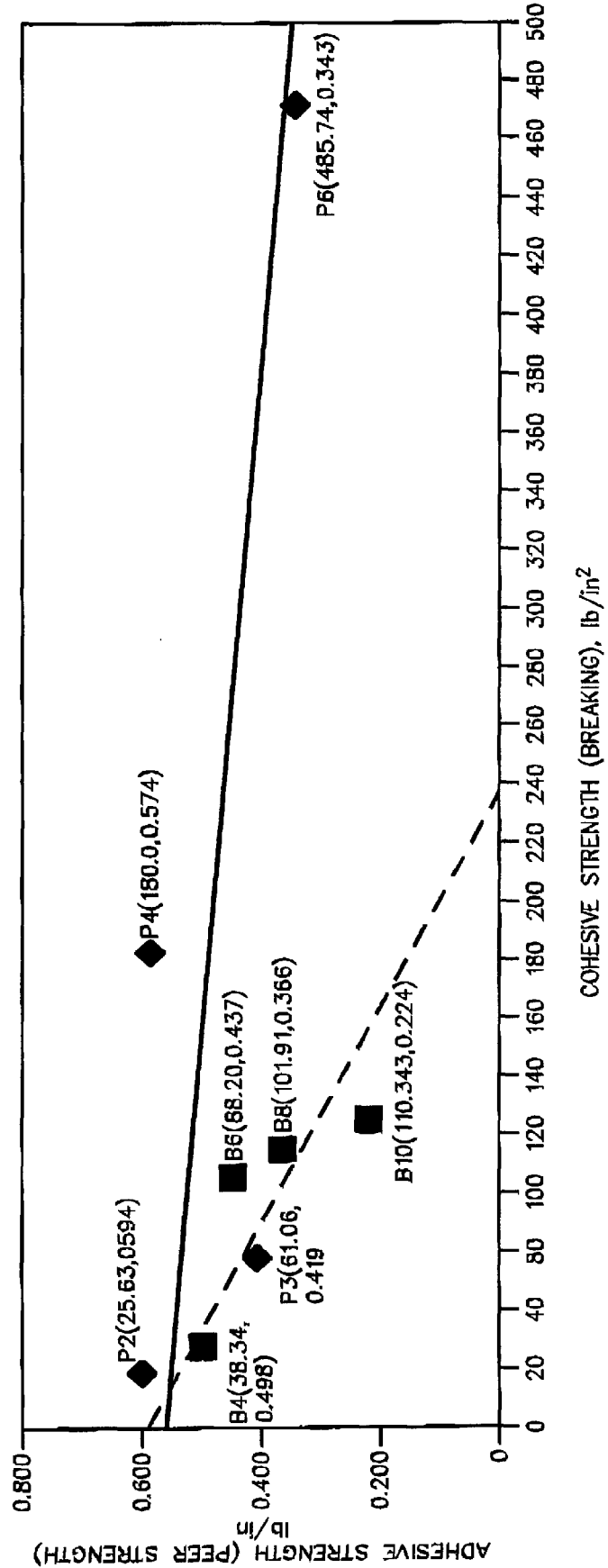
FIG. 73 is a graph depicting the adhesive strength/cohesive strength profiles for two representative bioadhesive copolymers of the present invention which have been formulated with several ratios of carboxyl functional monomers to hydrophobic monomers.

FIGS. 68–69 illustrate the device 310 placed in an alternative position. The position of the device in the urinary tract is related to a number of factors, such as the etiology of the patient's incontinence and the type of device being using to treat the patient. As illustrated by comparing FIGS. 65–66 to FIGS. 68–69, by varying the position of the shoulder 293 of the balloon 294 in relation to the proximal end 331 of the first anchor 314 prior to coupling the shaft 295 of the grasping forceps 225 to the shaft 292 of the balloon catheter 290, the physician can accurately place the device 310 in any of several desired positions in the urinary tract.

The devices of the present invention, such as device 310, can also be positioned within the urinary tract fluoroscopically. As discussed above, after measuring the urethral length, the tubular body of the device is cut to length by the physician. The bladder is filled with contrast fluid. The distal end of the device 310 is releasably engaged using grasping forceps 225 as discussed above. The outside of the device 310 is lubricated with a water soluble lubricant, such as K-Y jelly and gently withdrawn into the introducer 580 as previously discussed. The introducer 580 is then passed into the urethra so that the proximal end of the introducer extends into the bladder as discussed above. The device 310 is carefully pushed out of the introducer 580 and into the bladder while still be held by the grasping forceps 225. The introducer is then withdrawn from the urethra. Under fluoroscopic control, the device 310 is then withdrawn into the urethra until the first anchor 314 is observed to be just within the bladder neck, which is indicated by visualizing an inward movement of the radiopaque markers 355 on the first anchor 314 as it enters the urethra. The device 310 is then released from the grasping forceps and the grasping forceps are removed from the patient, leaving the device properly positioned within the urinary tract. Optionally, the position of the device is reconfirmed fluoroscopically after having the patient perform a variety of conventional maneuvers and exercises, including those which increase abdominal pressure.

As needed, the devices of the present invention can be removed from the patient and replaced as previously discussed. Because the device 310 does not contain any protruding sharp or rigid elements, if an emergency arises, such as an obstruction, the device 310 can be pushed into the bladder using a conventional catheter, such as a Fall catheter without causing damage to the urethra or bladder. The device 310 can remain in the bladder without causing any complications until the patient is able to see their physician for removal and replacement of the device.

PRIOR BIOADHESIVE MATERIALS

For certain embodiments of the intraurethral valves of the present invention, it is desirable to adhere the valves to the inside of the urethra to prevent or minimize migration of the valves. The incorporation of an adhesive material into the structure of the intraurethral valves may be used to accomplish this objective.

The prior art teaches two types of adhesives to attach a substrate to tissues. The first type of adhesive forms permanent (covalent) bonds to tissue surfaces. For example, liquid adhesives containing monomers, oligomers, or short chain polymers may be spread on a tissue surface, and then cured with ultraviolet light, moisture, or heat to form adhesive bonds to the tissue. Because the monomers/oligomers are diffused into the surface of the tissue, they cure with the tissue layer, forming permanent covalent bonds to the tissue. A substrate adhered to a tissue surface by a covalent bonding adhesive may not be removed without tearing or breaking the substrate or the tissue surface. An example of a covalent bonding adhesive is cyanoacrylate, which is often used as a surgical glue.

The second type of adhesive which may be used to bond a substrate to tissue forms non-permanent (noncovalent) bonds with the tissue surface. Consequently, substrates adhered with non-permanent adhesives may be more easily removed from a tissue without damaging the tissue. For biomedical applications, this type of adhesion is termed bioadhesion, and the class of adhesives forming these types of bonds are bioadhesives. For applications where substrate removal is contemplated, it is preferred that the bioadhesive have a bonding strength high enough to adhere to the tissue surface, but low enough to fail adhesively prior to the breaking of the substrate or the tissue.

The bioadhesive compositions taught by the prior art are generally unsuitable for directly forming a medical device which can be cleanly removed and reapplied to tissue. The prior art bioadhesives are generally cross-linked hydrophilic materials and lightly cross-linked hydrophilic materials, often referred to as hydrogels. These bioadhesive hydrogels exhibit good adhesion to tissue, but possess inherently weak structural integrity. Consequently, before the desired bioadhesive properties of these hydrogels may be incorporated into a medical device, the bioadhesive hydrogels must first be combined with other materials to achieve acceptable structural properties. For example, hydrogels may be milled into particulate or fibrous forms and then mixed with other binding materials to yield a mixed composition of reasonable mechanical strength which can then be fashioned or incorporated into a medical device. In these applications, the prior art hydrogels exist in the mixture as discrete particles varying in diameter from about 1 to 100 microns, and generally from 10 to 100 microns (or larger).

The physical and chemical properties of the prior art bioadhesive hydrogels necessitate their combination with other materials to achieve sufficient structural integrity. Polyacrylic acid (PAA) or polymethacrylic acid (PMAA) hydrogels are the most widely used prior art bioadhesives. These bioadhesive hydrogels form very strong non-permanent bonds to tissue, but due to poor internal cohesion, tend to break and leave residue on the tissue surface when removed. Furthermore, the mechanical strength of fully hydrated PAA and PMAA hydrogels is too weak to directly form a structurally acceptable medical device. Thus, as taught by the prior art, fully hydrated PAA and PMAA must be combined with other materials to enhance structural integrity before a structurally acceptable bioadhesive medical device can be made. Other prior art polymers used to make bioadhesives include polyhydroxyl ethyl methacrylate and polyethylene oxides. These polymers exhibit poorer adhesion in comparison to PAA and PMAA in very moist environments, and also lack sufficient structural integrity to form a medical device.

Because the prior art bioadhesive compositions utilize physical mixing or blending of PAA or PMAA particles with other materials, these bioadhesive compositions are only homogeneous to the length scale of the sizes of individual PAA or PMAA particles. This may vary from a minimum of 1 micron to hundreds of microns, but for most mixtures, range from 10 microns to about 100 microns. At this size, each of the PAA or PMAA particles still possesses its own inherent properties, and therefore the weak mechanical strength of each individual particles cannot be improved.

Furthermore, the heterogeneous structure created by mixing the prior art bioadhesive hydrogels with other materials to obtain mechanical strength often resulted in compositions with undesirable adhesive properties. For example, the mixed prior art bioadhesive hydrogels were often incorporated in devices such as patches or gels. Upon adhesion to a tissue or mucosal surface, the adhesive strength of bioadhesive particles in the mixture was often so strong that individual bioadhesive particles on the surface of the patch would cohesively break when peeling the patch away from the tissue or mucosal surface. This left bioadhesive residue on the tissue or mucosal surface, making the tissue or mucosal surface less receptive to the same bioadhesive without first being cleaned. For a disposable or repeat use device, this is undesirable, because it prevents application of a new device immediately after removing the old one.

DETAILED DESCRIPTION OF THE PREFERRED BIOADHESIVE COMPOSITIONS

The present inventors have found that the disadvantages of prior art bioadhesive materials are overcome by a new class of more uniform and homogeneous bioadhesive compositions. These novel bioadhesive compositions possess sufficient structural strength to be shaped into a medical device or portions of a device without first having to be combined or mixed with other materials, while at the same time exhibiting good adhesion to most types of tissues. Moreover, the tissue-specific bonding strength of these bioadhesive compositions is great enough to firmly attach a substrate to tissue, but is also low enough to fail adhesively prior to the breaking of most substrate materials or tissues when removal of the substrates from the tissues is desired. In other words, the bonding strength of these more uniform and homogeneous bioadhesives is less than both the cohesive strength of the bioadhesives themselves and the cohesive strength of many of the tissues or mucosal layers to which they may be adhered.

Another advantage of the bioadhesive compositions of the present invention is that the compositions adhere well to tissue, but do not adhere to most non-tissue surfaces. The compositions are also not self-adherent. The force required to disengage the bioadhesives from themselves is less than 0.1 lb/square inch, more preferably less than 0.01 lb/square inch, and optimally 0.001 lb/square inch or less. This is because the bioadhesives of the present invention form strong hydrogen bonds (non-permanent and noncovalent in nature) with certain molecular groups generally found on tissues, but which are absent from most other materials, including the bioadhesives themselves. Furthermore, even when these molecular groups do exist on non-tissue materials, potentially undesired bonding may be counteracted by placing the bioadhesives in an environment which dramatically reduces the adhesion between the bioadhesives and the other material. For example, because the bioadhesives are extremely hydrophilic, water molecules on the surface of the bioadhesive tend to reduce the tackiness and friction between the bioadhesive and non-tissue materials. This is an important feature that benefits the delivery of a medical device having these bioadhesive properties, as the device may be packed in a container of water to facilitate its removal from the container when application is desired.

In general, the bioadhesive compositions of the present invention are made by copolymerizing monomers with bioadhesive tendencies with monomers that provide improved internal cohesion and structural strength stability. In particular, monomers having a carboxyl functional side group (—COOH) which contribute to bioadhesion, such as acrylic acid and methacrylic acid, are copolymerized with cohesion enhancing monomers having hydrophobic hydrocarbon side chain portions to form a uniform and homogeneous copolymer which has less water content than the prior art hydrated bioadhesive hydrogels such as PAA and PMAA. The copolymers of the present invention maintain the desirable bioadhesive properties of the prior art hydrogels, but exhibit improved structural integrity. Unlike the prior art hydrogels, this increased structural integrity permits the resulting bioadhesive copolymer to be shaped and formed into useful medical devices without need for mixing with other materials. Furthermore, because of the superior internal cohesion of these bioadhesive compositions, adhered medical devices may be removed and little or no residue will remain at the mucosal or other tissue surface. Thus, medical devices incorporating these bioadhesive compositions are particularly suited to clinical applications requiring removal and reapplication or replacement of an adhered medical device without any intervening cleansing treatment to remove residue from the tissue surface.

It is theorized that the bioadhesives of the present invention exhibit an improved combination of adhesion and mechanical strength because of the close interaction of the carboxyl functional moieties and hydrophobic moieties in the resulting copolymer. As known to those of skill in the art, "moieties" are the side molecular units, such as —COOH groups for the carboxyl functional monomers, or phenyl rings and other hydrocarbon containing species for the hydrophobic monomers. The hydrophobic monomers are generally randomly polymerized and their moieties contact the carboxyl functional moieties in a nanometer length scale. Consequently, the inherently weak mechanical properties of polymers formed solely of PAA or PMAA (i.e., homopolymers) are not observed, because weak mechanical strength is attributable to the collective effect of the carboxyl functional moieties when they are spatially close together. However, the desired bioadhesive properties of the carboxyl functional moieties are preserved because the desired bioadhesion only requires a certain number of carboxyl functional moieties per polymer molecule surface area, without requiring these moieties to be distributed close together spatially on the surface.

Advantageously, the adhesive and physical properties of these bioadhesive copolymers can be selectively and individually optimized by varying the type and amount of the monomers used, the methods of synthesis (solution or bulk), and the reaction conditions such as temperature, reaction time and reaction rate. The adhesive and physical properties of the bioadhesive compositions of the present invention can also be modified by adjusting the ratio of carboxyl functional monomers to hydrophobic monomers in the polymerization reaction and thus the ratios of moieties (or monomeric units) in the resulting copolymer. Furthermore, these properties can also be adjusted by selecting more than two different monomers to be reacted to form the copolymer. For example, two different hydrophobic moiety monomers can be reacted with a carboxyl functional monomer to form a bioadhesive copolymer which incorporates three different types of monomeric units. Similarly two or more different carboxyl functional monomers can be reacted with one or more different hydrophilic carboxyl functional monomers to form a bioadhesive copolymer formed of three or more monomeric groups. The monomers reacted can be selected to achieve a particularly desired property. Thus, a mixture of an acrylic acid monomer and another carboxyl functional monomer might be reacted with a single type of hydrophobic monomer where it is desired to form a copolymer with reduced adhesion in comparison to a copolymer incorporating only acrylic acid monomers and the hydrophobic monomer. Other combinations are possible as well, as will be readily appreciated by those of skill in the art.

Preferred carboxyl functional monomers for copolymerization include acrylic acid and methacrylic acid, as these monomers form copolymers generally exhibiting stronger adhesion to tissue. However, as will be appreciated by those of skill in the art, other carboxyl functional monomers which exhibit bioadhesive properties when polymerized may also be used to form the bioadhesive materials of the present invention. These monomers include ethyl acrylic acid, propyl acrylic acid and butyl acrylic acid, and their isomers. However, when these monomers are used to form the copolymer, it is expected that the resulting copolymers will exhibit reduced adhesion to tissue in comparison to copolymers of acrylic acid or methacrylic acid.

Other carboxyl functional monomers having the following basic structure might also be used to form the copolymers of the present invention:

$$\begin{array}{c} R_1 \\ \phantom{R_1}\diagdown \\ \phantom{R_1}C{=}C{-}R_3{-}CO_2H \\ \phantom{R_1}\diagup \phantom{={-}}| \\ R_2 \phantom{={-}} X \end{array}$$

In the above structure, $R_1$ may be hydrogen or a methyl group. $R_2$ may be hydrogen, or methyl, ethyl or propyl groups. $R_3$ may be nothing, $(-CH_2)_n$ where n=1 to 4, or $-CH_2(C-)(CH_3)_2$. X may be hydrogen, methyl, ethyl, propyl or butyl groups, halogens such as fluorine, chlorine, iodine and bromine, or amino groups. Representative carboxyl functional monomers defined by the above structure include crotonic acid, dimethyl acrylic acid, pentenoic acid, tiglic acid, 2-hexenoic acid, 3-hexenoic acid, 6-heptenoic acid and 2,2-dimethyl-4-pentenoic acid.

It should be appreciated that many of the potential carboxyl functional monomers encompassed by the above structure and description will copolymerize to form compositions which adhere less strongly to tissue than copolymers formed from acrylic acid or methacrylic acid monomers. Consequently, these other monomers might be used to tailor the adhesive properties of the resulting copolymer to applications where reduced adhesive strength to tissue is desired. Furthermore, as with all polymerization reactions, the carboxyl functional monomer chosen should be stable (should not appreciably self react), be soluble in solution if polymerization is to take place in solution, and be capable of being copolymerized with the desired hydrophobic monomer.

Preferred hydrophobic monomers for copolymerization have a phenyl ring as a moiety, and should be chemically reactive and compatible with the carboxyl functional monomers selected for the polymerization reaction. Copolymerization ensures that a more uniform composition is created, and results in a copolymer with higher mechanical and cohesive strength in comparison to PAA or PMAA due to interaction of the hydrophobic moieties with one another. Hydrophobic monomers such as phenyl ethyl methacrylate, phenyl ethyl acrylate, phenyl methyl methacrylate, phenyl methyl acrylate, benzyl acrylate, and benzyl methacrylate, as well as acrylamides with phenyl rings as a side group are preferred. Other hydrophobic monomers which may be used include those having the following structure:

$$H_2C{=}\overset{\overset{\displaystyle Z}{|}}{C}{-}\overset{\overset{\displaystyle O}{\|}}{C}{-}O{-}(CH_2)_n{-}Y{-}Ar$$

$$H_2C{=}\overset{\overset{\displaystyle R_2}{|}}{C}{-}\overset{\overset{\displaystyle O}{\|}}{C}{-}N\diagup\overset{\displaystyle R_1}{\phantom{N}}\diagdown_{R_2}$$

Z=—H, —$CH_3$, or —$CH_2CH_3$

Y=nothing or O

Ar=$C_1$–$C_3$ alkyl substituted aromatic ring or unsubstituted aromatic ring n=1–5 or $R_1$=$C_1$–$C_5$ alkyl substituted aromatic ring or unsubstituted aromatic ring $R_2$=hydrogen or $C_1$–$C_5$ alkyl group.

Similarly, hydrophobic monomers having the following structure might also be used, provided that the monomers are stable, soluble in the solution that will be used for the polymerization reaction, and are capable of reacting with the carboxyl functional monomer(s) to form the bioadhesive copolymer:

$$H_2C{=}\overset{\overset{\displaystyle X}{|}}{C}{-}\overset{\overset{\displaystyle O}{\|}}{C}{-}O{-}(CH_2)_n{-}Y{-}Ar$$

$$H_2C{=}\overset{\overset{\displaystyle X}{|}}{C}{-}\overset{\overset{\displaystyle O}{\|}}{C}{-}N\diagup\overset{\displaystyle R_1}{\phantom{N}}\diagdown_{R_2}$$

X=hydrogen or $C_1$–$C_5$ alkyl group

Y=nothing or O

Ar=$C_1$–$C_3$ alkyl substituted aromatic ring or unsubstituted aromatic ring n=1–10 or $R_1$=alkyl side group having 1–10 carbon atoms, alkyl substituted aromatic ring, or unsubstituted aromatic ring $R_2$=hydrogen or alkyl side group having 1–5 carbon atoms.

Hydrophobic monomers defined by the above structures and description include benzyl methacrylate, phenyl acrylate, phenyl methacrylate, phenoxyethyl methacrylate, phenyl acrylamide, N-benzyl methacrylamide and benzyl methyl acrylamide. As will be appreciated by those of skill in the art, a great variety of hydrophobic moiety monomers may be substituted for those listed above. These hydrophobic monomers may be selected because they have similar chemical properties and structure to the hydrophobic monomers described above.

Preferably, the volume ratio of carboxyl functional monomers to hydrophobic monomers in the reaction mixture prior to polymerization is from 20:1 to 1:5, more preferably 10:1 to 1:1, and for certain embodiments, optimally 10:2 to 10:4. These same ratios are preferred for the resulting monomeric units (ratio carboxyl moieties to hydrophobic moieties) incorporated into the polymerized copolymer.

The bioadhesive hydrogels of the present invention may be made by conventional polymerization methods, as for example, those described in *Polymer Synthesis*, by P. Rampp and L. Merill, Huethig & Wepf (1986), the entirety of which is incorporated herein by reference. As one example, bulk polymerization/cross-linking can be used to make these bioadhesive copolymers. In this process, all monomers, an initiator and a cross-linker are mixed, degassed to remove oxygen, and heated to the appropriate temperature for several hours. Initiators that can be used to form bioadhesive materials of the present invention include dibenzyl peroxide, dicumyl peroxide, ammonium persulfate, azobisisobutyronitrile (AIBN), as well as other initiators known to those of skill in the art. Crosslinking compounds that can be used include ethylene glycol diacrylate, methylene bis acrylimide and the like. Typical reaction temperatures may range from 60° to 70° C. if AIBN is used as the initiator. Of course, higher or lower temperatures may be used depending upon the selected reactants, as will be appreciated by those of skill in the art. The particular reaction temperature and conditions should be selected to facilitate a complete reaction with respect to the reactants used.

Alternately, the polymerization/cross-linking reaction may take place in solution. In this process, all monomers, distilled water, an initiator and cross-linker are mixed, degassed to remove oxygen, and heated for several hours. To achieve better mechanical strength, it is preferred that all reactants be completely soluble so that a more uniform/ homogenous bioadhesive can be made. Furthermore, phase separation of the reactants is undesirable in most polymerizations where a translucent or transparent end-product is desired. Again, 60° to 70° C. is a typical reaction temperature, although higher or lower reaction temperatures may be employed, depending upon the reactants, as will be recognized by those of skill in the art in view of the teachings above.

When the reactants are completely soluble in solution, and no phase separation occurs, the resulting bioadhesive composition is often observed to be lightly translucent to almost transparent. This indicates that any inhomogeneity of the bioadhesive composition exists on a length scale which is less than that of visible light, namely, less than 0.4 to 0.7 microns. In other words, the bioadhesive compositions of the present invention, when copolymerized to form a translucent polymer, are homogeneous and uniform at all length scales of about 0.4 microns or greater. It is further estimated that the bioadhesive compositions of the present invention are homogeneous and uniform to all length scales greater than 0.1 microns. In contrast, as discussed above, the prior art bioadhesives were only homogeneous to the size of the bioadhesive particles in the mixture, namely, a length scale of greater than 1 micron, and typically 10–100 microns or more.

In addition, the translucent bioadhesives of the present invention transmit more than 30% of the visible light passing through them per millimeter of thickness. Moreover, for bioadhesives of the present invention which approach transparency, it is estimated that from 80% to more than 90% of visible light is transmitted per millimeter of thickness. In contrast, prior art bioadhesive compositions, which require physical mixing of hydrogels with other materials to form a useful device, form bioadhesive compositions which generally transmit less than 20% of visible light per millimeter of thickness.

The water content of the bioadhesives of the present invention can also be varied to optimize the bioadhesive for adhesion to certain types of tissue. For drier tissue surfaces, such as skin, it is preferred that the bioadhesive have a higher water content, and perhaps be fully hydrated. For wet tissue surfaces such as a mucosal layer, it is preferred that the water content of the bioadhesive be lower, and in some circumstances be fully dehydrated. When a dried bioadhesive is applied to a wet tissue surface, it will absorb water from the tissue surface, thereby bringing the tissue into more intimate contact with the bioadhesive, resulting in a stronger bond between the bioadhesive and the tissue.

The adhesive and cohesive properties of the bioadhesive compositions of the present invention are demonstrated below for several illustrative disclosed embodiments. It should be appreciated, however, that embodiments other than those described below, which may have different chemical compositions, adhesive properties and physical properties may be made by following the teachings contained herein.

EXPERIMENTAL EXAMPLES

In the examples described below, tensile strength was measured by first preparing a test sample of the bioadhesive by cutting it with a ASTM D412 DIE D struck with a hammer. This produced a sample having dimensions of about 33 mm by 3 mm, and a thickness of about 1 mm. The ends of the sample were then clamped to the stationary and moving clamp of a Chatillon TCD 200 Force Tester, manufactured by AMETEK, Largo, Fla. The pulling speed was set to two inches per minute, and the sample was pulled until it broke apart. The tensile strength was recorded as highest value for the force observed when the adhesive sample broke. Each bioadhesive composition was tested five times, and the average tensile strength is reported in Table I.

The adhesive strength of the bioadhesive compositions was determined by adhering the compositions to a chamois substrate (Viking Car Care Chamois, Schroeder & Tremaine, St. Louis, Mo.). The chamois substrate was first prepared by bonding it to an aluminum plate. The chamois substrate was then soaked in distilled water and squeezed to eliminate excessive water. The bioadhesive compositions to be tested were cut into rectangular sheets having dimensions of approximately 10 millimeters by 40 millimeters. The bioadhesive sheets were then placed flat on the chamois substrate so that only an area of about 15 millimeters by 10 millimeters of the bioadhesive sheet contacted the chamois substrate. The remainder of the bioadhesive sheet was laid on a piece of plastic film overlying the chamois to prevent adhesion to the chamois. A piece of glass was laid over the portion of the bioadhesive sheet which contacted the chamois, and a 1.8 pound weight was placed on the glass to press the adhesive sheet onto the chamois for 30 seconds.

The weight, glass and plastic film were then removed and the aluminum plate was attached to a mechanical slide. The mechanical slide was attached to the bottom plate of a Chatillon Force Tester. The free end of the adhesive sample, which did not contact the chamois substrate, was then clamped to the upper clamping jaw of the Tester leaving a free length of about 10 millimeters between the edge of the clamp and the portion of the bioadhesive composition adhered to the chamois substrate. The mechanical slide was then positioned by hand so that the peel-off point of the bioadhesive composition was directly under the direction of the pull by the clamp. The free end of the bioadhesive composition was then pulled at a rate of one inch per minute at a 90° angle from the adhered surface of the bioadhesive sheet, and the force required to peel the bioadhesive sheet from the chamois was measured. Each bioadhesive composition was tested 15 times, and the average adhesive strength in pounds/inch and range of observed adhesive strengths are reported in Table I.

The water content of the bioadhesive compositions was measured by storing the bioadhesive compositions in jars filled with distilled water for at least 24 hours to allow for full hydration. The bioadhesive compositions were then removed from the distilled water, and 1-inch diameter disks were cut from each bioadhesive composition. Water was removed from the surface of each disk by shaking and wiping gently using a Kimwipe™. The weight (W(wet)) of the disk was recorded. Each disk was then placed in an oven set to 70° C. and left overnight. The dried disks were then removed and allowed to reach room temperature. The weight (W(dry)) of the dried disk was then recorded. The water content of the bioadhesive compositions was determined as follows:

Water Content (%)=100×[W(wet)−W(dry)]/W(wet)

Example 1

As a control, 2.0 ml of acrylic acid, 6.0 ml of water, 10 mg of the initiator ammonium persulfide, and 20 mg of the crosslinker methylene bis acrylamide were added to a glass vial. The glass vial was sealed and oxygen was removed by blowing nitrogen gas in the liquid mixture for 2–5 minutes. The glass vial and its contents were then placed in an oven at a temperature of 65° C. overnight to ensure that the reaction was complete. The glass vial was then removed and the properties of the bioadhesive material were measured. As expected, the bioadhesive was found to be very tacky to tissue surfaces such as human skin and mucosal surfaces, as well as analogous animal and mammalian tissues, but had very poor cohesive strength.

Example 2

1.0 milliliter of acrylic acid, 0.1 milliliter of phenyl ethyl methacrylate (PEMA), 1.0 milliliter of distilled water, 10 microliters of the cross-linker ethylene glycol dimethacrylate (EGDMA), and 2 milligrams of AIBN were added to a glass vial. The glass vial was sealed and oxygen was removed by blowing nitrogen gas in the liquid mixture for 2–5 minutes. The glass vial and its contents were then placed in an oven at a temperature of 65° C. overnight to ensure that the polymerization reaction was complete. The glass vial was then removed. Qualitatively, the resulting bioadhesive was estimated to be much tackier to tissue surfaces than that of Example 3, below, but it is estimated that the tensile strength of the bioadhesive was less than that of Example 3.

Example 3

The reactants and conditions were identical to those described in Example 2 except that 0.2 ml of PEMA and 0.5 ml of water were used. The resulting bioadhesive was found to be less tacky than that in Examples 1 and 2. The equilibrium water content was lower, about 73%, and the mechanical strength was much greater than the bioadhesive compositions of Examples 1 and 2.

Example 4

The reactants and conditions were identical to those described in Example 3 except that 0.3 ml of PEMA was used. The resulting bioadhesive was less tacky than that of Examples 1–3, but had significantly greater mechanical strength.

Example 5

1.0 milliliter of acrylic acid, 0.4 milliliter of phenyl ethyl methacrylate (PEMA), 0.5 milliliter of distilled water, 10 microliters of the cross-linker ethylene glycol dimethacrylate (EGDMA), and 2 milligrams of AIBN were added to a glass vial. The glass vial was sealed and oxygen was removed by blowing nitrogen gas in the liquid mixture for 2–5 minutes. The glass vial and its contents were then placed in an oven at a temperature of 65° C. overnight to ensure that the polymerization reaction was complete. The glass vial was then removed. A translucent bioadhesive copolymer was observed to be formed. At wet conditions, the bioadhesive was tacky to tissue surfaces, but less so than the bioadhesives of Examples 1–3. The bioadhesive exhibited very good cohesive strength, as exhibited by its tensile strength measurement of 179 psi.

Example 6

The reactants and conditions were identical to those described in Example 5 except that 0.6 ml of PEMA was used. The resulting bioadhesive was found to be less tacky than those of Examples 1–3, but the mechanical strength of the bioadhesive copolymer was much stronger than that of all other examples.

Example 7

The reactants and conditions were identical to those described in Example 5 except that 1.0 ml of water was used instead of 0.5 ml. This lead to phase separation of the reactants. 10 mg of Carbopol (manufactured by B.F. Goodrich), which acts as a suspension agent, was added so that a quasi-uniform milky emulsion was formed. After reaction, the bioadhesive was approximately as tacky as that of Example 5, but the mechanical strength was much weaker than the composition of Example 5, indicating that a uniform/homogenous bioadhesive is important for achieving good mechanical strength.

Example 8

The reactants and conditions were identical to those described in Example 5 except that no water was added. A bulk polymerization/crosslinking reaction occurred rather than the solution polymerization of the previous examples. The resulting bioadhesive was hard and glassy. It became tacky and mechanically strong after being fully hydrated in water. The adhesion of the hydrated bioadhesive was worse than the composition of Example 5, but the mechanical strength was comparable. Bulk polymerization/crosslinking required a higher temperature of about 120° C. and second higher temperature initiator (such as dicumyl peroxide or the like) to achieve high monomer to polymer conversion.

Example 9

1.0 ml of acrylic acid, 1.0 ml of hydroxyl ethyl methacrylate (HEMA), 3.0 ml of water, 5 mg of the initiator ammonium persulfide and 5 mg of the crosslinker methylene bis acrylamide were added to a glass vial. The glass vial was sealed and oxygen was removed by blowing nitrogen gas in the liquid mixture for 2–5 minutes. The glass vial and its contents were then placed in an oven at a temperature of 65° C. overnight to ensure that the reaction was complete. The glass vial was then removed.

The resulting composition was a clear and soft bioadhesive with exceptional tackiness but rather weak mechanical strength. The bioadhesive had such strong adhesion but weak cohesion that it cohesively broke after being attached to tissue such as wet human skin and peeled away. This indicated that the importance of a hydrophobic monomer such as PEMA to provide mechanical strength to the copolymer.

Example 10

The reactants and conditions were identical to those described in Example 5 except that 0.2 ml of benzyl acrylate (BAC) was used as the hydrophobic monomer instead of PEMA. The resulting bioadhesive was found to be much tackier than that in Example 5. The equilibrium water content was about 60%, and mechanical strength was less than the composition of Example 5.

Example 11

The reactants and conditions were identical to those described in Example 5 except that 0.4 ml of BAC was used as the hydrophobic monomer instead of PEMA. The resulting bioadhesive was found to be less tacky than that of Example 10. The equilibrium water content was about 43%, and mechanical strength was stronger than that of the composition of Example 10.

Example 12

The reactants and conditions were identical to those described in Example 5 except that 0.6 ml of BAC was used as the hydrophobic monomer instead of PEMA. The resulting bioadhesive was found to be less tacky than that in Example 11. The equilibrium water content was about 30%, and mechanical strength was stronger than that of the composition of Example 11.

Example 13

The reactants and conditions were identical to those described in Example 5 except that 0.8 ml of BAC was used as the hydrophobic monomer instead of PEMA. The resulting bioadhesive was found to be less tacky than that in Example 12. The equilibrium water content was about 28%, and mechanical strength was stronger than that of the composition of Example 12.

Example 14

The reactants and conditions were identical to those described in Example 5 except that 1.0 ml of BAC was used as the hydrophobic monomer instead of PEMA. The resulting bioadhesive was found to be less tacky than that in Example 13. The equilibrium water content was about 21%, and mechanical strength was stronger than that of the composition of Example 13.

The water content, tensile strength, relative adhesion strength, and the ratio of hydrophilic carboxyl functional monomers to hydrophobic monomers of the compositions of Examples 1–14 are summarized below in Table I.

As shown by the data above, bioadhesive strength is reduced and tensile strength is increased dramatically with small increases in the amount of hydrophobic monomer. However, bioadhesive strength is drastically reduced while tensile strength shows little change when large amounts of hydrophobic monomer are added. The data in Table I also illustrates the differing properties resulting from copolymers incorporating differing hydrophobic monomers. For example, PEMA produced a copolymer with much higher tensile strength than BAC at ratios of 10:4 and 10:6 (carboxyl functional monomers to hydrophobic monomers), but both copolymers exhibit very similar adhesive strength. This is illustrated in FIG. 4, which compares copolymers of acrylic acid/PEMA (denoted as P series in FIG. 4) with copolymers of acrylic acid/BAC (denoted as B series in FIG. 4). Several of the compositions of Table I are graphed on FIG. 4, and a line is drawn to best fit the data for each of the PEMA and BAC copolymer series. As shown in FIG. 4, copolymers including BAC exhibited sharply reduced increases in tensile strength with increasing ratios of hydrophobic monomer in comparison to copolymers of PEMA.

Bioadhesive Intraurethral Device

The more uniform and homogeneous bioadhesive materials of the present invention are particularly useful in forming intraurethral devices to control urinary incontinence. Intraurethral devices which are formed of or incorporate the homogeneous bioadhesive materials described above have the advantage that the bioadhesive properties may be used to adhere the device to the urethra, and thereby prevent or minimize migration of the device into the bladder. By use of a bioadhesive mechanism to reduce or prevent migration, complex migration-minimizing structures of the prior art may be avoided. Furthermore, the homogeneous bioadhesive materials of the present invention do not leave residue or leave much less residue as compared to the prior art when removed, and are therefore especially well suited to applications where a medical device must adhere to tissue but occasionally needs to be removed or replaced, such as an intraurethral device.

Alternatively, other types of bioadhesives, as known to those at skill in the art, may also be used to form an intraurethral device which bonds to the urethra and prevents or minimizes migration. In selecting these bioadhesives, it

TABLE I

| Examples # | Water Content (%) | Tensile Strength (psi) | Average Adhesion Strength (lb/inch) | Adhesive Strength Range (lb/inch) | Volume Ratio Hydrophilic Carboxyl Functional Monomers/ Hydrophobic Monomers |
|---|---|---|---|---|---|
| 1 | 86 | 9.4 | ** | | 10/0 |
| 2 | 78 | * | * | | 10/1 |
| 3 | 73 | 26 | 0.59 | 0.33 to 0.91 | 10/2 |
| 4 | 62 | 61 | 0.42 | 0.28 to 0.53 | 10/3 |
| 5 | 58 | 179 | 0.57 | 0.48 to 0.75 | 10/4 |
| 6 | 47 | 486 | 0.34 | 0.25 to 0.46 | 10/6 |
| 7 | * | * | * | | 10/4 |
| 8 | * | * | * | | 10/4 |
| 9 | * | * | * | | 10/0 |
| 10 | 66 | 21 | ** | | 10/2 |
| 11 | 43 | 38 | 0.50 | 0.40 to 0.64 | 10/4 |
| 12 | 30 | 88 | 0.44 | 0.30 to 0.56 | 10/6 |
| 13 | 28 | 102 | 0.37 | 0.23 to 0.56 | 10/8 |
| 14 | 21 | 110 | 0.22 | 0.13 to 0.38 | 10/10 |

*Not measured
**Not able to measure due to technical difficulties (adhesion strength was so strong that the bioadhesive sheets broke during the tests)

should be appreciated that the primary force which would tend to dislodge an inserted urethral device is a shear force along the plane of the bioadhesive device surface in contact with the tissue surface. Consequently, low peel adhesion measured at 90° angles is desirable for adhesives chosen to be incorporated into the intraurethral.

Furthermore, natural absorption of body fluids into the adhesive may cause plasticization of the adhesive resulting in significant shear resistance reduction. Therefore, the adhesive used should be selected from those which experience less absorption of fluids or less degradation in the presence of fluids of the type found in the urethra.

With these considerations in mind, the present inventors contemplate that alternate bioadhesives for the intraurethral device may include: block copolymers of sugars having 2-ethyl hexyl acrylate; self-crosslinking acrylic pressure sensitive adhesives; hot melt applied acrylic pressure sensitive adhesives; colostomy based adhesives which contain PIB, polybutene, Kraton 1107, Aqualon and a tackifier resin; colostomy adhesives as described which include 2-ethyl hexyl acrylate, or which replace Aqualon with Karaya gum; Karaya gum plus Kraton 1107 and a tackifying resin; moisture cured silicone adhesives and moisture cured polyurethane prepolymer adhesives.

One particularly preferred alternate adhesive class is described in Mortazani et al., "An in-vitro Method for Accessing the Duration of Mucoadhesion," Journal of Controlled, Release 31 (1994), 207–212, the entirety of which is incorporated by reference as if fully set forth herein.

In one embodiment, a bioadhesive intraurethral device is formed as a hollow tube composed entirely from the cohesive bioadhesive materials of the present invention. As can be appreciated, the outer surface of the tube formed of such a bioadhesive material will adhere to the tissue surface to which it is placed in contact. For an intraurethral device, this surface will contact the inside of the urethra. However, because the bioadhesive material does not adhere well to itself, the inner lumen will remain free to open when the pressure differential between the proximal and distal portions of the urethral valve is sufficiently high, as described above.

Referring to FIG. 70, there is shown an embodiment of an intraurethral device incorporating the bioadhesive materials of the present invention. The device 510 includes a tubular body 512 having a proximal end 518, a distal end 520 and a central lumen 522 extending therethrough. The device 510 is formed entirely of the bioadhesive materials of the present invention, as described herein. Consequently, when placed in the urethra, the outer surface of tubular body 512 will contact the tissue surface and adhere thereto. The adhesion of tubular body 512 to the inside of the urethra will inhibit migration of device 510 from the position where it is initially placed.

The device 510 controls urinary incontinence by functioning primarily as a bulking agent or sealing device, which reversibly seals by collapsing at least part of the tubular body to seal lumen 522 in response to the previously described inwardly directed urethral forces. These forces on the urethra help to cause the tubular body to collapse and seal when micturition is undesired, thereby maintaining urinary continence. Conversely, when micturition is desired, the pressure exerted by the urethra and bladder neck decreases, thereby allowing the tubular body to open.

The tubular body 512 of the device 510 can also function as a reversible seal by kinking due to for instance bending of the tubular body in response to the previously described rotational descent of the bladder neck and urethra, such as during a hypermobility event.

The dimensions and configuration of the device 510 are generally similar to those of the previously described embodiment illustrated in FIGS. 21–31. The tubular body 512 may be longer and have a thicker wall, however, in order to enhance the device's ability to serve as a bulking agent, yet still take advantage of the urethral pressure gradient and other previously discussed aspects of urinary anatomy/physiology.

Typical ranges for the length of the tubular body portion 512 of the device 510 are approximately 0.5–3.0 cm, preferably about 0.5–2.0 cm. Typical ranges for the outside diameter of the tubular body 512 are generally similar to those of the previously described embodiments of intraurethral valves described herein. Typical ranges for the wall thickness of the tubular body 512 of the device 510 are approximately 0.15–3 mm, preferably about 0.2 or 0.4–1.5 mm, and more preferably about 0.8 or 1.2 mm. The tubular body 512 of the device 510 can also have a variable thickness wall as previously discussed, wherein the wall of the proximal portion of the tubular body is thinner than that of the distal portion to facilitate kinking of the proximal portion, such as a during a hypermobility event. In addition, as previously discussed, in order to facilitate kinking, the tubular body can have a noncircular cross section, such as elliptical, oval, rectangular, triangular, star-shaped, or semi-circular, at the desired point of kinking or throughout the length of the tubular body.

Moreover, the intraurethral devices incorporating the bioadhesives of the present invention can be a variety of cross-sectional shapes. For example, the cross-sectional shape may be oval, elliptical, rectangular, or triangular, or any other geometric shape. The only limitation on a selected cross-sectional shape is that it be capable of conforming to the surface of the urethra to control incontinence as described herein.

As will be apparent to one of skill in the art, the device 510 can be manufactured in accordance with any of a variety of techniques and materials used to shape and form polymeric materials, including extrusion and injection molding. Also as discussed above, in addition to anatomical considerations, the size and shape of various components of the device 510 are governed by the type of material used to construct the device.

Illustrated in FIG. 71, there is an alternate embodiment of an intraurethral device 610 formed as tubular body 612 having an inner and outer layer of different composition. The outer layer 630 of the tubular body 612 comprises bioadhesive materials. These bioadhesives may include the cohesive homogeneous copolymns of the present invention or other types of suitable bioadhesive materials. Consequently, when the outer surface of tubular body contacts the urethra, it will adhere thereto. The inner layer 640 of the tubular body 612, which defines the inner lumen 622 through which urine will pass, is preferably formed of a material which is soft or has a low modulus so that the inner layer will tend to close and be self-sealing when the urethra is in the resting or closed phase. Preferably, the inner layer 640 of material is selected so that the material will not adhere to itself, allowing the device to open in conjunction with the urethra during micturition or the voiding phase, thereby allowing urine to pass freely through the inner lumen 622.

For the two-layer structure, the desired feature of the inner layer 640 is the softness allowing the formability and thus sealing of the device within the urethra. A variety of different materials can be used to form the soft inner layer 640 of the two-layer tube structure. For example, chemically cross-linked hydrogel materials, such as those used in the contact lens business, and which have a high water content, may be used. These materials include hydroxyl ethyl methacrylate (HEMA), n-vinyl pyrrolidone (NVP) and dimethyl acrylamide (DMA), and combinations thereof. Furthermore, chemically and physically cross-linked hydrogel materials such as hydrophilic polyurethane, polyvinyl alcohol, and other materials with a high water content may also be used. Also, a combination of both chemically and physically cross-linked hydrogels may be used to form the soft inner layer 640 of the intraurethral device 610. The inner layer preferably has softness characterized by a Young's modulus between 1 KPa to 10 MPa, and more preferably between 10–100 KPa.

Moreover, for some embodiments, including those embodiments having three or more layers as described below, it may be preferred that the outer layer be provided with surface regions which are not bioadhesive. In the two layer context, as depicted in FIG. 71, for example, outer layer 630 may comprise alternating circumferential or longitudinal stripes of bioadhesive and nonbioadhesive materials. By providing an outer layer which has an outer surface which is not entirely bioadhesive, the adhesion of the intraurethral device to the urethra may be attenuated. Increasing the percentage of the surface of outer layer 630 which is bioadhesive will increase adhesive strength, and conversely, decreasing the percentage of bioadhesive surface will decrease adhesive strength.

In addition, the bioadhesive and nonbioadhesive regions can be arranged in a variety of ways other than as alternating circumferential or longitudinal stripes. The only limitation to alternate arrangements is that the bioadhesive surface be in sufficient amount and location so that adequate adhesion to the urethra is obtained and unwanted dislodgment of the device is minimized or eliminated. Thus, the bioadhesive surface regions can also be arranged as spots (random or uniform distribution) on the outer surface of the device, square patches, or other geometrical or amorphous shapes not occupying the entire outer surface of the outer layer 630.

In another embodiment, shown in FIG. 72, an intraurethral device 710 is made in which three separate layers form tubular body 712. A bioadhesive material is used to form the outer layer 730 of the tube, and consequently, device 710 has the desired bioadhesive properties which prevent or minimize migration of device 710 once it is place in the urethra. Layer 730 may incorporate the bioadhesive materials described above, and all or only a part of the surface of outer layer 730 may be provided with a bioadhesive material. As described in connection with device 610, inner layer 740 is formed of soft material which tends to self-seal without adhering to itself. A middle layer 735, inserted between layers 730 and 740 a hydrophobic elastomeric material such as silicone, polyurethane, polyacrylate elastomers and the like. Middle layer 735 functions as a barrier to reduce or prevent water/urine diffusion to adhesive layer 730 as it passes through lumen 722. Middle layer 735 therefore allows the bioadhesive properties of layer 730 to be maintained for a longer period of time, as urine tends to interact with the bioadhesive materials used to form layer 730 and reduce bioadhesion over time. Middle layer 735 also adds mechanical integrity to device 710. Furthermore, middle layer 735 may also be fashioned to bias lumen 722 to the closed position by an elastomeric or other force. Advantageously, different materials can be incorporated into middle layer 735 to increase or decrease the closure bias force, thereby providing the capability to tailor the device to the different incontinence profiles of different patients. The present inventors contemplate that a four-or-more-layer device might also be made in accordance with the teachings presented herein. For example, middle layer 735 might be replaced with two layers performing the combined function of single layer 735, to create a four-layer device.

Multi-layer tube structures as described herein can be formed by a variety of means. For example, coextrusion techniques, as known by those of skill in the art, can be used to form the multi-layer tubes described herein. Alternately, one layer can be preformed, and then coated with material of the second or third layer to form the multi-layer structure. For example, the outer homogeneous bioadhesive layer can be preformed, and thereafter coated with an inner layer of the ultrasoft material. Conventional bonding techniques may also be used to join two or more layers which were preformed separately, and then brought together to form the final multi-layer tube structure.

The tubular intraurethral devices of FIGS. 70–72 which incorporate bioadhesive materials are positioned in the urethra in a manner similar to other intraurethral devices described herein. However, because of the overall hydrophilic nature of the bioadhesive materials, it is preferred that the intraurethral devices be packaged in distilled water to facilitate handling. Preferably, a mandrel is inserted into the lumen of the intraurethral device when it is packaged in the saline solution. The device may be removed from the container by way of the mandrel, and placed in an introducer as described previously. The outer diameter of the insertion tube of the introducer is preferably coated with a lubricous coating to facilitate placement of the intraurethral tube without requiring K-Y jelly, as K-Y jelly would interfere with the bioadhesive properties of the device.

To insert the intraurethral device, the introducer is positioned into the urethra. The overlying sheath is removed to expose the bioadhesive outer surface of the intraurethral device to tissue, and the inserter is removed. Upon removal of the sheath of the introducer, a balloon may be inflated to press the device against the wall of the urethra to ensure that it is firmly bonded thereto. Alternately, upon removal of the sheath of the introducer, a mechanical press may be used to press the intraurethral device against the wall of the urethra to ensure firm bonding.

OTHER APPLICATIONS FOR COHESIVE HOMOGENEOUS BIOADHESIVES

In addition to being useful in the manufacture of intraurethral devices, the bioadhesive materials of the present invention may also be used in a variety of other biomedical applications. For example, the bioadhesive materials of the present invention would be particularly useful as a bonding agent to secure other types of medical devices to tissue. This would be particularly advantageous when a device needs to be removed or replaced with the same or a new device, or when a device needs to be positioned and repositioned prior to securement by suture or staples. Furthermore, where a device needs to be positioned and repositioned prior to securement by a healing process, or sealed to prevent flow around the device, bioadhesive materials of the present invention are optimally used to secure the device to tissue. Clinical examples of such applications include securing and sealing a stent into a lumen within the body, securing a patch to a hernia opening, securing a sling around the urethra, securing a valve into the lower esophageal sphincter, securing a pacemaker or defibrillator wires, securing a drainage catheter, or securing a hemodialysis graft. As will be appreciated by those of skill in the art, other applications where it is required to secure a device to tissue may also incorporate the bioadhesive materials of the present invention to form the bonding agent between the tissue and the device.

Furthermore, the bioadhesive materials of the present invention are also useful whenever it is necessary to secure tissue to tissue. A need to do this may arise when any tissue must be approximated or reapproximated during a clinical procedure, whether prior to securement by suture or staples, or securement by a healing process. The bioadhesive materials of the present invention may also be used to approximate the tissue temporarily to facilitate visualization or access. Examples of tissue-to-tissue bonding applications for the bioadhesive materials include aligning tissue after lacerations, vessel anastomosis, closing Chrons fistula in a colon, and a retraction during a surgical or medical procedure.

The bioadhesive materials of the present invention may also be used as a bonding agent to secure a barrier to a tissue. This application would be useful for any tissue that may need a barrier positioned and/or repositioned to prevent healing of adjacent tissue planes, to prevent tissue exposure to fluids and/or solids, or to prevent passage of adjacent fluids and/or solids past a tissue. Medical applications where this procedure may be useful include adhesion barriers, protection of stomach ulcers or esophageal mucosa from acid, protection of the diverticulosis bleed or a bowel fistula, and to adhere a cervical cap.

The novel bioadhesive materials described herein may also be used as part of a drug delivery device to deliver drugs to tissue. The bioadhesive materials will be useful for any device or delivery of a drug to a local site where the device may need to be adhered to tissue, and where the device needs to be positioned or repositioned, positioned or repositioned prior to securement by suture or staples, positioned or repositioned prior to securement by a healing process, or removed and/or replaced with a new drug delivery device. Particular medical applications where this might be useful include attachment of antibacterial agents for urinary tract infections, to plug TMR holes with angiogenesis growth factor, to deliver a local chemotherapy for a cancer, or to provide hormones in the vaginal canal.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A method of forming a medical device with a bioadhesive surface comprising:

copolymerizing at least a first carboxyl functional moiety-bearing monomer with at least a first hydrophobic moiety-bearing monomer to form a bioadhesive copolymer, said first hydrophobic moiety-bearing monomer being selected from the group consisting of:

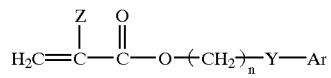

-continued

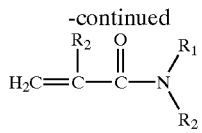

Z=—H, —CH$_3$, or —CH$_2$CH$_3$
Y=nothing or O
Ar=C$_1$–C$_3$ alkyl substituted aromatic ring or unsubstituted aromatic ring
n=1–5 or

R$_1$=C$_1$–C$_5$ alkyl substituted aromatic ring or unsubstituted aromatic ring
R$_2$=hydrogen or C$_1$–C$_5$ alkyl group
Z=—H, —CH$_3$, or —CH$_2$CH$_3$
Y=nothing or O
Ar=C$_1$–C$_3$ alkyl substituted aromatic ring or unsubstituted aromatic ring
n=1–5
R$_1$=C$_1$–C$_5$ alkyl substituted aromatic ring or unsubstituted aromatic ring
R$_2$=hydrogen or C$_1$–C$_5$ alkyl group wherein said copolymer has a tensile strength of at least about 10 psi; and providing the bioadhesive copolymer as a surface for a medical device, such that the surface remains exposed for adhesion to a tissue.

2. A bioadherent substrate, the substrate having at least a surface portion comprising a bioadhesive copolymer which selectively adheres to tissues, the copolymer having a tensile strength of at least 10 psi and transmitting at least 80% of the visible light passing through it per millimeter of thickness of the copolymer, the copolymer being formed in part by polymerization of hydrophobic monomers selected from the group consisting of:

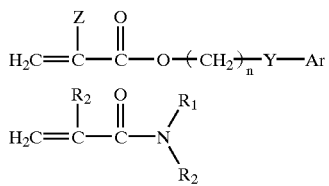

Z=—H, —CH$_3$, or —CH$_2$CH$_3$
Y=nothing or O
Ar=C$_1$–C$_3$ alkyl substituted aromatic ring or unsubstituted aromatic ring
n=1–5 or

R$_1$=C$_1$–C$_5$ alkyl substituted aromatic ring or unsubstituted aromatic ring
R$_2$=hydrogen or C$_1$–C$_5$ alkyl group.
Z=—H, —CH$_3$, or —CH$_2$CH$_3$
Y=nothing or O
Ar=C$_1$–C$_3$ alkyl substituted aromatic ring or unsubstituted aromatic ring
n=1–5

$R_1 = C_1–C_5$ alkyl substituted aromatic ring or unsubstituted aromatic ring $R_2 =$ hydrogen or $C_1–C_5$ alkyl group.

3. A method of manufacturing a medical device for removable attachment to a tissue surface, comprising the steps of:

providing a medical device having at least one tissue contacting surface thereon; and applying a coating to the tissue contacting surface;

wherein the coating comprises a polymerization product of at least a first monomer having a carboxyl functional moiety and at least a second monomer having a hydrophobic monomer moiety, the hydrophobic monomer being selected from the group consisting of:

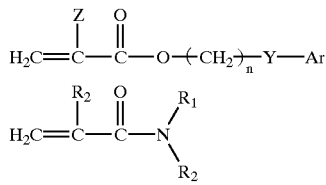

$Z = —H, —CH_3,$ or $—CH_2CH_3$ $Y =$ nothing or O $Ar = C_1–C_3$ alkyl substituted aromatic ring or unsubstituted aromatic ring $n = 1–5$ or $R_1 = C_1–C_5$ alkyl substituted aromatic ring or unsubstituted aromatic ring $R_2 =$ hydrogen or $C_1–C_5$ alkyl group.

$Z = —H, —CH_3,$ or $—CH_2CH_3$ $Y =$ nothing or O $Ar = C_1–C_3$ alkyl substituted aromatic ring or unsubstituted aromatic ring $n = 1–5$ $R_1 = C_1–C_5$ alkyl substituted aromatic ring or unsubstituted aromatic ring $R_2 =$ hydrogen or $C_1–C_5$ alkyl group.

4. A method of manufacturing a medical device as in claim 3, wherein the applying a coating step comprising applying a coating to the entire exposed surface of the medical device.

5. A method of manufacturing a medical device as in claim 3, further comprising the step of impregnating at least one of the medical device and the coating with a drug.

* * * * *